(12) United States Patent
de Buyl et al.

(10) Patent No.: US 6,426,211 B1
(45) Date of Patent: *Jul. 30, 2002

(54) XYLANASE DERIVED FROM A BACILLUS SPECIES, EXPRESSION VECTORS FOR SUCH XYLANASE AND OTHER PROTEINS, HOST ORGANISMS THEREFOR AND USE THEREOF

(75) Inventors: Eric de Buyl, Linkebeek; Andrée Lahaye; Pierre Ledoux, both of Brussels; Antoine Amory, Rixensart; René Detroz, Ohain; Christophe Andre, Grez-Doiceau, all of (BE); Roman Vetter, Burgdorf (DE)

(73) Assignee: Genencor International Inc., Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/073,055

(22) Filed: May 5, 1998

Related U.S. Application Data

(62) Division of application No. 08/275,526, filed on Jul. 15, 1994, now Pat. No. 6,180,382.

(30) Foreign Application Priority Data

Jul. 15, 1993 (GB) ............................................. 9314780

(51) Int. Cl.[7] ............................. D21C 3/00; D21C 1/00; C07G 17/00
(52) U.S. Cl. ........................ 435/278; 435/262; 435/267; 435/274; 435/277; 435/183; 435/200; 435/69.1; 435/252.3; 435/320.1
(58) Field of Search ................................. 435/183, 200, 435/252.2, 320.1, 69.1, 262, 262.5, 267, 278; 536/23.2

(56) References Cited

U.S. PATENT DOCUMENTS

| | | | |
|---|---|---|---|
| 2,821,501 A | | 1/1958 | Simpson |
| 4,828,994 A | * | 5/1989 | Fahnestock et al. ..... 435/172.3 |
| 5,457,045 A | * | 10/1995 | Anker et al. ................ 435/201 |

FOREIGN PATENT DOCUMENTS

| | | |
|---|---|---|
| CA | 603953 | 8/1960 |
| DE | 38 21 491 | 12/1989 |
| EP | 0 351 717 | 1/1990 |
| WO | WO 91/02792 | 3/1991 |
| WO | WO 91/02839 | * 3/1991 |
| WO | WO 92/03540 | 3/1992 |

OTHER PUBLICATIONS

Nissen et al. Xylanases for pulp and paper industry. Progress in Biotechnology–7, Proceedings of an International symposium, Wageningen, The Netherlands, Dec. 8–11, 1991, pp. 325–337.*

*Database Japio, AN–84–198978 and Database WPI, Derwent Publications, AN–84–316055, JP–59–198978, Nov. 10, 1984.

*Furusaki et al. "The Complete Nucleotide Sequence of the Sylanase Gene (xynA) of *Bacillus pumilus*," Febs Letters, V. 171, N. 2, Jun. 1984, pp. 197–201.

*Katsube et al., "Estimation of Sylanase Active Site from Crystalline Structure," *Protein Eng. Proc. Int. Conf. Protein Eng.*, 2nd Meeting, 1989, pp. 91–96.

*Moriyama et al., "Crystallization and Preliminary X–ray Studies of *Bacillus pumilus* IPO Sylanase," *J. Mool. Biol.*, V. 193, 1987 pp. 237–238.

*Nissen et al., "Xylanases for the Pulp and Paper Industry," Patent Abstracts of Japan, AN–85–138900, JP–60–075286, Apr. 27, 1985.

*Okada et al., "Xylanase of *Bacillus pumilus*," *Methods in Enzymology*, V. 160, 1988 pp. 632–637.

*Pan et al., "Expression of the Xylan–Degrading Genes of *Bacillus pumilus* IPO in *Saccharonyces cerevisiae*," *J. of Fermentation and Bioengineering*, V. 71, N. 5, 1991, pp. 303–308.

*Panbangred et al., "Expression of a Xylanase Gene of *Bacillus pumilus* in *Escherichia coli* and *Bacillus subtilis*," *Appliked Micro. and Bio.*, V. 22, 1985 pp. 259–264.

*Panbangred et al., "Molecular Cloning of the Genes for Xylan Degradation of *Bacillus pumilus* and Their Expression in *Escherichia Coli*," *Molecular and General Genetics*, V. 192, 1983, pp. 335–341.

*Panbangred et al., "Purification and Properties of Endoxylanase Produced by *Bacillus pumilus*," *Agric Biol. Chem.*, V. 47, N. 5, 1983 pp. 957–962.

*Simpson, F. J., "Microbial Pentosanases II. Some Factors Affecting the Production of Pentosanases by *Bacillus pumilus* and *Bacillus subtilis*," *Canadian Journal of Microbiology*, V. 2, 1956, pp. 28–38.

*Yang et al., "Hyperexpression of a *Bacillus circulans* Xylanse Gene in *Escherichia coli* and Characterization of the Gene Product," *Applied and Environmental Microbiology*, V. 55, N. 5, May 1989, pp. 1192–1195.

* cited by examiner

Primary Examiner—Ponnathapu Achutamurthy
Assistant Examiner—Manjunath N. Rao
(74) Attorney, Agent, or Firm—Genencor International Inc.

(57) ABSTRACT

A purified xylanase derived from *B. Pumilus* PRL B12 is disclosed. This xylanase is efficient for use in the biobleaching of wood pulp, permitting a strong reduction in the quantity of chlorine used and AOX compounds produced in classical and ECF wood pulp bleaching sequences as well as the quantity of ozone used in TCF sequences. The gene coding for the xylanase was isolated and purified and used to construct an expression vector therefor. A recombinant host strain of *B. licheniformis* is also disclosed which is efficient for expressing heterologous enzymes, including the xylanase when transformed by the expression vector.

16 Claims, 14 Drawing Sheets

```
TCATGTAACT CGCCTTGATC TATTTCATTT GTATCAAAGG ATTTATACAC         50

AAACAAGAGA CATCCATGCC GGGTTAAAGC AGTATCGTTC CATCTAACAG         100
AGAAGGNCTG CATGAAAGGA GGTGATGGGT TTTTCATCTT AGGGATGACA         150
GAACAATACG GATGAAAAAA GGAGAGGGAT GGAAA ATG                     188
                                        Met
```

| AAT | TTG | AAA | AGA | TTG | AGG | CTG | TTG | TTT | GTG | ATG | TGT | ATT | 227 |
|---|---|---|---|---|---|---|---|---|---|---|---|---|---|
| Asn | Leu | Lys | Arg | Leu | Arg | Leu | Leu | Phe | Val | Met | Cys | Ile | |
| | -25 | | | | -20 | | | | | -15 | | | |

| GGA | TTT | GTG | CTG | ACA | CTG | ACG | GCT | GTG | CCG | GCT | CAT | GCG | 266 |
|---|---|---|---|---|---|---|---|---|---|---|---|---|---|
| Gly | Phe | Val | Leu | Thr | Leu | Thr | Ala | Val | Pro | Ala | His | Ala | |
| | | | -10 | | | | | -5 | | | | | |

| GAA | ACG | ATT | TAT | GAT | AAT | AGG | ATA | GGG | ACA | CAC | AGC | GGA | 305 |
|---|---|---|---|---|---|---|---|---|---|---|---|---|---|
| Glu | Thr | Ile | Tyr | Asp | Asn | Arg | Ile | Gly | Thr | His | Ser | Gly | |
| 1 | | | | 5 | | | | | 10 | | | | |

| TAC | GAT | TTT | GAA | TTA | TGG | AAG | GAT | TAC | GGA | AAT | ACC | TCG | 344 |
|---|---|---|---|---|---|---|---|---|---|---|---|---|---|
| Tyr | Asp | Phe | Glu | Leu | Trp | Lys | Asp | Tyr | Gly | Asn | Thr | Ser | |
| | 15 | | | | | 20 | | | | | 25 | | |

| ATG | ACA | CTC | AAT | AAC | GGC | GGG | GCA | TTT | AGT | GCA | AGC | TGG | 383 |
|---|---|---|---|---|---|---|---|---|---|---|---|---|---|
| Met | Thr | Leu | Asn | Asn | Gly | Gly | Ala | Phe | Ser | Ala | Ser | Trp | |
| | | | | 30 | | | | | 35 | | | | |

| AAC | AAT | ATT | GGA | AAT | GCC | TTA | TTT | CGA | AAA | GGA | AAG | AAG | 422 |
|---|---|---|---|---|---|---|---|---|---|---|---|---|---|
| Asn | Asn | Ile | Gly | Asn | Ala | Leu | Phe | Arg | Lys | Gly | Lys | Lys | |
| 40 | | | | | 45 | | | | | 50 | | | |

| TTT | GAT | TCC | ACT | AAA | ACT | CAT | CAT | CAA | CTT | GGC | AAC | ATC | 461 |
|---|---|---|---|---|---|---|---|---|---|---|---|---|---|
| Phe | Asp | Ser | Thr | Lys | Thr | His | His | Gln | Leu | Gly | Asn | Ile | |
| | | | 55 | | | | | 60 | | | | | 65 |

| TCC | ATC | AAC | TAC | AAC | GCA | GCC | TTT | AAC | CCG | GGC | GGG | AAT | 500 |
|---|---|---|---|---|---|---|---|---|---|---|---|---|---|
| Ser | Ile | Asn | Tyr | Asn | Ala | Ala | Phe | Asn | Pro | Gly | Gly | Asn | |
| | | | | 70 | | | | | 75 | | | | |

| TCC | TAT | TTA | TGT | GTC | TAT | GGC | TGG | ACA | CAA | TCT | CCA | TTA | 539 |
|---|---|---|---|---|---|---|---|---|---|---|---|---|---|
| Ser | Tyr | Leu | Cys | Val | Tyr | Gly | Trp | Thr | Gln | Ser | Pro | Leu | |
| | | 80 | | | | 85 | | | | 90 | | | |

FIG. 1a

```
GCT GAA TAC TAC ATT GTT GAG TCA TGG GGC ACA TAT CGT              578
Ala Glu Tyr Tyr Ile Val Glu Ser Trp Gly Thr Tyr Arg
            95                  100

CCA ACA GGA ACG TAT AAA GGA TCA TTT TAT GCC GAT GGA              617
Pro Thr Gly Thr Tyr Lys Gly Ser Phe Tyr Ala Asp Gly
105             110                 115

GGC ACA TAT GAC ATA TAT GAA ACG CTC CGT GTC AAT CAG              656
Gly Thr Tyr Asp Ile Tyr Glu Thr Leu Arg Val Asn Gln
        120             125                 130

CCT TCT ATC ATT GGA GAC GCT ACC TTC AAA CAA TAT TGG              695
Pro Ser Ile Ile Gly Asp Ala Thr Phe Lys Gln Tyr Trp
                135                 140

AGT GTA CGT CAA ACA AAA CGC ACA AGC GGA ACG GTC TCC              734
Ser Val Arg Gln Thr Lys Arg Thr Ser Gly Thr Val Ser
        145             150                 155

GTC AGT GAG CAT TTT AAA AAA TGG GAA AGC TTA GGC ATG              773
Val Ser Glu His Phe Lys Lys Trp Glu Ser Leu Gly Met
            160                 165

CCA ATG GGA AAA ATG TAT GAA ACA GCA TTA ACT GTA GAA              812
Pro Met Gly Lys Met Tyr Glu Thr Ala Leu Thr Val Glu
170             175                 180

GGC TAC CGA AGC AAC GGA AGT GCG AAT GTC ATG ACG AAT              851
Gly Tyr Arg Ser Asn Gly Ser Ala Asn Val Met Thr Asn
        185             190                 195

CAG CTG ATG ATT CGA TAA AAGCATATGA AAAAAGCCAG CAAAAAATGG         899
Gln Leu Met Ile Arg
                200

CTGGCTTTTT TCTATGATAA TTTTTCAACT TCCACTCTGC CAGAAAAGAA           949
CGTCGCGCCG CCTCCCATAT CTGCCAATCG ATCAGGTGTT AACCCATTCA           999
CTAAATGCTT TTTGCCTTTT TGA                                       1022
```

FIG. 1b

XYLANASE DERIVED FROM A BACILLUS SPECIES, EXPRESSION VECTORS FOR SUCH XYLANASE AND OTHER PROTEINS, HOST ORGANISMS THEREFOR AND USE THEREOF

This application is a divisional of 08/275,526 Jul. 15, 1994 now U.S. Pat. No. 6,180,382, Jan. 30, 2001.

The present invention relates to heterologous enzymes produced by recombinant strains of *Bacillus licheniformis* and, in particular, to a xylanase derived from *Bacillus pumilus* PRL B12 which is efficient for use in the biobleaching of lignocellulosic pulp, expression vectors and recombinant *Bacillus licheniformis* hosts for the expression of the xylanase, and the use of the xylanase in the biobleaching of lignocellulosic pulp.

A common objective in the manufacture of products (such as paper products) from lignocellulosic pulps is to provide a pulp from which the product produced has as high a final brightness as is possible. A major factor that limits such final brightness is the quantity of lignin present in the pulp.

Lignin in such lignocellulosic pulps is mostly bound up with hemicellulose in a lignocellulosic complex. A major interface between the lignin and the remainder of the carbohydrates of the lignocellulosic complex is formed by xylan (1,4-β-D-xylan) which is bonded thereto. To remove the lignin from the pulp, these bonds must first be broken.

Conventionally, lignocellulosic pulps, such as wood pulp, are delignified by being chemically-cooked. While being extremely useful for its purposes, (up to ninety-five per cent of the lignin present may be removed therefrom by such chemical-cooking), chemical-cooking cannot, by itself, reach higher levels of delignification without severely attacking the carbohydrates in the pulp. Thus, cooking must be stopped before the loss of carbohydrates becomes too important and before further delignification has occurred. This remaining lignin imparts a brown color to the cellulosic fibers in the pulp, thereby preventing the product fabricated therefrom from having as high a final brightness as possible.

To obtain further delignification of the pulp after chemical-cooking, various "bleaching" sequences are used. Conventionally, such bleaching sequences include "Classical" (or conventional) bleaching sequences and Elemental Chlorine Free bleaching sequences. These bleaching sequences include a delignification stage followed by a series of bleaching stages. In the delignification stage, the pulp is first subjected to a chlorine and/or chlorine dioxide treatment step, usually followed by an alkaline extraction step.

While being effective for facilitating the removal ("delignification") of substantial quantities of lignin from the chemically-cooked pulp, treatment of the pulp nonetheless suffers from drawbacks. Perhaps the most troublesome of these drawbacks (especially in the case of classical sequences) is that their use results in discharges of chlorinated compounds which have been linked to the formation of absorbable organic halides (AOX). AOX compounds have been associated with environmental toxicity. It is believed that the AOX concentration in effluents is directly linked to the quantity of chlorine and chlorine dioxide compounds that are used in the process. Thus, AOX levels have become commonly used as a standard in the industry for determining the content of chlorinated organics in the bleaching plant's effluents. As such, industries, such as the wood pulp and paper industry, which make products from such pulp have come under increasing pressure and regulation to reduce both AOX production and the consumption of both chlorine and chlorine dioxide used during bleaching.

To reduce or eliminate AOX production and the consumption of $Cl_2$ and $ClO_2$ while still achieving acceptable levels of delignification, it has been proposed to utilize various hemicellulolytic enzymes to facilitate lignocellulosic pulp delignification (in a process commonly referred to as "biobleaching"). In particular, it has been proposed to use of a wide variety of diverse xylanases which are secreted by a range of various fungi and bacteria, including bacteria of the genus Bacillus, for treating the pulp. However, these attempts have had varying degrees of success depending upon the precise characteristics of the xylanase which has been employed therefor. To be successfully employed in commercial biobleaching applications, a xylanase should be efficient over the pH range naturally possessed by the pulp when the xylanase is utilized during biobleaching. Furthermore, the xylanase should be devoid of any residual cellulase activity.

In biobleaching, xylanase may be added to the pulp after it has exited the chemical-cooker, but before it has been chemically-treated. At that point, the pulp typically has a pH in the range of about 7.0 to 9.5. The identification and utilization of a xylanase which is efficient over this alkaline pH range would greatly reduce the control that must be maintained over that aspect of the process conditions as well as reduce the quantity of chlorine and reactive oxidants needed. to chemically-treat the chemically-cooked pulp.

It has been known for some years that microorganisms of the species *Bacillus pumilus* extracellularly secrete xylanases. Indeed, as early as 1960 it was disclosed that the culture media of *B. pumilus* contains xylanases which make this culture broth useful for food processing applications (see Canadian Letters Patent No. 603,953 and U.S. Pat. No. 2,821,501). However, nowhere do those patents either disclose, teach or suggest the isolation and/or purification of the enzymes (including the xylanases) from the culture broth into which they are secreted. Furthermore, it was reported therein that in pH's above 8, those xylanases will generally be inactivated.

To the best of our knowledge, the xylanase of only two strains of *Bacillus pumilus* have ever been isolated and/or purified : *Bacillus pumilus* IPO and *Bacillus pumilus* DSM 6124. However, there is nothing to indicate whether the xylanase from *B. pumilus* PRL B12 would have potential usefulness in biobleaching applications.

Only one xylanase from any strain of *B. pumilus* has ever been proposed for use in biobleaching, and that xylanase was from a specially designed mutant—*B. pumilus* DSM 6124. The isolation and purification of the xylanase secreted from *B. pumilus* DSM 6124, as well as its use in biobleaching has been disclosed in International Publication No. WO 91/02839 and International Publication No. WO 92/03540. However, as reported therein, the xylanase of strain DSM 6124 has an optimum pH of only 5–7 and appears to be of limited efficiency for the delignification of pulps having pH's of up to only about 8.5.

The presence, in the culture broth, of extracellular xylanases secreted by *Bacillus pumilus* PRL B12 and *B. pumilus* PRL B92 has also long been known, being reported as early as 1954 (1). It was further reported therein that, when in the milieu of the culture broth, the xylanase of *B. pumilus* PRL B12 is stable up to pH 11. However, nowhere does that reference either disclose, teach or suggest the isolation and/or purification of the xylanase from the culture broth into which it is secreted, nor is there any indication whatsoever in (1) as to what physical characteristics such an isolated and/or purified xylanase would have when not in the milieu of the culture broth. Furthermore, those xylanases have never been proposed for use in the biobleaching of chemical pulp.

It is known that, when in the culture broth into which they are secreted, xylanases are often contaminated by other enzymes. This can make the isolation and purification of the xylanase difficult and costly. This is particularly significant in that there is no information in (1) as to whether or not those xylanases ever were, or ever could be, isolated and/or purified, nor is there any information in (1) as to how difficult or successful one could expect such a task to be.

Furthermore, it is known that, in the culture broth, the contamination of the xylanase by other enzymes can effect the apparent physical characteristics of the xylanase, including its efficiency over different pH ranges. This aspect is particularly notable in light of the fact that xylanases exhibit a wide variety of characteristics, even when secreted from extensively homologous microorganisms of the same genus.

Thus, it can be seen that there still remains a need to locate and provide an isolated and/or purified xylanase which is efficient for the delignification of lignocellulosic pulp having a pH in the alkaline range of 7–9.5, so as to be useful for the pretreatment of lignocellulosic pulp by facilitating delignification of the lignocellulosic pulp before the bleaching thereof. In this fashion, the xylanase of the present invention permits a reduction in the quantity of chlorine, chlorine dioxide and other/or reactive oxidants which are needed to be utilized in the bleaching sequences for chemically-treating the lignocellulosic pulp, as well as a reduction in the production of AOX compounds, while still providing a lignocellulosic pulp that has an acceptably-low lignin content (as measured by the Kappa Index of the pulp).

It is further desireable to provide a host for expressing various enzymes, such as the xylanase, in good yields. In this regard, it is noted that if the enzyme yield from the host organism is too low, then enzyme production will be inefficient and too expensive.

While strains of *B. pumilus* are often cited as being hyper-producers of xylanase, the yields obtained therefrom are nonetheless too low to permit their use in industrial applications.

In order to obtain an increase in the yield of *B. pumilus* xylanase, it has been proposed to clone the xylanase gene(s) from *Bacillus pumilus* IPO into compatible hosts for achieving the heterologous expression of the xylanase in increased yields from the transformed hosts. The expression of the xylan-degrading genes of *Bacillus pumilus* IPO in species of *Escherichia coli, Bacillus subtilis* and *Saccharomyces cerevisiae* have all been disclosed. However, we are not aware of any disclosure of the usefulness of those transformed hosts for industrial applications.

In spite of the above references, it nonetheless still remains desireable to identify and prepare suitable hosts which are stable, capable of use in commercial applications and which are capable of extracellularly secreting xylanase, and in particular xylanase derived from *B. pumilus* PRL B12, in suitable yields.

Strains of *Bacillus licheniformis* are routinely used as hosts for the heterologous extracellular expression of various neutral and acidic enzymes (mainly proteases and alpha-amylases) in large scale industrial situations.

While success has been achieved in obtaining the heterologous expression of these neutral and acidic enzymes noted above, the use of the strains of *B. licheniformis* for the heterologous production of enzymes, such as xylanase, under alkaline conditions nonetheless presents several drawbacks. One of these drawbacks is that *B. licheniformis* is a producer of alkaline proteases, which can degrade xylanases and other enzymes under alkaline conditions. Such a feature is an obvious disadvantage and disincentive to the use of *B. licheniformis* as a host for the secretion of a xylanase. Further, even if making the deletions of the alkaline protease gene had been suggested, there would be no guarantee of success, especially in light of International Publication No. WO 91/02792, wherein it was reported that the presence of even a part of a protease gene can induce a reduction in the productivity of heterologous enzymes by the strain. Accordingly, to the best of our knowledge, no one has suggested the use of strains of *Bacillus licheniformis* for the heterologous expression of xylanase.

Thus, it can be seen that there further remains a need to provide a stable host capable of expressing such a xylanase in high yields.

It is a primary object of the present invention to identify, purify and provide a xylanase which is efficient for facilitating the delignification of lignocellulosic pulp, and in particular wood pulp, having a broad alkaline pH range and, in particular, a preferred pH range of 7.0–9.5.

It is another primary object of the present invention to identify and prepare suitable hosts which are stable, easy to use in commercial applications and which are capable of extracellularly secreting, in suitable yields, various enzymes, and in particular xylanase, especially xylanase derived from *B. pumilus* PRL B12, under alkaline conditions.

It is a further object of the present invention to isolate and purify the gene (nucleotide sequence) that codes for the xylanase of the present invention, as well as to provide an appropriate vector therefor which is useful when transformed in a suitable host, such that heterologous expression of the xylanase of the present invention may be achieved.

A still further object of the present invention is to provide expression vectors which include the nucleotide that codes for the xylanase of *Bacillus pumilus* PRL B12 and methods for the preparation thereof.

In still another aspect of. the present invention, a further object is to provide expression hosts for the expression vectors of the xylanase of the present invention, as well as for other enzymes, such as alpha-amylase, pullulanase, subtilisin and alkaline protease.

In still yet another aspect of the present invention, a further object is to provide an enzymatic treatment employing such a xylanase which permits a reduction in the quantity of chlorine, chlorine dioxide and other reactive oxidants used for delignification during biobleaching, as well as a reduction in the production of AOX compounds while still permitting a pulp to be obtained that has an acceptably-low lignin content.

In accordance with the teachings of the present invention, a purified xylanase that is derived from *B. pumilus* PRL B12 and mutants and variants thereof, is disclosed. This xylanase consists essentially of the amino acid sequence of amino acids numbered 1 to 200 of FIGS. 1*a* and 1*b* and mutants and variants of this amino acid sequence. This xylanase is efficient for facilitating the delignification of pulp having a pH, preferably, in the range of.7.0 to 9.5.

Alternatively, a purified xylanase is disclosed having a molecular weight of about 26 kDa as determined by an SDS-PAGE gel electrophoresis method as defined herein, an isoeletric point of about 9.8–9.9 in terms of a value as measured by an isoeletric focusing method as defined herein, an optimum temperature of about 55° C. as measured by a xylan hydrolysis assay method as defined herein and an optimum pH of about 6.5–7.5 as measured by a xylan hydrolysis assay method, as defined herein.

In another alternative, a purified xylanase is disclosed that has a molecular weight of about 26 kDa as determined by an SDS-PAGE gel electrophoresis method as defined herein and a molecular weight of about 22,500 kilodaltons (and more precisely about 22,534 kilodaltons) as deduced from the amino acid sequence of the mature xylanase by a deduction method as defined herein.

Finally, it is noted that the purified xylanase disclosed herein has, for the biobleaching of lignocellulosic pulp, an optimum xylanolytic activity of about 7.5–8.5 as measured by the kappa index of the lignocellulosic pulp treated thereby in a method defined herein.

By the term "as defined herein" what is meant is the method defined in the various examples set forth below.

By the term "derived from" when used in reference to *B. pumilus* PRL B12 and the xylanase and the nucleotide sequences disclosed herein, what is meant are the xylanase and the nucleotide sequences which are native to (or which are identical to those xylanase and nucleotide sequences which are native to) *B. pumilus* PRL B12.

In further accordance with the teachings of the present invention, a xylanase is disclosed herein that is heterologously-produced by and obtained from a microorganism of the genus Bacillus of the type which has a naturally-occurring alkaline protease gene. It is preferred that such hosts be aerobic. It is further preferred that such hosts not be thermophilic. Examples of such hosts include microorganisms of the species *Bacillus subtilis* and *Bacillus licheniformis*. Other examples include microorganisms of the species *Bacillus alkalophilus, Bacillus lentus* and *Bacillus amyloliquefaciens*. It is further preferred that this xylanase be heterologously-produced by and obtained from such a microorganism which has had the alkaline protease gene deleted therefrom, such as *B. licheniformis* SE2 delap1, *B. licheniformis* SE2 delap3, *B. licheniformis* SE2 delap6 and *B. subtilis* SE3. It is still further preferred that the xylanase be expressed heterologously by, and obtained from, strains of such microorganisms which have been transformed to include the xylanase coding sequence (and preferably, the entire xylanase gene) of *B. pumilus* PRL B12, so that the xylanase can be expressed thereby.

Alternatively, disclosed herein is a xylanase obtained from a strain of *Bacillus pumilus*, such as *B. pumilus* PRL B12.

In still further accordance with the teachings of the present invention, a process is disclosed herein for producing a xylanase in a Bacillus species. The process includes transforming a suitable strain of a Bacillus with a nucleotide sequence coding for at least the mature portion of the xylanase (SEQ ID NO:34). In this manner, a Bacillus having a complete xylanase gene expression unit is formed. The Bacillus is then cultured under suitable conditions for the expression of xylanase. Finally, the process disclosed involves recovering the xylanase from the culture. In a preferred embodiment, the Bacillus is *Bacillus licheniformis*. It is further preferred that the nucleotide sequence is derived from *Bacillus pumilus* PRL B12.

In yet further accordance with the teachings of the present invention, the gene (DNA molecule) coding for the xylanase of *B. pumilus* PRL B12 has been isolated therefrom and purified. In this regard, the nucleotide sequence of the entire xylanase gene of *B. pumilus* PRL B12 is disclosed. This nucleotide sequence includes those nucleotides coding for the mature xylanase, as well as those nucleotides coding for the precursor xylanase (SEQ ID NO:31) of *B. pumilus* PRL B12 (SEQ ID NO:32). This nucleotide sequence further includes promoters of the gene, as well as upstream and downstream nucleotide sequences.

In still further accordance with the teachings of the present invention, suitable expression vectors are disclosed herein. A preferred expression vector having, as a component thereof, the nucleotide sequence coding for the mature xylanase is disclosed, in addition to methods for the preparation thereof. Alternatively, this expression vector can further include the nucleotide sequences (SEQ ID NO:30) coding for the precursor xylanase. If desired, the upstream and/or downstream coding sequences of the xylanase gene may also be included. Most preferably, this expression vector includes the entire xylanase gene (SEQ ID NO:35) seen in FIGS. 1*a* and 1*b*. This most preferred expression vector is pUB-BPX12.

Other expression vectors disclosed herein include pUBDEBRA1, pKAC1, pLI1, pL7SBT, pL7TAKA, each of which code for various other proteins, so as to permit the heterologous expression thereof by the expression hosts disclosed herein.

In still further accordance with the teachings of the present invention, suitable hosts have been identified and methods for the preparation thereof have been disclosed. The hosts are stable, are able to operate effectively under varying process conditions and are capable of the heterologous production of enzymes, including xylanase derived from *B. pumilus* PRL B12, in good yields. Preferably, these hosts include (biologically pure cultures of) strains of *Bacillus licheniformis* and, in particular, the strain designated herein as *B. licheniformis* SE2 delap1 and mutants and variants thereof, such as the strains designated herein as *B. licheniformis* SE2 delap3 and mutants and variants thereof and *B. licheniformis* SE2 delap6 and mutants and variants thereof. Disclosed herein are also methods for preparing such strains of *B. licheniformis* by performing chromosomal deletions of the gene(s) thereof which code for alkaline protease. In this regard, deletion plasmids LD1, LD3 and LD6, and the methods for the construction thereof, are also disclosed herein.

In yet further accordance with the teachings of the present invention, the use of the xylanase of the present invention is disclosed herein as a treatment in the biobleaching of lignocellulosic pulp, such as Kraft wood pulp. Preferably, the xylanase may be used as a pretreatment in conjunction with traditional bleaching sequences. More particularly, use of the xylanase is disclosed as a pretreatment to classical bleaching sequences of the type CEDPD and C/DEDPD, as those sequences are defined herein. Also more particularly, use of the xylanase is disclosed as a pretreatment in conjunction with Elemental Chlorine Free Sequences of the type DEDPD, as those sequences are defined herein.

In still yet further accordance with the teachings of the present intention, the use of the xylanase of the present invention is disclosed herein in the biobleaching of lignocellulosic pulp in Totally Chlorine Free sequences. More particularly, use of the xylanase in Totally Chlorine Free sequences of the type OQPZP. It is especially preferred that, in such sequences, the xylanase be used in conjunction with the sequestrant (Q)step to give the sequence OX/QPZP.

It is especially preferred to use this xylanase in the sequences described above for the biobleaching of wood pulp and, more particularly, kraft wood pulp.

In still yet further accordance with the teachings of the present invention, an enzymatic treatment employing the xylanase is disclosed. Preferably, such a treatment is a pretreatment for classical and Elemental Chlorine Free bleaching sequences or in conjunction with one of the steps of a Totally Chlorine Free bleaching sequence. This enzymatic treatment permits a reduction in the quantity of chlorine, chlorine dioxide and/or other reactive oxidants needed to be used for subsequently chemically-treating the lignocellulosic pulp, as well as a reduction in the production of AOX compounds, while still permitting a pulp to be obtained which has an acceptably-low lignin content. Furthermore, this enzymatic pretreatment either: (a) does not diminish the final product brightness achieved (in the case of classic sequences or ECF sequences); or (b) still provides a final product brightness which is satisfactory while employing acceptable quantities of reactants (in the case of TCF sequences).

The use of the xylanase of the present invention in the treatment (biobleaching) of lignocellulosic pulp is usually done in a separate stage. It may also be done in combination with sequestrants. The xylanase can therefore be used not only to reduce the chemical charges of chlorine, chlorine dioxide and/or other reactive oxidants, such as oxygen, ozone or peroxide, but it also decreases the costs of the biobleaching process.

It is noted that the xylanase of the present invention has use not. only in the biobleaching of lignocellulosic pulp (as will be discussed at greater length below), but it is also useful in the preparation of xylooligosaccharides from vegetable materials.

FIGS. 1a and 1b show the nucleotide sequence (SEQ ID NO:1) of the gene coding for the xylanase of the present invention and the amino acid sequence of the precursor xylanase of the present invention, including the presequence and the mature enzyme, coded for by the nucleotide sequence.

Figure 2:
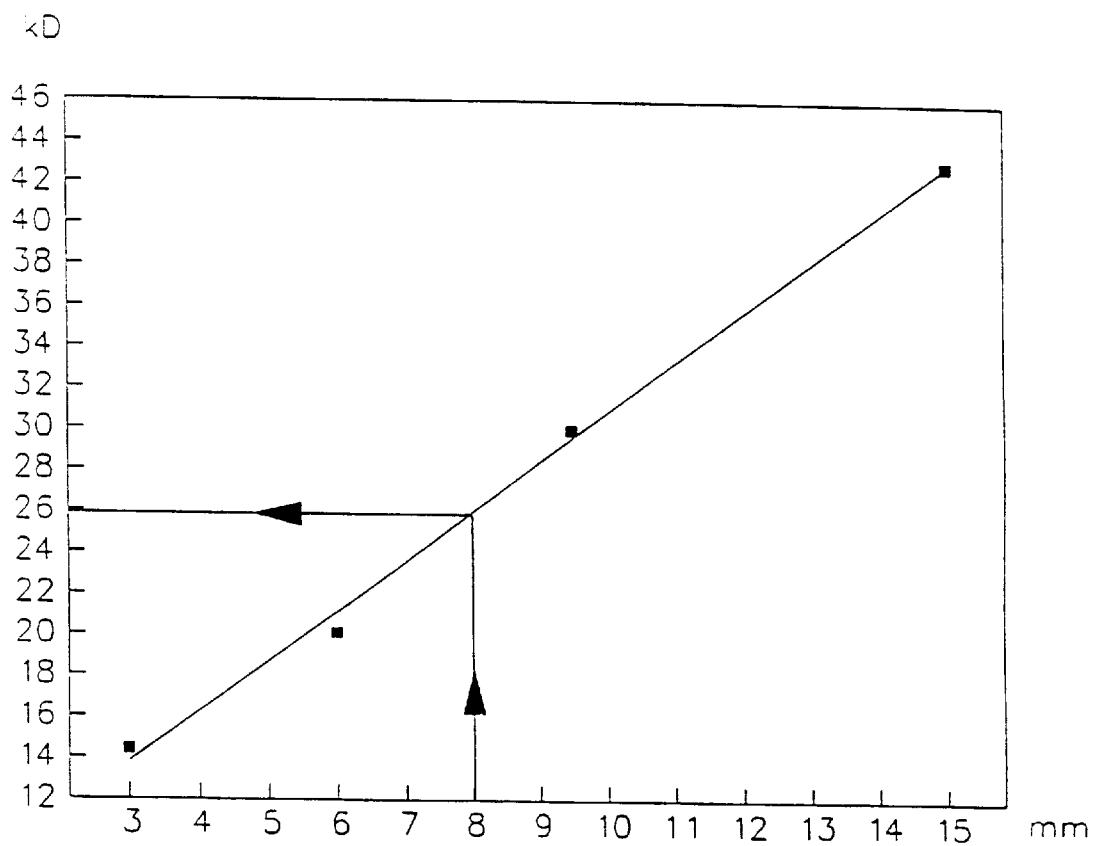
FIG. 2 is a graph illustrating the results of the SDS-PAGE Analysis for determining the molecular weight of the xylanase of the present invention in which the Y-axis represents the molecular weight in kilodaltons (kD) and the X-axis represents the migration distance in millimeters (mm).

The xylanase of the present invention is produced by gene(s) derived from *Bacillus pumilus* PRL B12. The invention also concerns mutants and variants of this xylanase.

As used herein, the term "mutants and variants of this xylanase" and like phrases, refer to xylanases that are obtained by the alteration of the DNA nucleotide sequence of the structural gene coding for the xylanase of the present invention or a derivative thereof. Such variants or mutants of the xylanase of the present invention may be expressed and produced when the DNA nucleotide coding sequence encoding therefor is inserted into a suitable vector and/or a suitable host organism. This definition includes such xylanases which are either heterologously expressed by the host organisms or homologously expressed by their natural host cells.

The xylanase of the present invention is a 1,4-β-D-xylan xylanhydrolase, designated as EC 3.2.1.8 (endoxylanase). This xylanase is synthesized as a larger "precursor protein" (SEQ ID NO:1) consisting of a "presequence" (SEQ ID NO:25) and a "mature" protein sequence (SEQ ID NO:24). The amino acid sequence of the xylanase of the present invention, including the presequence thereof can be seen by reference to FIGS. 1a and 1b.

As used herein, the terms "precursor protein", "precursor enzyme" or "precursor xylanase", what is referred to is the entire protein, enzyme or xylanase, including all "pre" (and/or "pro") sequences, as transcribed and translated and before any post-translational modifications thereof.

As used herein the terms "mature protein", "mature enzyme" and/or "mature xylanase", what is referred to is that portion of the protein, enzyme or xylanase which, after post-translational modifications thereto, is secreted into and found in the culture broth.

As used herein, the term "presequence" what is referred to is that portion of the protein, enzyme or xylanase which is not secreted extracellularly, being removed (by enzymatic cleaving or otherwise) from the "mature" sequence before the extracellular excretion of the "mature" portion.

The isolated and purified xylanase of the present invention has been extensively characterized herein, as will be discussed at length below, as being an enzyme having a "mature sequence" of 200 amino acids. As determined from its amino acid sequence (which has been deduced from the nucleotide sequence of the structural gene coding therefor), the xylanase has a molecular weight of 22,534.55 kilodaltons (kDa) (as compared to a molecular weight of 26 kDa, as determined by SDS-PAGE analysis) and a pI of 9.56 (as compared to a pI of 9.8–9.9, as determined by isoelectric focusing). The xylanase of the present invention exhibits an effective xylanolytic activity over a broad temperature range of from below 40° C. to above 65° C., with an optimum temperature of 55° C. The optimum pH determined for this xylanase under assay conditions is 6.5–7.0, a range which one would expect to be too low to be efficient for use in biobleaching.

However, as will be discussed at length below surprisingly, despite the low optimum pH exhibited by the xylanase of the present invention under assay conditions, it is nonetheless efficient for facilitating the delignification of pulps having an alkaline pH over the entire pH range of 7.0 to 9.5.

This xylanase is devoid of any residual cellulase activity.

The xylanase of the present invention may be homologously expressed and extracellularly secreted into the culture broth by *Bacillus pumilus* PRL B12. This xylanase may also be heterologously-expressed and extracellularly-excreted into the culture broth by other Bacillus hosts, such as strains of *B. licheniformis, B. subtilis, B. alkalophilus, B. lentus* and *B. amyloliquefaciens* which have been transformed with the appropriate xylanase gene(s) from *B. pumilus* PRL B12 using rDNA techniques. Regardless of which approach is taken, the xylanases from these two different hosts have identical or partially identical immunochemical properties as can be determined immunologically by various well-known cross-reaction identity tests. (See Axelsen, N. H., Handbook of Immunoprecipitation-in-Gel Techniques, Blackwell Scientific Publications (1983), chapters 5 and 14).

The xylanase of the present invention is producible by the cultivation of *Bacillus pumilus* PRL B12 and mutants and variants thereof.

As used herein, the term "mutants and variants", when referring to B. pumilus PRL B12 refers to cells obtained by the alteration of the DNA nucleotide sequence of the structural gene coding for the xylanase thereof.

Xylanase-producing B. pumilus PRL B12 can be cultivated under aerobic conditions in nutrient medium containing assimilable carbon and nitrogen together with other essential nutrient(s). The medium can be composed in accordance with principles well-known in the art. Furthermore, it is noted that B. pumilus PRL B12 is not thermophilic.

During cultivation, the host cells secrete xylanase extracellularly. This permits the isolation and purification (recovery) of the xylanases to be achieved by, for example, separation of cell mass from a culture broth (e.g. by filtration or centrifugation) while avoiding lysis. The resulting cell-free culture broth can be used as such or, if desired, may first be concentrated (e.g. by evaporation or ultrafiltration). If desired, the xylanase can then be separated from the cell-free broth and purified to the desired degree by conventional methods, e.g. by column chromatography, or even crystallized.

Preferably, the xylanase of the present invention is isolated and purified from the xylanase-culture broth into which it is extracellularly secreted by : (1) concentration of the supernatant of the host culture; (2) passing the concentrated supernatant over an ion-exchange column; and (3) passing the concentrated supernatant over a hydrophobic interaction column.

The xylanase is also obtainable with the use of recombinant DNA technology methods well-known to those skilled in the art, such as by isolating a DNA fragment encoding the xylanase; combining the DNA fragment with an appropriate expression signal in an appropriate plasmid vector; introducing the plasmid vector in an appropriate host (either as an autonomously replicating plasmid or integrated into the chromosome); cultivating the host organism under conditions leading to expression of the xylanase; and recovering the xylanase from the culture broth.

The xylanases also may be produced essentially as described in Japanese Patent Specification No. 86039036 and/or in International Publication No. WO 92/03540.

The xylanase of the present invention may be used to supplement various lignocellulosic pulp bleaching sequences. Such bleaching sequences are employed after chemical-cooking of the pulp to obtain further delignification and bleaching in order to obtain the final brightness desired. Such bleaching sequences commonly have a first delignification stage, wherein a chemical-treatment step is performed followed by an alkaline extraction step. This delignification stage is then followed by a series of bleaching stages.

Classical (or conventional) bleaching sequences use elemental chlorine ($Cl_2$) alone or in addition to chlorine dioxide ($ClO_2$) to chemically-treat (by chlorination) the cooked pulp (followed by alkaline extraction) in the delignification stage. Elemental Chlorine Free (ECF) bleaching sequences use $ClO_2$ in place of $Cl_2$ in the delignification stage.

While exhibiting reduced AOX levels, such ECF sequences nonetheless still result in some AOX production. Further, $ClO_2$ is more expensive than $Cl_2$. Finally, chlorine dioxide is not as efficient in chemically-treating the cooked pulp as chlorine. Thus, higher quantities of $ClO_2$ are needed (in comparison to $Cl_2$) to achieve the same results. Use of such higher $ClO_2$ concentrations increases the production of AOX compounds that are associated therewith, as well as increasing the costs of the overall process. Indeed, in industrial applications the amount of $ClO_2$ needed for such bleaching can mandate a substantial investment in equipment, such as an "on-site" $ClO_2$ generator.

In Totally Chlorine Free (TCF) bleaching sequences, other sources of reactive oxidants, such as peroxides (i.e., hydrogen peroxide) and ozone, are used for chemically-treating the pulp in the delignification stage in place of elemental chlorine and chlorine dioxide. While achieving desired reductions in AOX levels, such TCF sequences may not achieve as high a level of delignification as desired. Furthermore, such reactive oxidants can cause degradation of the pulp. Finally, the reactive oxidants used in such TCF sequences can be quite expensive, further increasing the costs associated with such biobleaching sequences.

As will be discussed at length below, we have found that when used in conjunction with ECF and Classical sequences, pretreatment of pulp with the xylanase of the present invention surprisingly permits substantial reductions in the levels of the chlorine and/or chlorine dioxide charge needed during the subsequent delignification stage. A direct consequence of this is a reduction of the AOX concentration in the plant's effluents, resulting in a benefit to the environment. We have further found that a xylanase pretreatment aids ECF and classical sequences, as well as TCF sequences to achieve as high a final brightness as possible (as, for example, measured by the °ISO of the pulp).

The invention is particularly directed at pulps which have undergone a chemical-cooking. After cooking, xylan (after losing its side chains) precipitates back into the fiber structure of the pulp, where it protects the lignin that remains in the fibers. We believe that the xylanase of the present invention removes a part of that reprecipitated xylan, exposing the lignin and facilitating its subsequent removal during the delignification stage of the bleaching sequence. All types of lignocellulosic materials, such as wood, used for the production of chemical pulps are suitable for use with the process of the present invention. These pulps include, in particular, those used for kraft pulps, namely,the coniferous (soft) woods such as, for example, the various species of pines and firs and the deciduous (hard) woods, such as for example beech, oak, eucalyptus and hornbeam, as well as other sources of lignocellulosic materials, such as flax and jute.

As used herein, "Kappa Index" refers to a measurement of the amount of lignin present in wood pulp. The Kappa Index is a number representing the volume (in milliliters) of 0.1 N potassium permanganate ($KMnO_4$) solution consumed by one gram of moisture-free pulp under the conditions specified in, and following the procedures described in, TAPPI (Technical Committee of the Association of the Pulp and Paper Industry) Standard #T236cm-85 (1985).

As used herein, "°ISO" refers to a measurement of the brightness of the paper produced from the pulp. This value is a factor of the reflectability of the paper made from the pulp under the conditions specified in, and following the procedures described in, ISO (the International Organization for Standardization) Standard #2469, as published in reference #ISO 2470-1977(F), as supplemented by Standard #2470.

As used herein, the term "Multiple", "Chlorine multiple" and/or "Active Chlorine Multiple" represents the oxidizing power of the chlorine and chlorine dioxide, expressed as chlorine equivalents and calculated as $[Cl_2+CO_2 (2.63)$ % on oven-dried pulp (o.d.p.)]/kappa number of the unbleached pulp.

As used herein, the term "XU" refers to Xylanase Units, a figure arrived at as described below in Example 2.

The xylanase can be added at various points throughout the various bleaching processes. Preferably, xylanase is added to the pulp after the chemical-cooking thereof, but before the chemical-treatment step of the delignification stage of the bleaching sequence occurs. In this respect, the xylanase provides a kind of pretreatment which permits a reduction in the quantities of chlorine, chlorine dioxide and/or other reactive oxidants which need to be used in the chemical-treatment step of the delignification stage of,the bleaching sequence. Xylanase can be added in either its purified form, or it may be in a concentrated or unconcentrated culture broth.

Classical pulp bleaching sequences employ elemental chlorine ($Cl_2$) optionally with chlorine dioxide ($ClO_2$) for the delignification stage thereof. Common examples of classical bleaching sequences are: CEDPD (Chlorine chemical-treatment, alkaline Extraction, Dioxide, Peroxidase and Dioxide) and C/DEDPD (Chlorine/Dioxide chemical-treatment, alkaline Extraction, Dioxide, Peroxide and Dioxide). In each of these classical sequences, delignification substantially occurs in the first two steps, which are referred to herein as the "delignification stage" of the bleaching sequence. Bleaching is what substantially occurs in the remaining steps, which are referred to herein as the "bleaching stage" of the bleaching sequence.

Use of the Xylanase (X) of the present invention in classical bleaching sequences is, preferably, as a pretreatment of the pulp in a separate step immediately preceeding the chemical-treatment step of the delignification stage. It may be done without a washing therebetween. Used in this fashion, the *B. pumilus* PRL B12 xylanase permits substantial reductions, in the range of approximately 15% (for softwoods) to 40% (for hardwoods), in the quantity of chlorine that is needed to be utilized in the delignification stage. This reduction in chlorine is achieved while still maintaining a pulp having an acceptable level of delignification (as measured by the kappa index of the pulp having a particular pH at the time of the xylanase treatment).

ECF pulp bleaching sequences employ chlorine dioxide for the delignification and for the bleaching of pulp. A common example of an ECF sequence is: DPDPD (Dioxide chemical-treatment, Peroxide, Dioxide, Peroxide and Dioxide). In these ECF sequences, delignification substantially occurs in the first two steps, which are referred to herein as the "delignification stage" of the bleaching sequence. Bleaching is what substantially occurs in the remaining steps, which are referred to herein as the "bleaching stage" of the bleaching sequence.

Use of the Xylanase (X) of the present invention in such ECF bleaching sequences is, preferably, as a pretreatment of the pulp as a separate step immediately preceeding the chemical-treatment step of the delignification stage and without a washing therebetween. Used in this fashion, the *B. pumilus* PRL B12 xylanase permits a substantial reductions in the quantity of chlorine dioxide that is needed to be utilized in the delignification stage. This reduction is achieved while actually improving the delignification achieved in the delignification stage.

TCF pulp bleaching sequences employ a reactive oxidant, in the absence of $Cl_2$ and/or $ClO_2$, for delignification and bleaching phases thereof. A common example of a TCF sequence is: OQPZP (Oxygen, seQuestrant, Peroxide, ozone and Peroxide). In such sequences, the goal is to reduce, as much as possible, the quantity of ozone (or other reactive oxidant) in the fourth step while obtaining as high a final brightness of the wood pulp as possible (as measured by the final °ISO of the pulp). This reduction of ozone is important in that ozone can degrade the pulp.

Use of the Xylanase (X) of the present invention in such TCF bleaching sequences is, preferably, performed in conjunction with the sequestrant step (such that the sequence is OX/QPZP). Used in this fashion, the *B. pumilus* PRL B12 xylanase permits reductions in the quantity of ozone that is needed to be utilized in the sequence. This reduction was achieved while improving the final brightness achieved (as measured by the final °ISO of the pulp).

In another aspect of the present invention, the gene coding for the xylanase of the present invention has been isolated and purified, as described herein. The nucleotide sequence coding for the xylanase may be isolated from the chromosomal DNA of *Bacillus pumilus* PRL B12 by conventional cloning methods. The xylanase coding sequence may be obtained on a partial Sau3AI DNA fragment of 1022 base pairs (bp). The nucleotide sequence of this fragment has been determined, as is seen with reference to FIGS. 1*a* and 1*b* (SEQ. ID NO:1), wherein "N" represents an unidentified nucleotide. This 1022 bp fragment includes the nucleotide sequence coding (SEQ ID NO:26) for the mature xylanase and/or the nucleotide sequence (SEQ ID NO:27) coding for the xylanase presequence (SEQ ID NO:33) and/or the upstream coding sequences (SEQ ID NO:28) and/or the downstream nucleotide sequences (SEQ ID NO:29) of the xylanase gene of the present invention.

In still another aspect, the present invention includes expression vectors which contain nucleotide sequence(s) (structural gene) that code for a particular protein or protein(s), such as xylanases, a-amylases, pullulanases and alkaline proteases, and which expression vectors may be used for the transformation of suitable host cells in order to obtain the expression of the protein(s) coded for thereby.

As used herein, the term "Expression Vector" refers to any discrete DNA sequence which includes a replicon as well as other regions of DNA (nucleotide sequences), so as to independently function in host as a complete gene expression unit.

By the term "complete gene expression unit" what is meant is a structural gene and the promoter region(s) and regulatory region(s) required for transcription and translation.

By the term "promoter region" what is meant is any region upstream of a structural gene's coding sequence which permits binding of RNA polymerase and transcription and/or translation of the coding sequence to occur.

By the term "regulatory region" what is meant is any region which regulates transcription and/or translation of the structural gene.

By the term "structural gene" what is meant is a coding sequence which serves to be the template for the synthesis of RNA and which allows the synthesis of the protein of interest in a host therefor.

Depending upon the specifics of the case, the nucleotide sequence(s) of the expression vectors can include the nucleotide sequence(s) which code(s) for either precursor protein(s) or mature protein(s).

In addition to the sequence(s) discussed above, the expression vectors of the present invention may include further nucleotide sequences which aid in the maintenance of the expression vector and/or which aid in the expression and/or secretion of the protein(s) to be produced by the protein coding sequence(s). Such additional sequences may be either independent from the protein coding sequence(s), or they may be operably linked thereto.

By the term "independent from the protein coding sequence(s)" what is meant is that the synthesis, expression and/or secretion of the protein(s) coded for by the protein coding sequence(s) of the expression vector neither regulates, promotes nor otherwise controls or effects the said additional nucleotide sequence(s).

By the term "operably linked to the protein coding sequence(s)" what is meant is that the synthesis, expression and/or secretion of the protein(s) coded for by the protein coding sequence of the expression vector regulates, promotes and/or otherwise controls or effects the said additional nucleotide sequence(s) which are so associated (operably linked) therewith.

The expression vectors of the present invention may be constructed from nucleotide sequence(s) that are either homologous or heterologous to the host cells which they transform (or are intended to transform).

By the term "homologous to the host cells", what is meant is that the nucleotides sequence(s) of the expression vector are either derived from the host strain, or a strain belonging to the same species, (which they are intended to transform) or are modified or synthetically created, such that they function equivalently to nucleotides of the host strain (the expression host).

By the term "heterologous to the host cells", what is meant is that the nucleotide sequence(s) of the expression vector are derived from a strain which is different from the host strain (which they are intended to transform) nor modified or synthetically created, such that they function equivalently to nucleotides of the host strain (the expression host).

The expression vectors of the present invention may be constructed from nucleotide sequence(s) that are either homologous or heterologous to one another.

By the term "nucleotide sequence(s) that are homologous" what is meant are nucleotides sequence(s) (of the expression vectors) that are either derived from the same source organism and/or are modified or synthetically created, such that they function equivalently to nucleotides of the same source organism.

By the term "nucleotide sequence(s) that are heterologous" what is meant are nucleotide sequences(s) (of the expression vectors) that are derived from different source organisms and/or are modified or synthetically created, such that they do not function equivalently to nucleotides of the same source organism.

By the term "isolated" what is meant is that the nucleotides referred to (such as those of the expression vector) are not present in their naturally-occurring environment.

The nucleotide sequence(s) of the expression vectors of the present invention are prepared by restriction of DNA to prepare DNA fragments and by ligation of such DNA fragments to prepare recombinant molecules.

By the term "DNA fragment(s)", what is meant is one or more DNA nucleotides which are bonded to one another after having been subjected to restriction with a restriction enzyme. The nucleotides of such fragments may be either heterologous or homologous to one another.

By the term "recombinant molecule(s)", what is meant are at least two DNA nucleotides which are bonded to one another after having been subjected to ligation by a ligase (for example T4 DNA ligase). The nucleotides of such recombinant molecules may be either heterologous or homologous to one another.

Unless otherwise noted herein, such restriction of DNA to prepare DNA fragments used in the invention, ligation of such fragments to prepare recombinant molecules used in this invention, as well as introduction of DNA into host microorganisms or cells are carried out using known techniques disclosed in the various references cited herein. Also, unless otherwise stated, conditions are selected to avoid denaturation of the DNA and enzymes employed. For example, generally, the pH is buffered to remain in a range of neutrality and the temperature is generally kept below about 60° C. Preferably, restriction is generally carried out at about 37° C., except for some enzymes with are issued from thermophilic bacteria.

Restriction enzymes and ligases used in carrying out this invention are commercially available and should be used in accordance with the manufacturers instructions included therewith.

The various fragments and final constructions may be joined together in accordance with conventional techniques. In many cases, genes have been isolated and restriction mapped, as well as sequenced. To that extent, one is able to select the sequence of interest, such as the coding sequence for the protein of interest, by restriction of the gene. Further to that extent, one may employ further manipulation, as is necessary (such as by in vitro mutagenesis using synthetic oligonucleotides) in order to modify the DNA sequence and/or to provide a fragment of a particular size, including the desired sequence, and having the appropriate termini. Linkers and adapters can be used for joining sequences, as well as for replacing lost or deleted sequences, where the restriction site is internal to the region of interest. The various fragments which are isolated, may be purified by electrophoresis, electroeluted, ligated to other DNA fragments, cloned, reisolated and further manipulated, as desired.

The expression vectors of the present invention may be autonomously replicating vectors. That is to say, when transformed into a host organism, these vectors will be independently maintained (either as no copy, single copy or multicopy plasmids) without significant recombination or integration with the host's chromosomal DNA. Alternatively, these vectors may be of the type where the expression system becomes integrated chromosomally into the host.

Suitable expression vectors used in the practice of the present invention will, in general, be those which are compatible with the organism with which the vector will be transformed. In this regard, they will, for example, have compatible regulatory sequences and origins of replication. They will further, preferably, be multicopy and have selectable marker gene(s) (for example, gene(s) coding for antibiotic resistance). Examples of such suitable expression vectors include phages, plasmids, cosmids, transposons and chromosomal integration vectors. In addition, the expression vector of this invention may be used to integrate the expression elements and heterologous gene elements into the host chromosome following conventional techniques, such as are described in Saunders, et al., J. Bacteriol., 157, 718–726 (1984).

A preferred expression vector of the present invention include the nucleotide sequence (SEQ ID NO:26) that codes for the mature xylanase of *B. pumilus* PRL B12. These expression vectors may further include the nucleotide sequence coding for the presequence (SEQ ID NO:27) of the xylanase of *B. pumilus* PRL B12. These expression vectors may still further include various xylanase promoter and regulatory regions (sequences) (SEQ ID NO:28 and SEQ ID NO:29) of *B. pumilus* PRL B12 which influence/control the expression of the said xylanase. Expression vector pUB-BPX12 is such an expression vector.

It is noted here that, alternatively, other regulatory sequences (homologous or heterologous) can be used to control the expression of the xylanase gene.

Expression vector pUB-BPX12 includes the following elements (a) a fragment of vector pUB131 which carries the replication functions for Bacillus; and (b) the xylanase coding sequence from *B. pumilus* PRL B12. In this regard, it is noted that, as shall be discussed at length below in the Examples, the xylanase gene from *B. pumilus* PRL B12 was isolated by cloning in plasmid pUB131.

The vector pUB131 is an autonomously replicating multicopy plasmid which was constructed from (is a derivative of) the well-known plasmid pUB110. Plasmid pUB110 is well-characterized with its full DNA sequence known and its genes defined in McKenzie et al., Plasmid, 15:93–103 (1986).

pUB131 is constructed by, first, deleting a DNA sequence from pUB110, which encodes a polypeptide believed to be involved in mobilization functions. This deleted sequence is then replaced by a synthetic polylinker sequence, generating plasmid pUB131. The construction and sequence of vector (plasmid) pUB131 is reported in detail in (2).

The xylanase coding sequence, present on the 1022 bp partial Sau3AI fragment was subcloned into vector pUB131, thus generating expression vector pUB-BPX12. Most preferably, pUB-BPX12 contains the following elements:

1. a sequence from pUB131 responsible for autonomous replication of the plasmid in the host. (This feature permits pUB-BPX12 to be used in a number of Bacillus host species, such as strains of *B. subtilis, B. pumilus,* and *B. licheniformis, B. alkalophilus, B. lentus* and *B. amyloliquefaciens,* etc.);
2. a gene from pUB131 that confers resistance to kanamycin or neomycin to the host cells;
3. a gene from pUB131 that confers resistance to phleomycin to the host cells; and
4. the gene from encoding the xylanase from *B. pumilus* PRL B12.

Figure 4:
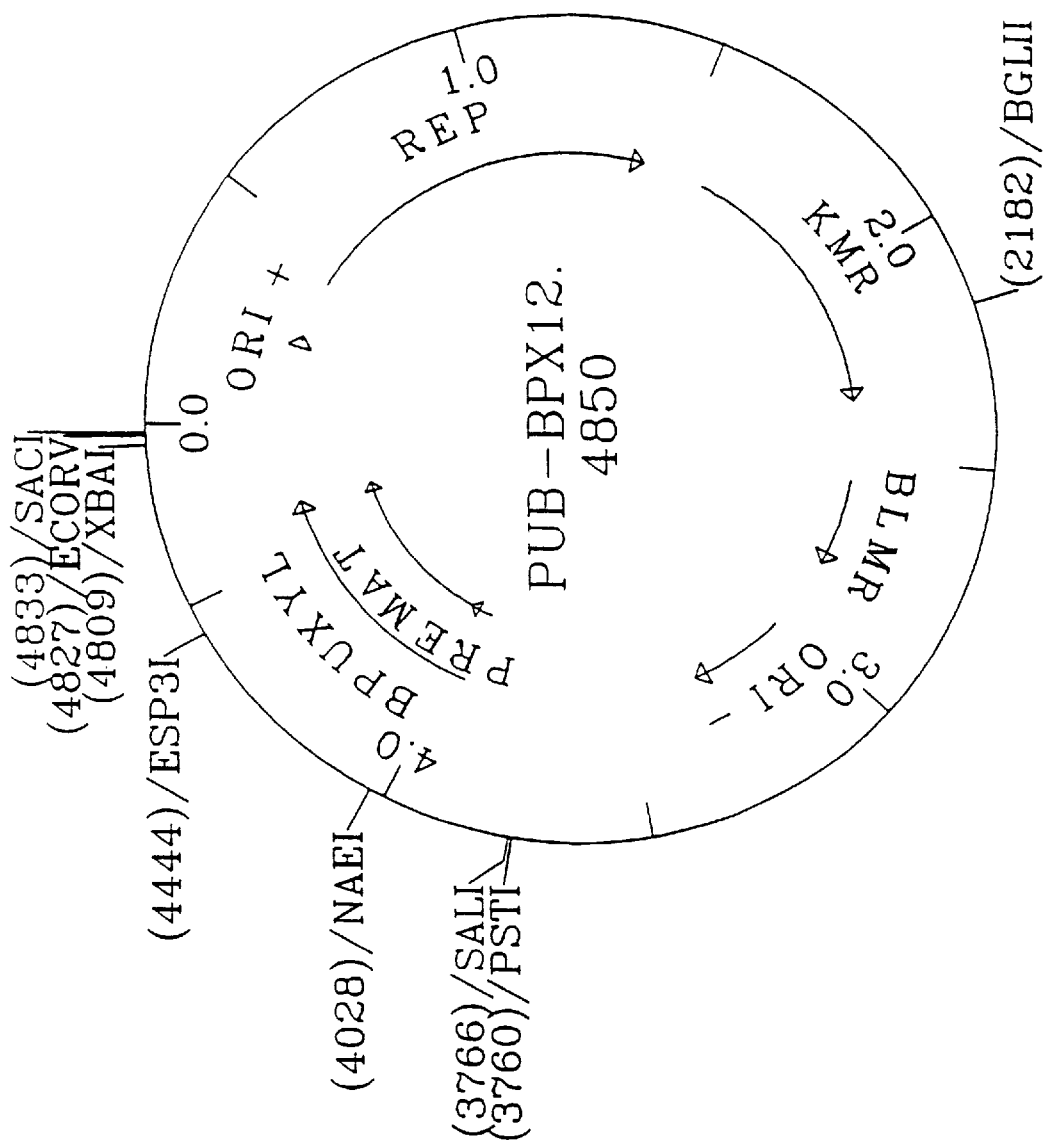
FIG. 4 is a restriction map of the plasmid pUB-BPX12.

A restriction map of plasmid pUB-BPX12 can be seen in FIG. 4.

Other expression vectors provided herein include the nucleotide sequence that codes for the pullulanase of *Bacillus deramificans* T 89.117D (pUBDEBRA1), or the nucleotide sequence that codes for the α-amylase of *B. licheniformis* ATCC 9789 (pL7TAKA), or the nucleotide sequence that codes for the alkaline protease of *B. licheniformis* SE2 (pLI1), or the subtilisin (alkaline protease) of *Bacillus subtilis* 168 (pKAC1 and pL7SBT). The expression hosts of the present invention are strains of the genus Bacillus which are compatible with the expression vector for the protein desired to be expressed thereby. Preferably, these strains are aerobic. It is further preferred that these strains not be thermophilic. Such strains include *B. subtilis, B. pumilus,* and *B. licheniformis, B. alkalophilus, B. lentus* and *B. amyloliquefaciens*. Preferably, the alkaline protease gene(s) thereof has (have) been deleted from these expression hosts.

The preferred host(s) of the present invention for the expression of the xylanase of the present invention are (biologically pure cultures of) recombinant strains derived from *Bacillus licheniformis*. As a species that is routinely used in the large-scale industrial production of extracellular enzymes, mainly proteases and alpha-amylases, it is an interesting host for the expression of cloned gene products on an industrial scale.

The particular recombinant strain of *B. licheniformis* used herein for host(s) for the expression vectors of the present invention is *B. licheniformis* SE2. *B. licheniformis* SE2 is asporogenic under production conditions. *B. licheniformis* SE2 is deficient in neutral protease production and is an alkaline protease producer.

The alkaline protease produced by *B. licheniformis* SE2 is first synthesized intracellularly as an inactive precursor called "pre-pro-enzyme". The "pre" and the "pro" sequences are eliminated during the translocation of the polypeptide into the extracellular culture medium, thus generating the secreted active alkaline protease.

In order to obtain the deleted SE2 strains (delap1, delap3 and delap6) therefrom, the: DNA coding sequence of the gene coding for at least the mature part of the alkaline protease was removed (as shall be discussed at length below) from the bacterial chromosome, thereby creating a deleted strain which is unable to produce a functional alkaline protease.

As used herein, the term "mature part of the alkaline protease" refers to the active alkaline protease, that is to say, the secreted alkaline protease polypeptide that is found in the culture broth.

In these host(s), *B. licheniformis* SE2 has been treated using rDNA techniques in order to obtain the (biologically pure cultures of) deleted strains of the present invention *B. licheniformis* SE2 delap1, SE2 delap3 and SE2 delap6, all of which do not produce alkaline proteases that may deleteriously degrade the heterologous protein expressed thereby before such heterologous protein can be recovered. Furthermore, the particular *B. licheniformis* SE2 delap recombinant strain may be transformed with pUB-BPX12, described above, which carries the xylanase coding sequence from *B. pumilus* PRL B12, as well as the genes coding resistance to kanamycin and neomycin.

The construction of the particular *B.licheniformis* SE2 delap strain involved the following steps:

1) The gene coding for the alkaline protease was isolated from the chromosomal DNA of *B. licheniformis* SE2 together with its flanking 5' and 3' regions, and then introduced into pUB131, a replicating plasmid in *B. subtilis;*
2) Deletion plasmids were constructed having the nucleotide sequence that codes for the mature part of the alkaline protease deleted therefrom;
3) *B. licheniformis* SE2 was then transformed with the resulting deletion plasmid;
4) The chromosomal protease gene from the *B. licheniformis* SE2 strain was then replaced by the deleted sequence of the plasmid through homologous recombination, generating a particular deleted *B. licheniformis* SE2 strain; and
5) The plasmid used for the deletion was eliminated from the deleted SE2 strains by curing.

The resulting deleted *B. licheniformis* SE2 delap strains thus differ from the parent SE2 strain only in that chromosomal deletions of the alkaline protease DNA sequence, including the DNA sequence coding for the mature protease has occurred. A schematic representation of the deletion is given in FIG. 10.

While described above with reference to *B. licheniformis* SE2, it is to be understood that the same strategy may be employed to prepare deleted strains of the other Bacillus strains (*B. subtilis, B. alkalophilus, B. lentus* and *B. amyloliquefaciens*) as is needed and desired.

MATERIALS AND METHODS

Materials

Unless otherwise specified in the following Examples (and in various of the preceeding Examples), the following materials were utilized therein:

Luria-Bertani ("L-B", sometimes referred to herein as L-B media) media is either, in a liquid form or in its solid form containing 15 g/l agar. The liquid L-B medium is that which is described in (3) at page A.1. The solid L-B medium is that which is described in (3) at page A.4.

The protease detection plates were made of L-B medium supplemented with 1% (w/v) Skim milk.

The composition and preparation of Tris-acetate (TAE) buffers and Tris-borate (TBE) buffers used herein are those which are described in (3) at 6.7.

The composition and preparation of the of TE buffers used herein are those which are described in (3) at page B.20.

AZCL-pullulan and AZCL-xylan were purchased from Megazyme Pty. Ltd.

The polyacrylamide sequencing gels were made according to the procedure described by (3) at pages 13.45–13.53, using 6% (w/v) acrylamide, instead of a gradient.

Acrylamide was purchased from Biozym.

DM3 medium was made according to the procedures described in (4) at pages 150–151.

Bacterial strains and plasmids were obtained from the sources, using the catalogue numbers as are set forth below in Table 1:

TABLE 1

Bacterial Strains and Plasmids Sources

| Strain or Plasmid | Origin | Catalog No. |
| --- | --- | --- |
| E. coli MC1061 | Clontech Laboratories[1] | C-1070-1 |
| E. coli JM109 | Clontech Laboratories[1] | C1005-1 |
| B. subtilis 168 | B.G.S.C.[2] | 1A1 |
| B. subtilis BR151 | B.G.S.C.[2] | 1A40 |
| B. subtilis PSL1 | B.G.S.C.[2] | 1A510 |
| B. subtilis 512 PN- | B.G.S.C.[2] | 1A274 |
| B. deramificans T 89.117D | B.C.C.M. (L.M.G.)[3] | P-13056 |
| B. licheniformis | A.T.C.C.[4] | 9789 |
| Bacillus pumilus PRL B12 | A.T.C.C.[4] | 6631 |
| pUB110 | B.G.S.C.[2] | 1E6 |
| pBR322 | Clontech Laboratories[1] | 6210-1 |
| pBS- | Stratagene[5] | 211202 |
| pUC18 | Clontech Laboratories[1] | 6110-1 |
| pACYC184 | Biolabs[6] | #401-M |
| pMK4 | B.G.S.C.[2] | 1E29 |

[1]Clontech Laboratories, (U.S.A.).
[2]B.G.S.C. is the collection of the BACILLUS GENETIC STOCK CENTER (Ohio State University) U.S.A.
[3]B.C.C.M. (L.M.G.) is the Belgian Coordinated Collections of Microorganisms (Laboratorium voor Microbiologie), University of Gent, Belgium.
[4]A.T.C.C. is the American Type Culture Collection, (U.S.A.).
[5]Stratagene, Inc. (U.S.A.).
[6]Biolabs New England. (U.S.A.).

Plasmids pUB131, pUBC131 and pUBC132 were constructed as described in European Patent Application No. 90116322.0.

*Bacillus licheniformis* SE2 was deposited under the provisions of the Budapest Treaty on Jun. 21, 1993, in the Belgian Coordinated Collections of Microorganisms, Laboratorium voor Microbiologie, K.L. Ledeganckstraat 35, B-9000 Gent, Belgium, under Accession Number LMG P-14034.

*Bacillus subtilis* SE3 was deposited under the provisions of the Budapest Treaty on Jun. 21, 1993, in the Belgian Coordinated Collections of Microorganisms, Laboratorium voor Microbiologie, K.L. Ledeganckstraat 35, B-9000 Gent, Belgium, under Accession Number LMG P-14035.

*Bacillus pumilus* PRL B12, (originally deposited in the American Type Culture Coillection (ATCC) in May 1938 under Accession Number 6631) was deposited under the provisions of the Budapest Treaty on Jun. 24, 1993 in the American Type Culture Collection (ATCC) 12301 Parklawn Drive, Rockville, Md. 20852, U.S.A., under Accession Number 55443.

Methods and Techniques

Unless otherwise specified in the following Examples, the following methods and techniques were utilized therein When the term "cloned", "subcloned" and/or "introduced" is used when speaking of DNA fragments, what is meant is, when necessary, the digestion (restriction) or donor and/or receptor DNA sequences, the treatment of cohesive protruding 3' and 5' ends thereof (when needed and/or desired), the separation of such fragments according to size and/or extraction of such fragments (when needed and/or desired), the dephosphorylization of such fragments, including linearized vectors (as needed and/or desired) and the ligation of such fragments to one another to form a recombinant DNA molecule. Such a definition further includes the transformation of host cells with such recombinant molecules, the selection of such transformants and the isolation and purification of recombinant DNA molecules (such as plasmids) from such host cells.

Digestions and restrictions of (donor and receptor) plasmids, chromosomal DNA and the like were performed using one or several restriction enzymes, as necessary, to isolate the DNA fragment of interest. The restriction enzymes used for such digestions are commercially available from a number of manufacturers. The restriction digestions were performed under the conditions specified in, and following the procedures described by (3) at 5.28–5.32, except that the restriction reaction was scaled up by a factor of 10, so as to obtain a sufficient amount of DNA for further purification steps.

Cohesive protruding 5' ends of fragments were made blunt by treatment with Klenow fragment of *E. coli* DNA polymerase I under the conditions specified in, and following the procedures described by (3) at F.2–F.3.

Cohesive protruding 3' ends of the fragment were made blunt by treatment with Bacteriophage T4 DNA polymerase, under the conditions specified in, and following the procedures described by (3) at F.4–F.5.

Separations of the DNA fragments according to size (after the restrictions were terminated) were performed by Agarose Gel Electrophoresis using 0.8% (w/v) agarose in a tris-acetate buffer, under the conditions specified in, and following the procedures described by (3) at 6.01–6.19. For separation of small fragments (<1000 bp), the agarose concentration used was increased to between 1 and 1.2% (w/v).

Other agarose gel electrophoresis were done under the conditions specified in, and following the procedures described in (3) at 6.9–6.15, using tris-acetate buffer (TAE) for preparative gels (DNA purification), or tris-borate (TBE) buffer for analytical purposes.

Following separation according to size, the DNA fragments of interest were extracted from, the agarose gel and, unless otherwise indicated therein, isolated and purified following either the filtration method using centrifugation, as described in Zhu, et al., Bio/Technology 3, 1014–1016 (1985), or the purification method using glass beads, provided under the tradename "Gene Clean" by Bio101.

Dephosphorylizations of the DNA fragments of interest, including linearized vectors, were performed under the conditions specified in, and following the procedures described by (3) at 1.60–1.61.

Ligations of DNA fragments, to the linearized vectors or otherwise, were performed as under the conditions specified in, and following the procedures described in (3) at 1.68–1.69. This method was used regardless if the fragments to be ligated contained cohesive or blunt ended termini. In this regard, it is noted that the ligase utilized herein was T4 DNA ligase.

Synthetic oligonucleotides were constructed following the procedure described in Beaucage, S. L., et al., (1981), Tetrahedron Letters 22:1859–1882 and using cyanoethyl phosphoramidites in a Biosearch Cyclone Synthesizer.

Labelling of synthetic oligonucleotides was performed by phosphorylation with [$\gamma$-$^{32}$P]ATP using Bacteriophage T4 polynucleotide kinase under the conditions specified in, and following the procedures described by (3) at page 11.31–11.33.

Clonings, subclonings, and/or introductions of double-stranded DNA linkers (used as donor DNA) into receptor vectors were achieved by assembling two complementary synthetic oligonucleotides, which were obtained in a phosphorylated form. Both oligonucleotides were mixed in 1×KGB buffer, described by (3) at 5.31, and heated at 95° C. for 10 minutes. The mixture was then permitted to slowly (over a minimum time of 15 minutes) cool down to room temperature. In this fashion, the double-stranded synthetic linkers were provided. These double-stranded synthetic linkers were then utilized as the donor DNA fragment either directly in ligations, as discussed above, or submitted to restriction digestion, as discussed above, before such ligation, as is desired and specified in the Examples.

DNA constructions were carried out by utilizing strains of E. coli as a cloning host. Alternatively, and when specified therein, strains of Bacillus subtilis were used as the cloning host.

Transformations of E. coli host cells were performed using the CaCl$_2$ method under the conditions specified in, and following procedures described by (3) at 1.82–1.84.

Alternative (and specified) transformations of E. coli host cells were performed using electroporation under the conditions specified in, and following the procedures described by (3) at 1.75–1.81.

The E. coli host cells used in the transformations were E. coli MC1061.

Transformations of B. subtilis host cells were performed using the Competent Cell Method under the conditions specified in, and following the procedures described by (5) at 9–11.

Alternative (and specified) transformations of B. subtilis host cells were performed using the Protoplast technique under the conditions specified in, and following the procedures described by (6) at 150–151, with the following modifications lysozyme powder was added at 5 mg/ml in SMMP, instead of 1 mg/ml as is specified in step 7 of the procedure described in (6) at page 151 (the incubation time needed to obtain a maximal lysis with lysozyme was 60 minutes); and the regeneration was done on DM3 medium supplemented with 200 $\mu$g/ml of Kanamycin.

The B. subtilis host cells used in the transformations were B. subtilis BR151.

Transformations of Bacillus licheniformis host cells were performed using the Protoplast technique under the conditions specified in, and following the procedures described by (6) at 150–151, with the following modification: lysozyme powder was added at 5 mg/ml in SMMP, instead of 1 mg/ml as is specified in step 7 of the procedure described in (6) at page 151. The incubation time needed to obtain a maximal lysis with lysozyme was 60 minutes.

Selection of E. coli transformants was carried out with the use of an appropriate antibiotic. For all plasmids derived from pBR322, pUC18, pUBC131, or pMK4, Ampicillin (100 $\mu$g/ml of culture medium) was used. For all plasmids derived from pACYC184, Tetracycline (12.5 $\mu$g/ml of culture medium) was used.

Selection of B. subtilis transformants was carried out on Luria and Bertani medium supplemented with the appropriate antibiotic. Kanamycin (25 $\mu$g/ml) was used for all plasmids derived from pUB110, pUB131 and pUBC131. Chloramphenicol (10 $\mu$g/ml) was used for all plasmids derived from pMK4.

Selection of B. licheniformis transformants was carried out with Phleomycin at 14 $\mu$g/ml (for pUB110 and pUB131 derivatives), and the regeneration time on DM3 plates [see (6) at page 150] was 3–4 days. The colonies appearing on the DM3 plates were transfered onto L-B plates containing the appropriate antibiotic for further work.

The isolation of plasmids from selected transformant colonies was performed by the colonies being grown in small scale cultures and then subjected to the alkaline lysis method, under the conditions specified in, and following the procedures decribed by (3) at 1.25–1.28. However, for transformant colonies of B. subtilis host cells, that procedure was modified in the following two aspects: (a) the glucose in the lysis buffer solution I described in (3) at 1.25 was replaced by 20% (w/v) sucrose, and lyzozyme (10 mg/ml) was freshly added; and (b) the lysis was carried out for 30 minutes at 37° C., before the addition of solution II.

Restriction analyses carried out on the small scale plasmid DNA preparations were performed under the conditions specified in, and following the procedures described by (3) at 1.85 and by (6) at 374–379. The relevant restriction enzymes used for the analysis are shown in the restriction maps given in the corresponding figures for each new plasmid construction.

In some cloning experiments, two orientations of the donor DNA fragment were expected, respective to the receptor plasmid. In such cases, in order to select the proper orientation of the fragments, a screening was carried out on the small scale plasmid DNA preparations by restriction analysis, under the conditions specified in, and following the procedures described by (3) at 1.25–1.28. The relevant restriction sites utilized in the screening are shown in the restriction maps given in the corresponding figures for each plasmid construction.

After having selected the desired plasmid(s) large scale preparations were carried out using the alkaline lysis method under the conditions specified in, and following the procedures described by (3) at 1.38–1.39, followed by a CsCl purification performed under the conditions specified in, and following the procedures described by (3) at 1.42–1.45.

Plasmids from E. coli were prepared and purified using the alkaline lysis method under the conditions specified in, and following the procedures described by (3) at 1.38–1.39, followed by a CsCl purification performed under the conditions specified in, and following the procedures described by (3) at 1.42–1.45.

Plasmids from B. subtilis and/or B. licheniformis were isolated, prepared and purified using the alkaline lysis method under the conditions specified in, and following the procedures described by (3) at 1.38–1.39, and modified in the two following points: (a) the glucose in the lysis buffer solution I described in (3) at 1.38 was replaced by 20% sucrose, and lyzozyme was freshly added at 10 mg/ml; and, (b) the lysis was carried out during 30 minutes at 37° C., before the addition of solution II. The plasmid was then purified by a CsCl purification under the conditions specified in, and following the procedures described by (3) at 1.42–1.45.

DNA extractions were from bacterial species which had been grown in L-B medium for 16 hours at 37° C.

Extractions and purifications of chromosomal DNA from cell cultures were obtained by centrifugation of the cultures while in the stationary phase, at 5000 rpm for 10 minutes. The resulting pellet was then suspended in 9 ml of 0.1M TRIS-HCl buffer (pH 8.0), 0.1M EDTA and 0.15M NaCl containing 18 mg of lysosyme. The resulting solution was then incubated for 15 minutes at 37° C. Following this incubation, the lysate was treated with 200 $\mu$l of an RNAase solution (10 mg/ml) for 20 minutes at 50° C. Thereafter, 1 ml of a 10% (w/v) SDS (sodium dodecyl sulfate) solution was added to the lysate and the mixture incubated at 70° C. for 30 minutes. The lysate was then cooled to about 45° C. before being added to 0.5 ml of a proteinase K solution (20 mg/ml) which had been prepared extemporaneously. The lysate was then incubated at 45° C. under occasional manual agitation until a transparent solution was obtained. Several phenol extractions were then performed on this transparent solution under the conditions specified in and following the procedures described by (3) at page E.3, until a well-defined interface (as described therein) was obtained. The extracted DNA was then precipitated by adding 20 ml of ethanol. The pellet was recovered by centrifugation at 5000 rpm for 5 minutes and dissolved in 2 ml of TE buffer (pH 8.0).

Cultures of E. coli, B. licheniformis and B. subtilis were grown in L-B medium, either liquid or solid.

"Platings" were performed by: (a) spreading the appropriate dilution of a liquid bacterial culture, essentially under the conditions specified in and following the procedures described by (6) at page 60, on a suitable agar containing medium 15% (w/v); and (b) growing the resulting plate at 37° C. for 18 hours, in order to obtain isolated colonies of said bacterium.

Isolations of single colonies were done under the conditions specified in, and following the procedures described by (6) at pages 58–60, and general conditions for growth and strain maintenance were performed following the conditions specified in, and following the procedures described by (6) at pages 61–62 and by (4) at pages 5–6.

By the term "transferred", what is referred to is the transferring of a bacterial colony from one culture medium (such as a petrie dish) to another, using standard inoculation techniques, which are well-known to those skilled in the art.

Large scale centrifugations (>100 ml) were carried out using a Beckman centrifuge equipped with a G2-21 rotor. The same centrifuge equipped with a JA-10 rotor was used for all centrifugations of 50–100 ml. Centrifugations of 3–49 ml were performed using this same centrifuge equipped with either a JA-20 or a JA-A rotor. Microcentrifugations (1–2 ml) were carried out using a Sigma 2K15 centrifuge.

Quantitations of DNA were performed following the spectrophotometric determination method as described by (3) at page E.5.

In vitro amplifications of DNA by the polymerase chain reaction (PCR) were carried out under the conditions specified in, and following the procedures described by (3) at 14.18–14.19, as well as the detailed protocols available in the PCR amplification Kits purchased from Biolabs.

Transfers of DNA fragments from agarose gels to nitrocellulose membranes (for Southern blotting experiments) were performed under the conditions specified in, and following the procedures described by (3) at page 9.38–9.39.

Southern Blotting Techniques were performed under the conditions specified in, and following the procedures described by (3) at page 9.31.

Hybridizations of radiolabeled probes to the DNA transfered to the nitrocellulose filters was done under the conditions specified in, and following the procedures described by (3) at 9.52–9.55.

Nucleotide sequencings were performed using the general chain termination dideoxy procedure under the conditions specified in, and following the procedures described by Sanger, et al., (1977) Proc. Natl. Acad. Sci. U.S.A., 74, 5463–5467, with the use of synthetic oligonucleotides serving as the primers for the DNA polymerase reactions.

Preparations of the dideoxy-mediated reactions using the T7 DNA polymerase were performed under the conditions specified in, and following the procedures described by the T7 sequencing Kit manual from Pharmacia LKB Biotechnology. The templates used for. the reactions were double-stranded plasmids isolated by large scale plasmid preparation using CsCl gradient centrifugation, as described above. The templates used in the sequencing reactions were denatured by treatment with NaOH as described in the T7 sequencing Kits.

Figure 13:
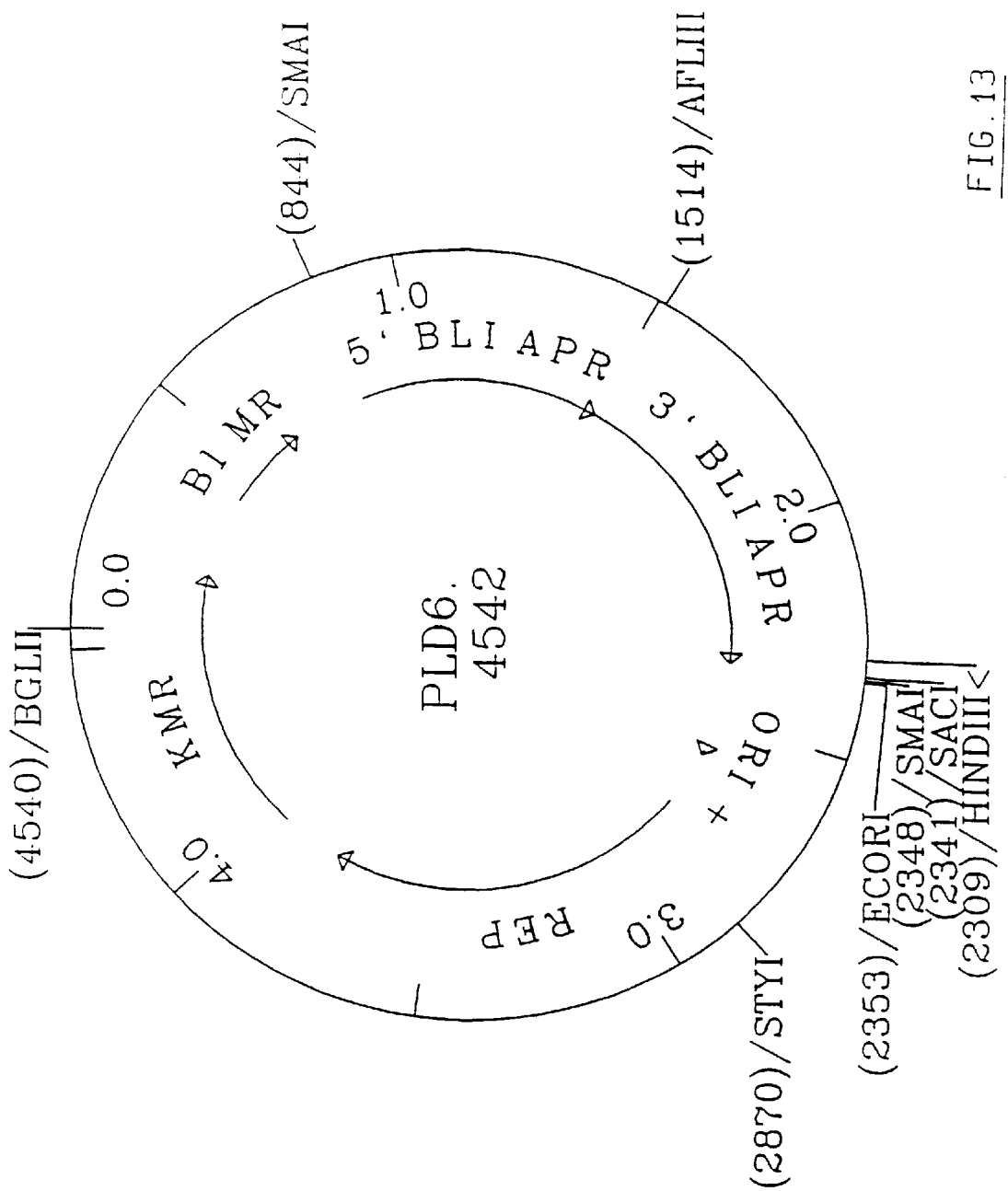
FIG. 13 is a restriction map of plasmid pLD6.

Sequencing strategies used were direct strategies using progressive oligonucleotides as is described by (3) at pages 13.15 and 13.17 (FIG. 13.3B).

Loading and running of the sequencing gels, as well as submitting them to autoradiography and reading, were performed under the conditions specified in, and following the procedures described by (3) at page 13.54–13.58.

Site-directed mutageneses were carried out under the conditions specified in, and following the procedures described by Kunkel T. A., (1985) Proc. Natl. Acad. Sci., U.S.A., 82:488–492 as well as by (3) at page 15.74–15.79. The mutageneses were performed using the muta-gene phagemid in vitro mutagenesis Kit purchased from Bio-Rad (No. 170-3576). The procedure consists of an elongation of a mutagenic synthetic oligonucleotide using, as a template, a single-stranded uracylated DNA, which is synthetized from the phagemid vector.

Determinations of the quantity of secreted proteins corresponding to given enzymes were performed by submitting the culture supernatant to polyacrylamide gel electrophoresis (PAGE) analysis in the presence of sodium dodecyl sulfate (SDS) in order to separate the various polypeptide components, as follows : A sample of 1 ml of the culture supernatant was precipitated by addition of 7% (w/v) trichloroacetic acid (TCA), and incubated for 1 hour at 0° C. The precipitated proteins were then collected by centrifugation at 15,000 RPM for 10 minutes, and the pellet was dissolved in 1 ml of sample buffer consisting in 10 mM Tris/HCl (pH 8.0), 1 mM EDTA, 2.5% (w/v) SDS, 5×(v/v) $\beta$-mercaptoethanol, and 0.001% (w/v) bromophenol blue. The resulting suspension was appropriately (see herebelow) diluted with the sample buffer and denatured at 98° C. for 15 minutes. Insoluble materials were then removed by centrifugation at 15000 RPM for 5 minutes. The resulting samples were then submitted to SDS-PAGE analysis using a Phast-System purchased from Pharmacia LKB Biotechnology, under the conditions specified in, and following the procedures described by Pharmacia in the Separation Technique File No. 110, using a 10–15% (w/v) polyacrylamide gradient. The gels were run for 60 Vh with a maximum voltage of 250 volts, a maximum power of 3 watts and a maximum intensity of 10 mA. After separation of the polypeptides, the gels were stained with Coomassie blue as described in the Development Technique File No. 200 from Pharmacia. The stained gels were then submitted to densitometry scanning using a lazer densitometer (XL) purchased from Pharmacia LKB Biotechnology. The amount of protein in the stained band which corresponded to the enzyme of interest, was determined by comparison with a Bovine serum albumin (BSA) standard, which was run in parallel. The bands exhibiting the following apparent molecular weights were considered for the various enzymes analyzed:

Xylanase: 26 kDa
Pullulanase: 110 kDa
Subtilisin 168: 28 kDa
Subtilisin Carlsberg: 28 kDa The dilutions of the supernatant samples which were submitted to PAGE/densitometry analysis were adjusted so that approximately the same peak area was measured for the samples and the BSA standard. Background values were substracted from each sample. The background values were estimated from control experiments consisting in analysing in parallel, a supernatant from the corresponding host bearing the control vector pUB131, instead of the expression vector.

Dilutions, quantities, etc. which are expressed herein in terms of percentages are, unless otherwise specified, percentages given in terms of per cent weight per volume (w/v). As used herein, dilutions, quantities, etc., which are expressed in terms of % (v/v), refer to percentage in terms of volume per volume.

Temperatures referred to herein are given in degree centigrade (° C.).

The restriction enzyme sites which are identified by the restriction enzyme name followed by a number in brackets ([ ]) refer to the first nucleotide position, in the sequence of the plasmid (or fragment), by reference to the figures, which is recognized by the restriction enzyme.

Deductions of the amino acid distribution, molecular weight and pI were all performed with the use of IntelliGenetics Suite software for Molecular Biology (Release #5.4) by IntelliGenetics, Inc., U.S.A.

The given sizes of DNA fragments obtained by restriction digestions is defined by the difference between the two nucleotide positions corresponding to the restriction sites.

Having thus described various methods to produce and obtain the xylanase of the present invention from various hosts, methods for the isolation and purification of the xylanase gene, the construction of expression vectors and expression hosts for expressing the xylanase and the use of the xylanase as an enzymatic pretreatment for the biobleaching of pulps (and, in particular wood pulps), the following examples are now presented for the purposes of illustration only and are neither meant to be, nor should they be read as being restrictive.

EXAMPLE 1

Production of *Bacillus Pumilus* PRL B12 Xylanase

A culture of *Bacillus pumilus* PRL B12 was obtained from the American Type Culture Collection, Rockville, Md., U.S.A., under accession number ATCC 55443.

A culture of *Bacillus licheniformis* SE2 delap1 was obtained in the manner described below in Example 28.

An agar medium was prepared comprising 1000 ml of Luria and Bertani medium and 0.5 grams of AZCL-xylan.

Starting from a frozen cellular suspension of each of the cultures, two sterile inoculation flasks (flask A and flask B) containing the agar culture medium were inoculated by streaking, each with one of the respective suspensions. In this manner, flask A was inoculated with the *B. pumilus* PRL B12 while flask B was inoculated with the *B. licheniformis* SE2 delap1. The inoculated flasks were then incubated for twenty-fours (24) hours, flask A at 30° C. and flask B at 37° C., so that respective cultures of the *B. pumilus* and the *B. licheniformis* strains were obtained therein.

A preculture medium was prepared comprised of: 5 grams Bacto-Peptone; 5 grams yeast extract; 5 grams glucose; and 1000 ml of phosphate buffer (50 mM, pH 7.0). The preculture medium was then sterilized.

A pair of sterile 250 ml Erlenmeyer Flasks (Preculture Flask #1 and Preculture Flask #2) were each filled with fifty (50) ml of the preculture medium. Preculture Flask #1 was then inoculated with the *B. pumilus* PRL B12 from the culture of flask A. Similarily, Preculture Flask #2 was inoculated with the *B. licheniformis* SE2 delap1 from the culture of flask B. These two preculture flasks were then incubated at 30° C. for 16 to 24 hours (with twenty-four hours being preferable) under agitation (orbital movement of 250 revolutions per minute with approximately 2.54 cm amplitude). At the end of incubation, the presence of a culture of the *B. pumilus* PRL B12 strain was visually observed in Preculture Flask #1 and the presence of a culture of the *B. licheniformis* SE2 delap1 strain was visually observed in Preculture Flask #2. The identity of these cultures was confirmed by standard detection techniques.

The *B. licheniformis* SE2 delap1 strain was then transformed with the pUB-BPX12 expression vector for xylanase (which had been constructed as was described below in Example 17), to form *B. licheniformis* SE2 delap1 (pUB-BPX12) and respective transformants were selected, isolated and purified, as is described below in Example 29.

*B. pumilus* PRL B12 and *B. licheniformis* SE2 delap1 (pUB-BPX12) each grow best in different culture media. In addition, each of these strains will not grow satisfactorily in the culture medium in which the other strain grows best. Thus, two (2) different culture media (designated herein as "M1" and "M2") were prepared, as follows (1) M1 Culture Medium comprised of 60 grams of wheat bran; 13 grams of soluble corn germ extract; 1 gram of sodium chloride; and 1000 ml of deionized $H_2O$.

(2) M2 Culture Medium comprised of 30 grams of soya flour; 75 grams of soluble starch; 2 grams of sodium sulfate; 5 milligrams of magnesium chloride; 3 grams of $NaH_2PO_4$; 0.2 grams of $CaCl_2*H_2O$; and 1000 ml $H_2O$. The pH of the suspension is adjusted to 5.8 with 10N NaOH.

The M1 culture medium is a medium in which the *B. pumilus* PRL B12 strain grows well. The M2 culture medium is a medium in which the various *B. licheniformis* SE2 delap strains grow well.

The culture broths were then sterilized.

A pair of sterilized one liter agitation flasks, each of which is equipped with (four) bafflers (said flasks hereinafter being designated as Culture Flask #1 and Culture Flask #2), were then filled with the culture media, as follows : Culture Flask #1 was filled with 100 ml of the M1 culture medium; and Culture Flask #2 was filled with 100 ml of the M2 culture medium.

Culture Flask 41 was then inoculated from the culture of *B. pumilus* PRL B12 of Preculture Flask #1, and Culture Flask #2 was inoculated from the culture of *B. licheniformis* SE2 delap1 (pUB-BPX12) of Preculture Flask #2. In doing so, the culture medium in the culture flasks was inoculated with 1% (volume/volume) of the culture material in the Preculture Flasks. That is to say, Culture Flasks containing 100 ml of the culture medium are innoculated with 1 ml of culture material from the Preculture Flasks.

The Culture Flasks containing the M1 and M2 culture media were then incubated at 30° C. for 72 hours under agitation (orbital movement of 250 revolutions per minute with approximately 2.54 cm amplitude).

Incubation of the Culture Flasks, as outlined above, results in, inter alia, the extracellular production of xylanase. Such xylanase is secreted into the culture broths in the Culture Flasks #1 and 2. The presence of such xylanase in the culture broths was then tested for by specifically assaying the culture broths for xylanase enzymatic activity, as is set forth below in Example 2.

EXAMPLE 2

Assaying Culture Broth For Xylanase Activity

Determination of the xylanase activity in the culture broths was obtained by use of the XU (Xylanase Unit) method. In this method, the presence and measurement of xylanases in the culture broths is determined by assaying for the reducing sugars that are released from a xylan substrate (such as birch xylan) as a result of the xylanolytic activity of the xylanases in the respective culture broths. The determination (measure) of the concentration of reducing sugars liberated was carried out following the Somogyi-Nelson methods as described in J. Biol. Chem., 153 (1944) pp. 375–380 and J. Biol. Chem. 160 (1945) pp. 61–68.

Unless otherwise indicated, the buffers mentioned in this example were prepared according to the procedures described by Gomori, Method. Enzymol., Vol. 1, pps. 138–146. The Somogyi Reagent and the Nelson Reagent were prepared as is described in J. Biol. Chem., 153 (1944) pp. 375–380 and J. Biol. Chem. 160 (1945) pp. 61–68. The substrate was prepared by dissolving 20 grams of xylan (ROTH Atr. 7500) in one liter of a 50 mM glycerophosphate buffer (pH 6.0). This solution was then incubated for 10 minutes at 95° C. and manually agitated to obtain a homogenous xylan suspension.

Assays were performed on the B. pumilus PRL B12 culture broth in culture flask #1 (the M1 culture medium), and on the B. licheniformis SE2 delap1 (pUB-BPX12) culture broth in culture flask #2 (the M2 culture: medium) using 0.1 ml of substrate (preincubated to 50° C.) which had been heated before use, as described above. To this substrate, 0.1 ml of the respective culture broths having the xylanase (with an activity of between 0.2 and 0.6 XU/ml) therein (which had been preincubated to 50° C.) were added and the solutions mixed by manual shaking. The assay was then run for fifteen minutes at 50° C. The reaction was then stopped by adding to the mixture 0.3 ml of 0.5N NaOH.

Blanks were prepared for each dilution of the enzyme by adding 0.3 ml of 0.5N NaOH before the substrate.

Standards were prepared by replacing the 0.1 ml of culture broth having the xylanase therein with 0.1 ml of a series of glucose dilutions having concentrations of from 0 to 5.555 micromoles ($\mu$M) of glucose per ml of solution.

As used herein and throughout the remainder of the Examples herein, one XU (Xylanase Unit) is defined as being the amount of xylanase which, under the conditions of the assay, catalyzes the liberation of reducing sugars equivalent, in reducing power, to 1 micromole ($\mu$M) of glucose per minute.

The results of the above assays revealed an activity for the xylanase secreted into the culture broth (of Culture Flask #2) by B. licheniformis SE2 delap1 (pUB-BPX12) that was at least fifteen times higher than the activity for the xylanase secreted into the culture broth (of Culture Flask #1) by B. pumilus PRL B12.

EXAMPLE 3

Isolation and Purification of Xylanase from Culture Broth

The xylanase was isolated and purified from the culture broth by starting from respective 100 ml samples of culture mixture obtained from Culture Flasks #1 and #2, as noted above in Example 1.

Approximately 100 ml of the fermentation broth from each of the flasks #1 and #2 were placed in respective test flasks, #1 and #2. To each test flask, a respective quantity of filter aid and PERLITE F50 was added up to a concentration of 5.4% (weight/volume).

The fermentation broths in the test flasks were then paper filtered a using a Buchner filtration funnel. Approximately 38 ml of (liquid) filtrate was thus obtained from each filtration, as well as filter cakes. Each of the filter cakes was then washed with deionized water until respective final volumes of 100 ml of filtrate were obtained.

The filtrates obtained were then concentrated on an Amicon ultrafiltration cell (Series 800 stirred cell with an YM10 membrane having a 10 kD cutoff). The concentrate activity was then measured.

1 ml of each of these concentrated samples were then loaded on respective Sepharose Mono-Q HP 16/10 anion-exchange columns equilibrated with a 20 mM TRIS buffer (pH 8.0). The elution was carried out using a flow rate of 3 ml/min of a 20 mM tris(hydroxymethyl)amino-methane (TRIS) buffer (pH 8.0) of linearly increasing NaCl concentration of from 0 to 1 molar. This led to the elutions of the xylanase activity directly after the dead volume on the column into a volume of 15 ml. Respective fractions were then obtained.

1 ml of each of these fractions were then placed on respective Phenyl Sepharose 16/10 columns equilibrated with a 20 mM glycine buffer (pH 9.0), 1M $(NH_4)_2SO_4$. The elutions were carried out by means of a descendant gradient by ammonium sulfate into this same buffer, from 1M to 0m in ten (10) minutes, followed by an isocratic elution with a delivery of 5 ml/min. In each column, the xylanase activity was eluted in one fraction after 20 to 21 minutes. These purified, eluted fractions were found to be electrophoretically homogeneous.

EXAMPLE 4

Amino Acid Sequence

The amino acid sequence of the xylanase of the present invention was indirectly determined by deduction from the nucleotide sequence of the gene that encodes therefor (which gene was obtained and sequenced, as shall be discussed at length below in Example 17).

In order to determine the correct reading frame, the N-terminal sequences of the xylanase of the fractions obtained (as described above in Example 3) from both the B. pumilus strain and the B. licheniformis strain were determined following the protocol set forth in Vandekerkhove, J., et al., Eur. J. Biochemistry, 152, 9 (1985). These N-Terminal sequences were found to be identical, as follows:

SEQ ID NO: 2 Glu-Thr-Ile-Tyr-Asp-Asn-Arg-Ile-Gly-Thr-His-Ser-Gly-Tyr-Asp

Using the N-terminal sequences to determine the correct reading frame, we found that the precursor xylanase of the present invention is comprised of two hundred and twenty-seven (227) amino acids residues (see FIGS. 1a and 1b) SEQ ID NO:1. Twenty-seven (27) of these amino acids are in the "pre" sequence. The remaining two hundred (200) of these amino acids are the mature protein. This is the same whether this gene is homologously expressed by B. pumilus PRL B12 or heterologously expressed by a recombinant host that has been transformed therewith, such as the deleted B. licheniformis SE2 delap (pUB-BPX12) strains.

The amino acid sequence deduced for the xylanase of Bacillus pumilus PRL B12 (as seen in FIGS. 1a and 1b) is quite different from those deduced for the xylanases secreted by either B. pumilus IPO or B. pumilus DSM 6124.

EXAMPLE 5

Amino Acid Distribution

The amino acid distribution of the xylanase of the present invention was indirectly determined from the amino acid sequence of the xylanase (as was indirectly determined, as described above in Example 4).

Examination of the amino acid distribution of the 200 amino acids that comprise the "mature" xylanase protein reveals an enzyme which is rich in tyrosine, threonine and asparagine, as follows:

TABLE 2

Amino Acid Distribution of the "Mature" Xylanase

| Amino Acid | Quantity | Percentage of Molecular Weight |
| --- | --- | --- |
| Tyrosine | 16 | 11.6 |
| Threonine | 19 | 8.5 |
| Asparagine | 16 | 8.1 |
| Serine | 18 | 7.0 |
| Lysine | 11 | 6.3 |
| Glycine | 22 | 5.6 |
| Arginine | 8 | 5.4 |
| Phenylalanine | 8 | 5.2 |
| Glutamic Acid | 9 | 5.2 |
| Isoleucine | 10 | 5.0 |
| Leucine | 10 | 5.0 |
| Tryptophan | 6 | 5.0 |
| Aspartic Acid | 7 | 3.6 |
| Valine | 8 | 3.5 |
| Methionine | 6 | 3.5 |
| Glutamine | 6 | 3.4 |
| Alanine | 10 | 3.2 |
| Histidine | 4 | 2.4 |
| Proline | 5 | 2.2 |
| Cysteine | 1 | 0.5 |
| Aspartic Acid & Asparagine | 0 | 0.0 |
| Glutamine & Glutamic Acid | 0 | 0.0 |

Such an amino acid distribution is quite different from those reported for the xylanases produced by B. pumilus IPO and B. pumilus DSM 6124.

EXAMPLE 6

Molecular Weight Deduction From Amino Acid Distribution

The deduction of the molecular weight of the xylanase of the present invention was indirectly determined (calculated) from the amino acid distribution noted above in Table 2. This deduction gave the xylanase of the present invention a molecular weight of 22,534.55 Daltons (D).

EXAMPLE 7

Molecular Weight Determination by SDS-PAGE Analysis

Each of the samples used herein for determination of molecular weight were obtained from the purified fractions of Example 3.

An estimation of the molecular weights of the purified xylanase samples of the present invention by the use of SDS-PAGE analysis was effectuated in denaturing conditions on polyacrylamide gel using Pharmacia PhastGel 10–15% (w/v) and 20% (w/v) gels.

Pharmacia LMW markers were used for establishing the relation of molecular weight to migration distance. One vial diluted in 1.5 ml of the following buffer, which was also used for the samples : 10 mM TRIS (pH 8); 1 mM EDTA; 2.5% (w/v) SDS; 5% (v/v) beta-mercaptoethanol and 0.1% (w/v) bromophenol blue.

The samples were each precipitated with trichloroacetic acid before being diluted to a concentration of approximately 100 µg protein/ml (assay : modification of the Bradford Coomassie Blue Binding Assay, described by Read and Northcote, Analytical Biochem., 116:53–64) in the same buffer, noted above, as was used to dilute the markers. The diluted samples were then denatured at 98° C. for fifteen (15) minutes and 4 µl were deposited on the gels. The gels were run for 60 Vh with a maximum voltage of 250 volts, a maximum power of 3 watts and maximum intensity of 10 mA.

The results of this SDS-PAGE analysis can be seen by reference to the graph in FIG. 2, where the migration distance from the anode is plotted. In both cases (10–15% and 20% gels), the xylanase samples from the native B. pumilus PRL B12 strain and the recombinant B. licheniformis SE2 delap1 (pUB-BPX12) strain have exactly the same electrophoretic mobility. Furthermore, in both cases, the apparent molecular weight was found to be 26 kD.

EXAMPLE 8

Prediction of pI From Amino Acid Sequence

Prediction of the isoelectric point (pI) of the xylanase of the present invention from the amino acid sequence noted in FIGS. 1a and 1b. This deduction gave the xylanase of the present invention an isoelectric point of 9.56.

EXAMPLE 9

Determination of pI by Isoelectric Focusing Analysis

Each of the samples used herein for determination of isoelectric point (pI) were obtained from the purified fractions of Example 3.

This determination was effectuated by isoelectric focalization in polyacrylamide gels, by employing Pharmacia DryIEF Gels, that had been rehydrated with 2 ml of an ampholine solution (1 volume Pharmacia 8–10.5% (w/v) ampholine added to 15 volumes of deionized water), following the protocol recommended by the supplier.

A 4 µl aliquot of each of the enzyme dilutions in $H_2O$, containing approximately 100 µg of xylanase were deposited and loaded (200 V, 15 Vh) in the middle of the gels after the prefocusing had taken place (2000 V, 75 Vh). Pharmacia high pI markers were used as standards.

After focusing, gels were stained with Coomassie Blue following the protocol detailed in the Separation Technique File No. 101 (publication 18-1018-20, Pharmacia LKB Biotechnology).

Figure 3:
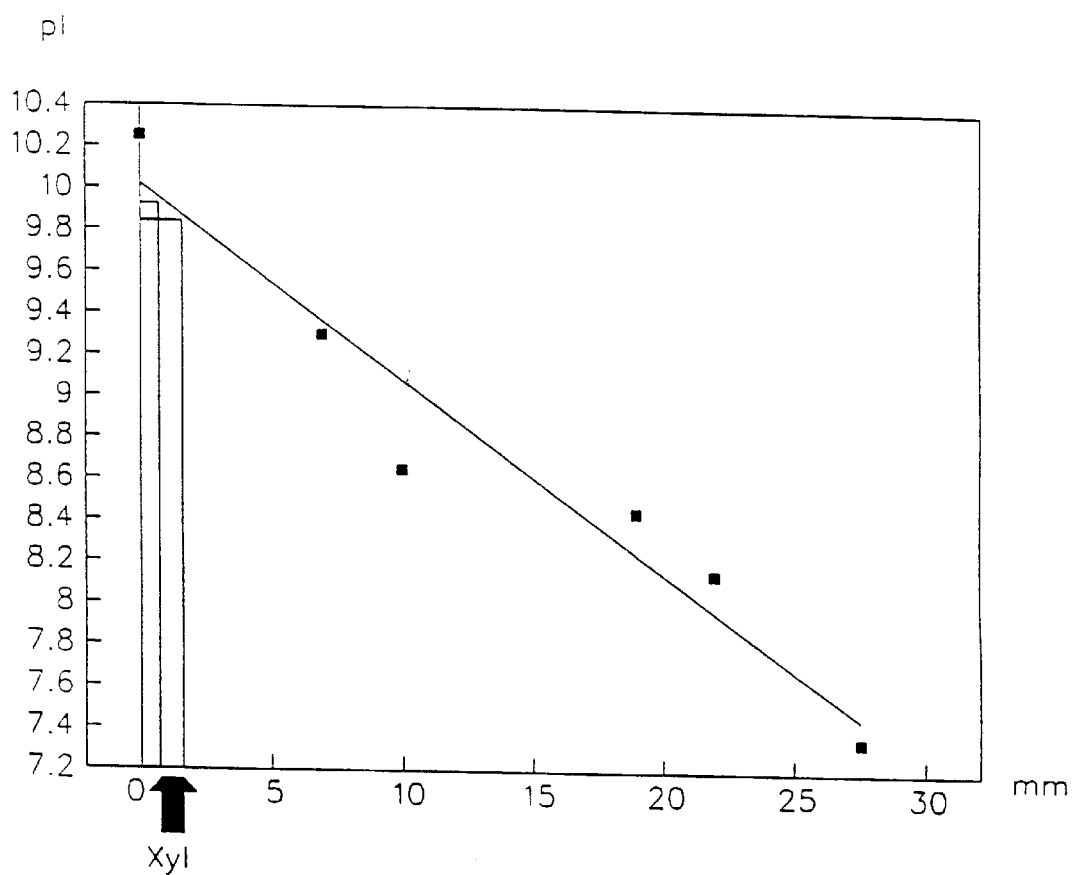
FIG. 3 is a graph illustrating the results of the PAGE analysis for determining the isoelectric point (pI) of the xylanase of the present invention in which the Y-axis represents the pI, the X-axis represents distance from cathode in millimeters (mm) and Xyl represents the pI obtained for the xylanase of the present invention.

Using this technique, the value of the isoelectric point of the xylanase secreted from *B. pumilus* PRL B12, as well as that xylanase secreted from *B. licheniformis* SE2 delap1 (pUB-BPX12) was determined to be from 9.8 to 9.9. Further, their behavior is the same. The results of this analysis can be seen by reference to FIG. 3.

EXAMPLE 10

Determination of Optimum Temperature for Xylan Hydrolysis

Each of the samples used herein for determination of optimum temperature were obtained from the purified fractions of Example 3.

Eighteen (18) samples, each of which contain a 1% (w/v) birchwood xylan substrate (Roth, Atr. 7500), were dissolved in 50 mM of glycerophosphate buffer (pH 6.5).

Assays on each of the samples were then performed with an incubation time of 15 minutes. These assays were conducted on pairs of samples at different temperature increments of 5° C. starting at 40° C. and finishing at 80° C. The amount of reducing sugars released gives an indication of the activity of the xylanase sample being assayed. The quantity of reducing sugars liberated was measured following the Somogyi-Nelson method as described in Example 2.

The results of these assays, given as percentages of the maximal activity, is given in Table 3, as follows

TABLE 3

Optimum Temperature Determination

| | % Maximum Activity | |
|---|---|---|
| Temperature (° C.) | Xylanase from *B. pumilus* PRL B12 | Xylanase from *B. licheniformis* SE2 delap1. |
| 40.0 | 54.4 | 51.2 |
| 45.0 | 62.2 | 62.4 |
| 50.0 | 81.5 | 81.4 |
| 55.0 | 100.0 | 100.0 |
| 60.0 | 94.0 | 84.7 |
| 65.0 | 79.7 | 81.3 |
| 70.0 | 32.5 | 31.1 |
| 75.0 | 20.5 | 24.4 |
| 80.0 | 12.2 | 11.4 |

Conducting the aforementioned tests gave results that show that the optimum temperature of the xylanase of the present invention is 55° C.

EXAMPLE 11

Determination of Range of Temperature Stability

Each of the samples used herein for determination of the range of temperature stability of the xylanase of the present invention were obtained from the purified fractions of Example 3 and prepared as described in Example 10.

Assays on each of the samples were then performed after the preincubation times (in minutes) and at the temperatures noted. below in Table 3. The activity of these samples was determined at 0, 10, 30, 60 and 120 minutes following the protocol set forth above in Example 2.

The results of these assays, given as percentages of the maximal activity, is given in Table 4, as follows:

Determination of Range of Temperature Stability

| | % Maximum Activity | | |
|---|---|---|---|
| Time (Minutes) | 50 ° C. | 60 ° C. | 70 ° C. |
| 0 | 100.0 | 100.0 | 100.0 |
| 10 | 111.0 | 80.0 | 0.0 |
| 30 | 113.0 | 68.0 | 0.0 |
| 60 | 119.0 | 52.0 | 0.0 |
| 120 | 110.0 | 40.0 | 0.0 |

Conducting the aforementioned tests gave results that show that, at 50° C., the xylanase of the present invention is fully stable for at least 120 minutes.

EXAMPLE 12

Determination of Optimum pH for Xylan Hydrolysis

Each of the samples used herein for determination of optimum pH were obtained from the purified fractions of Example 3, and prepared as described in Example 10.

Assays on each of the twenty-two samples (adjusted to the different pH values noted below in Table 5) were performed at 50° C. (the correction for pH/temperature relationship is negligible with this buffer) with an incubation time of 15 minutes following the protocol set forth above in Example 2. The amount of reducing sugars released gives an indication of the activity of the xylanase sample being assayed. The quantity of reducing sugars liberated was measured following the Somogyi-Nelson method as described in Example 2.

The results of these assays is given in Table 5, as follows:

Optimum pH Determination

| | % Maximum Activity | |
|---|---|---|
| pH | Xylanase from *B. pumilus* Strain | Xylanase from *B. licheniformis* Strain |
| 5.0 | 45.4 | 45.1 |
| 5.5 | 78.6 | 78.3 |
| 6.0 | 98.7 | 93.2 |
| 6.5 | 96.6 | 100.0 |
| 7.0 | 100.0 | 96.1 |
| 7.5 | 82.2 | 86.2 |
| 8.0 | 73.8 | 63.7 |
| 8.5 | 52.7 | 44.6 |
| 9.0 | 24.6 | 18.8 |
| 9.5 | 11.0 | 4.7 |
| 10.0 | 0.4 | 2.0 |

Conducting the aforementioned tests gave results that show that the optimum pH of the xylanase of the present invention is 6.5–7.0.

From all of the foregoing Examples, it is evident that the xylanase of the present invention is the same, regardless if it was expressed by the natural source thereof (*B. pumilus* PRL B12) or by the recombinant host, *B. licheniformis* SE2 delap1 (pUB-BPX12). It further appears that the xylanase of the present invention has an amino acid sequence and distribution that is different from those of other xylanases, even those xylanases produced by other strains of *B. pumilus*.

EXAMPLE 13

Effect of pH on the Efficacy of Xylanase Pretreatment

Eight suspensions of a softwood kraft pulp were prepared, each having an initial Kappa Index of 25.5 and a consistency (Con.) of 2.5%. Six of these suspensions were pretreated for two hours at 50° C. with 30 XU of the xylanase of the present invention per gram of dry pulp to be pretreated therewith. Two additional suspensions of the kraft wood pulp were subjected to the same conditions, but in the absence of any xylanase whatsoever. These pretreated kraft pulp samples were then, without intermediate washing, subjected to chlorination (C) by use of the weight of chlorine (given in terms of active chlorine multiples), specified below in Table 6A followed by an alkaline extraction (E).

Twenty-four suspensions of a hardwood kraft pulp were prepared having an initial Kappa Index of 13 and a consistancy of 2.5%. These suspensions were pretreated for two hours at 50° C. with 30 XU of the xylanase of the present invention per gram of dry pulp to be pretreated therewith. These pretreated kraft pulp samples were then, without intermediate washing, subjected to chlorination (C) at 22° C. for 1.0 hours and a consistency of about 3% followed by an alkaline extraction (E) at 60° C. for 1.5 hours and a consistency of 5% (see Table 6B).

The different treatment pH's were obtained by small additions of diluted acid (0.1N), such as sulfuric acid. The treatment at pH 9.5 substantially corresponds, in fact, to actual industrial situations wherein the pH is not regulated, the pulp being suspended in nonbuffered water (this test is marked in Table 6A by the asterisk).

The results of the pretreatments are set forth below in Tables 6A and 6B:

TABLE 6A

Effect of pH on Efficacy of Pretreatment with
B. pumilus PRL B12 Xylanase in Classical Bleaching Sequences
Softwood Kraft Pulps

| Initial pH | XU/g | Multiple | Kappa Index |
|---|---|---|---|
| 6.5 | 30 | 0.17 | 7.40 |
| 7.0 | 30 | 0.17 | 6.71 |
| 8.0 | 30 | 0.17 | 6.56 |
| 8.5 | 30 | 0.17 | 6.30 |
| 9.0 | 30 | 0.17 | 6.57 |
| 9.5* | 30 | 0.17 | 7.38 |
| 9.5 | 0 | 0.17 | 10.00 |
| 9.5 | 0 | 0.20 | 7.00 |

TABLE 6B

Effect of pH on Efficacy of Pretreatment with
B. pumilus PRL B12 Xylanase in Classical Bleaching Sequences
Hardwood Kraft Pulps

| | Kappa Index | | |
|---|---|---|---|
| Initial pH | 0 XU/g Multiple: 0.20 | 5 XU/g Multiple: 0.12 | 10 XU/g Multiple: 0.12 |
| 6.5 | 2.40 | 2.25 | 2.19 |
| 7.0 | 2.15 | 2.22 | 2.08 |
| 7.5 | 2.10 | 2.16 | 2.08 |
| 8.0 | 2.16 | 2.18 | 2.13 |
| 8.5 | 2.16 | 2.22 | 2.24 |
| 9.0 | 2.13 | 2.32 | 2.38 |
| 9.5 | 2.11 | 2.54 | 2.54 |
| 10.0 | 2.09 | 2.56 | 2.68 |

Surprisingly, (and in contrast to the results seen in Example 12 and Table 5, wherein when determined on a purified substrate the optimal pH is only about 7.0), as demonstrated herein, in biobleaching conditions, the optimum pH of the xylanase appears to be about 8.5 when softwoods are involved and about 7.5–8.0 when hardwoods, are involved.

Furthermore, and perhaps more surprisingly, it is noted that the xylanase of the present invention is efficient for facilitating the delignification of wood pulps having all pH's in the 7–9.5 range (the natural pH of this kraft pulp in a water suspension).

The obtained effects seen in Tables 6A and 6B are also significant in that the enzymatic treatment permits (in pH's of 6.5–9.5) a 15% reduction in the chlorine which is needed to be used for the chemical-treatment of softwoods in the delignification stage and a 40% reduction in the chlorine which is needed to be used for the chemical-treatment of hardwoods in the delignification stage.

EXAMPLE 14

Effect of Xylanase Concentration on the Efficacy of Xylanase Pretreatment

A Kraft hardwood pulp was pretreated with an oxygen treatment according to the process described at length in United States Letters Patent No. 4462864, so as to produce an oxygen-treated pulp having an initial Kappa Index of 12.3 and an initial °ISO of 33.4.

Six (6) suspensions (samples) were then prepared from the oxygen-treated pulp.

The operating conditions used were those which would be possible to utilize industrially (50° C. for one hour at a consistancy of 5%). The general scheme of the bleaching sequence (C/D)EDPD was thereafter performed with the pulp sample.

Two (2) of the samples (designated samples 1 and 2) were then selected as reference bleaching sequences and were effectuated by placing in operation one (1) dose of active chlorine equal to 0.2 times the Kappa Index during the course of the C/D step. This dose was then retaken in 80% gaseous chlorine and 20% in chlorine dioxide. Larger doses of chlorine dioxide were used for covering a realistic range of final whiteness.

The remaining four (4) samples were selected to be subjected to an enzymatic pretreatment that was realized by the use of either 8 (samples 3 and 4) or 13 (samples 5 and 6) Xylanase Units (XU) per gram of dry pulp. We note that the bleaching sequence immediately following the enzymatic pretreatment was performed without any intermediate washing. The active chlorine multiples used were from 0.16 to 0.14 (representing an economy of elemental chlorine—$ClO_2$ in the chlorination stage being kept constant—of, respectively, 25% and 38%). These reductions were obtained by reducing the dose of molecular chlorine, the dose of chlorine dioxide remaining the same.

The starting °ISO of these samples was 33.4. The starting Kappa Index was 12.3. Full details of operating conditions and the results of the various trials of this Example can be seen by reference to Table 7.

TABLE 7

Efficacy of *B. pumilus* PRL B12 Xylanase Pretreatment in Classsical Bleaching Sequences

| Sample | Step | Cl₂ | Reactants (g/100 g o.d.p.) NaOH | ClO₂ | H₂O₂ | Temp °C. | Time (Hr) | Con. (%) | pH Start | End | °ISO |
|---|---|---|---|---|---|---|---|---|---|---|---|
| 1–2 | X | — | — | — | — | — | — | — | — | — | — |
|  |  |  | 0 XU/g o.d.p. |  |  |  |  |  |  |  |  |
|  | C/D | 1.96 | — | 0.5 | — | 40 | 0.5 | 3 | 2.2 | 2.1 | — |
|  | E | — | 2.0 | — | — | 70 | 1.5 | 12 | 12.7 | 11.4 | 53.4 |
|  | Kappa Index: 2.6 |  |  |  |  |  |  |  |  |  |  |
| 1 | D | — | — | 0.6 | — | 75 | 3.0 | 12 | 5.6 | 4.4 | 75.8 |
|  | P | — | 0.6 | — | 0.2 | 70 | 1.5 | 12 | 12.0 | 10.7 | 81.5 |
|  | D | — | — | 0.3 | — | 85 | 2.5 | 12 | 5.5 | 4.8 | 88.0 |
| 2 | D | — | — | 0.9 | — | 75 | 3.0 | 12 | 5.5 | 3.6 | 77.4 |
|  | P | — | 0.6 | — | 0.2 | 70 | 1.5 | 12 | 12.0 | 10.6 | 82.4 |
|  | D | — | — | 0.3 | — | 85 | 2.5 | 12 | 6.0 | 4.9 | 89.0 |
| 3–4 | X | — | — | — | — | 50 | 1.0 | 5 | 7.0 | 7.0 | — |
|  |  |  | 8 XU/g o.d.p. |  |  |  |  |  |  |  |  |
|  | C/D | 1.22 | — | 0.5 | — | 40 | 0.5 | 3 | 3.0 | 3.0 | — |
|  | E | — | 2.0 | — | — | 70 | 1.5 | 12 | 12.5 | 11.6 | 54.3 |
|  | Kappa Index: 3.2 |  |  |  |  |  |  |  |  |  |  |
| 3 | D | — | — | 0.6 | — | 75 | 3.0 | 12 | 5.0 | 4.4 | 72.2 |
|  | P | — | 0.6 | — | 0.2 | 70 | 1.5 | 12 | 11.7 | 10.7 | 79.8 |
|  | D | — | — | 0.3 | — | 85 | 2.5 | 12 | 5.6 | 4.9 | 87.4 |
| 4 | D | — | — | 0.9 | — | 75 | 3.0 | 12 | 5.0 | 3.6 | 72.8 |
|  | P | — | 0.6 | — | 0.2 | 70 | 1.5 | 12 | 11.7 | 10.7 | 81.4 |
|  | D | — | — | 0.3 | — | 85 | 2.5 | 12 | 5.7 | 5.0 | 88.7 |
| 5–6 | X | — | — | — | — | 50 | 1.0 | 5 | 7.0 | 7.1 | — |
|  |  |  | 13 XU/g o.d.p. |  |  |  |  |  |  |  |  |
|  | C/D | 1.22 | — | 0.5 | — | 40 | 0.5 | 3 | 3.1 | 3.1 | — |
|  | E | — | 2.0 | — | — | 70 | 1.5 | 12 | 12.5 | 11.4 | 55.0 |
|  | Kappa Index: 3.0 |  |  |  |  |  |  |  |  |  |  |
| 5 | D | — | — | 0.6 | — | 75 | 3.0 | 12 | 5.0 | 4.3 | 72.2 |
|  | P | — | 0.6 | — | 0.2 | 70 | 1.5 | 12 | 11.9 | 10.6 | 80.1 |
|  | D | — | — | 0.3 | — | 85 | 2.5 | 12 | 5.7 | 4.8 | 88.2 |
| 6 | D | — | — | 0.9 | — | 75 | 3.0 | 12 | 5.0 | 3.6 | 72.6 |
|  | P | — | 0.6 | — | 0.2 | 70 | 1.5 | 12 | 11.9 | 10.6 | 81.7 |
|  | D | — | — | 0.3 | — | 85 | 2.5 | 12 | 5.7 | 4.9 | 89.3 |

As can be seen from the above, use of the. xylanase of *B. pumilus* PRL B12 is efficient for the pretreatment (biobleaching) of wood pulp in classical bleaching sequences. First, it is noted that use of the xylanase as a pretreatment permitted a substantial reduction in the active chlorine used in the chemical-treatment step of the delignification stage. Second, after the delignification stage, the Kappa Index of each of the samples noted above, was greatly reduced (from 12.3 to 3.0–3.2), thereby indicating that use of this xylanase as a pretreatment permits wood pulp to be obtained that has an acceptably-low lignin content (as measured by the Kappa Index of the wood pulp).

EXAMPLE 15
Effect of Xylanase Pretreatment in ECF Sequences

From the oxygen-treated hardwood pulp of Example 14, six suspensions (samples) were prepared. Three (3) of these samples (designated samples 4, 5 and 6) were, first, subjected to an enzymatic treatment without washing between enzymatic treatment and the first dioxide chlorination. All of the samples were then subjected to an ECF bleaching sequence of the type DPDPD. These ECF sequences were performed using increasing weights of chlorine dioxide.

Full details of the operating conditions and the results of the various trials of these samples can be seen by reference to Table 8.

TABLE 8

Efficacy of *B. pumilus* PRL B12 Xylanase Pretreatment in Elemental Chlorine Free Bleaching Sequences

| Sample | Step | Reactants (g/100 g o.d.p.) ClO₂ | H₂O₂ | NaOH | Temp °C. | Time (Hr) | Con. (%) | pH Start | End | °ISO | Kappa Index |
|---|---|---|---|---|---|---|---|---|---|---|---|
| 1–3 | D | 2.0 | — | — | 60 | 0.5 | 3 | 3.6 | 3.5 | — | — |
|  | P | — | 0.5 | 2.0 | 70 | 1.5 | 12 | 12.2 | 11.5 | 68.9 | 5.5 |
| 1 | D | 0.4 | — | — | 75 | 3.0 | 12 | 5.7 | 5.3 | 79.5 | — |
|  | P | — | 0.2 | 0.6 | 70 | 1.5 | 12 | 12.0 | 11.0 | 82.3 | — |
|  | D | 0.3 | — | — | 85 | 2.5 | 12 | 5.9 | 5.0 | 86.0 | — |
| 2 | D | 0.6 | — | — | 75 | 3.0 | 12 | 5.4 | 4.8 | 79.4 | — |
|  | P | — | 0.2 | 0.6 | 70 | 1.5 | 12 | 12.0 | 11.0 | 83.0 | — |
|  | D | 0.3 | — | — | 85 | 2.5 | 12 | 5.6 | 4.9 | 86.6 | — |

TABLE 8-continued

Efficacy of B. pumilus PRL B12 Xylanase Pretreatment
in Elemental Chlorine Free Bleaching Sequences

| Sample | Step | Reactants (g/100 g o.d.p.) | | | Temp ° C. | Time (Hr) | Con. (%) | pH | | °ISO | Kappa Index |
|---|---|---|---|---|---|---|---|---|---|---|---|
| | | $ClO_2$ | $H_2O_2$ | NaOH | | | | Start | End | | |
| 3 | D | 0.8 | — | — | 75 | 3.0 | 12 | 6.1 | 4.6 | 80.6 | — |
| | P | — | 0.2 | 0.6 | 70 | 1.5 | 12 | 12.0 | 10.9 | 84.2 | — |
| | D | 0.3 | — | — | 85 | 2.5 | 12 | 5.5 | 4.9 | 87.5 | — |
| 4–6 | X | — | — | — | 50 | 1.0 | 5 | 7.0 | 7.0 | — | — |
| | | 8 XU/g o.d.p. | | | | | | | | | |
| | D | 1.3 | — | — | 60 | 0.5 | 3 | 3.8 | 3.8 | — | — |
| | P | — | 0.5 | 2.0 | 70 | 1.5 | 12 | 12.5 | 11.6 | 66.9 | 5.9 |
| 4 | D | 0.4 | — | — | 75 | 3.0 | 12 | 5.4 | 5.0 | 78.0 | — |
| | P | — | 0.2 | 0.6 | 70 | 1.5 | 12 | 12.0 | 10.8 | 82.4 | — |
| | D | 0.3 | — | — | 85 | 2.5 | 12 | 5.2 | 4.5 | 86.2 | — |
| 5 | D | 0.6 | — | — | 75 | 3.0 | 12 | 5.5 | 4.6 | 78.5 | — |
| | P | — | 0.2 | 0.6 | 70 | 1.5 | 12 | 12.0 | 10.7 | 83.6 | — |
| | D | 0.3 | — | — | 85 | 2.5 | 12 | 5.0 | 4.2 | 86.6 | — |
| 6 | D | 0.8 | — | — | 75 | 3.0 | 12 | 5.9 | 4.6 | 79.3 | — |
| | P | — | 0.2 | 0.6 | 70 | 1.5 | 12 | 12.0 | 10.8 | 84.3 | — |
| | D | 0.3 | — | — | 85 | 2.5 | 12 | 5.6 | 4.8 | 88.2 | — |

As can be seen from the above, it is clear that an enzymatic treatment with the use of the xylanase of B. pumilus PRL B12 demonstrates good efficiency and efficacy in the pretreatment (biobleaching) of wood pulp in ECF bleaching sequences, permitting a wood pulp to be obtained that has an acceptably-low lignin content, as well as permitting a substantial economy of chlorine dioxide which must be used while still attaining an elevated final whiteness. This is interesting due to the fact that, industrially, the capacity of the chlorine dioxide generator is often limited.

In the above regard, it is noted that after the xylanase treatment step for each of the samples noted above, the Kappa Index was greatly reduced (from 12.3 to 5.9), thereby indicating that the amount of lignin that remained in the pulp, as well as the amount of $ClO_2$ needed during subsequent steps of the bleaching sequence was greatly reduced.

EXAMPLE 16

Effect of Xylanase Pretreatment In TCF Sequences

From the oxygen-treated Kraft hardwood pulp of Example 14, four suspensions (samples) were prepared. Two samples (designated samples 1 and 2) were then used in a totally chlorine free (TCF) bleaching sequence of the type OQPZP (Oxygen, Sequestrant treatment, Peroxide, Ozone, Peroxide). The other two samples were subjected to a totally chlorine free (TCF) bleaching sequence of the type OX/QPZP. The enzyme used in the enzymatic treatment was xylanase derived from B. pumilus PRL B12.

No washing of the pulp was performed between X and Q, but the pH was adjusted to the values noted in Table 9 below.

The enzymatic activity utilized was from 10 XU/gram of dry pulp.

The reactants (with the exception of ozone) used in the steps of the sequences are (in grams per 100 grams of the oven-dried pulp to be treated therewith) as follows: O [6 bars $O_2$, 2.5 NaOH, 0.5 $MgSO_4*7H_2O$]; X/Q [10 XU/g at pH 7.5, 0.5% DTPA (40%) at pH 5.5 (acidification with dilute $H_2SO_2$)]; Q [0.5% DTPA (40%) at pH 5.5 (acidification with dilute $H_2SO_2$)]; P [1.5 $H_2O_2$, 1.8 NaOH, 0.5 $MgSO_4*7H_2O$, 2.5 sodium silicate (water-glass quality 38° beaumé)]; Z [see Table 9]; P [2.0 $H_2O_2$, 1.6 NaOH, 1.0 $MgSO_4*7H_2O$, 3.0 sodium silicate (water-glass quality 38° beaumé)]. The operating conditions, the quantity (in grams per 100 grams of oven-dried pulp to be treated therewith) and the results of the various trials of these samples can be seen by reference to Table 9.

TABLE 9

Efficacy of B. pumilus PRL B12 Xylanase Pretreatment
in Totally Chlorine Free Bleaching Sequences

| Sample | Step | O3 | Temp ° C. | Time (min) | Con. (%) | pH Start | pH End | °ISO | Kappa Index |
|---|---|---|---|---|---|---|---|---|---|
| 1–2 | O | — | 120 | 90 | 15 | 12.7 | 9.6 | 56.8 | 7.4 |
| | Q | — | 50 | 30 | 5 | 5.5 | 6.0 | — | — |
| | P | — | 70 | 120 | 12 | 11.6 | 11.2 | 73.1 | 6.4 |
| 1 | Z | 0.35 | 22 | 2¼ | 40 | 3.0 | 3.6 | 79.7 | — |
| | P | — | 80 | 240 | 30 | ~11.0* | 9.6 | 88.8 | — |
| 2 | Z | 0.52 | 22 | 3½ | 40 | 3.0 | 3.4 | 83.1 | — |
| | P | — | 80 | 240 | 30 | ~11.0* | 9.5 | 91.0 | — |
| 3–4 | O | — | 120 | 90 | 15 | 12.7 | 9.6 | 56.8 | 7.4 |
| | X/Q | — | 50 | 90 | 5 | 7.5 | 7.6 | — | — |
| | P | — | 70 | 120 | 12 | 11.7 | 10.9 | 76.0 | 5.5 |
| 3 | Z | 0.28 | 22 | 2¼ | 40 | 3.0 | 4.0 | 81.3 | — |
| | P | — | 80 | 240 | 30 | ~11.0* | 10.8 | 89.6 | — |
| 4 | Z | 0.43 | 22 | 3 | 40 | 3.0 | 3.9 | 83.5 | — |
| | P | — | 80 | 240 | 30 | ~11.0* | 10.4 | 91.5 | — |

*These pH's represent approximate values. The actual values range between 10.5 and 11.5.

The results of the above-noted trials clearly show that an enzymatic treatment with the xylanase of the present invention permits an impressive reduction in the quantity of ozone needed to be utilized in a TCF sequence while still producing a higher final whiteness. This represents not only a substantial savings in costly ozone but also reduces the quantity of ozone, which can degrade the pulp, which is employed therein.

EXAMPLE 17

Preparation of Xylanase Expression Vector

1. Extraction of chromosomal DNA from Bacillus pumilus PRL B12

L-B medium was innoculated with 200 ml of the culture from Flask A (Example 1) and then cultivated in the L-B medium for 16 hours at 37° C. The DNA was then extracted from the culture as was described above in the section entitled "Methods and Techniques".

2. Constructions of a *Bacillus pumilus* PRL B12 Gene Library

The extracted *B. pumilus* PRL B12 chromosomal DNA was then partially digested with Sau3AI. The reported quantity of DNA to enzyme used was adjusted in such a manner as to obtain a maximum of chromosomal DNA fragments having sizes of between 2 and 7 kbp (kbp: $10^3$ base pairs).

The DNA fragments obtained were then subjected to 0.8% (w/v) agarose gel electrophoresis in order to effect a separation of the DNA fragments according to size. The DNA fragments having a size of between 2 and 7 kbp, as identified from the gel electrophoresis, were then isolated and purified using the "Gene Clean" method or the filtration method using centrifugation.

The purified DNA fragments were then ligated with plasmid pBR322 which had previously been digested at the BamHI site and then dephosphorylated.

The obtained ligation was then transformed into cells of *E. coli* MC1061 by electroporation. The transformed *E. coli* MC1061 cells were then cultured at 37° C. on 1.5% L-B agar plates supplemented with 100 µg/ml of ampicillin and 0.8 g/l of AZCL-xylan.

The resulting colonies constituted the gene library of *B. pumilus* PRL B12.

3. Screening The Gene library for Recombinant Plasmids Containing the Xylanase Gene of *Bacillus pumilus* PRL B12

After about 24 hours of growth on the plates at 37° C. in the culture media described above, the colonies showing an AZCL-xylan hydrolysis zone were identified and their plasmids analyzed. The plasmids present in these colonies were isolated following the alcaline lysis technique described in (3) at 1.25–1.28.

The analysis (by restriction) indicated that various isolated plasmids contained the same xylanase gene, albeit on different sizes of *B. pumilus* chromosomal fragments. The restriction analysis further indicated that the shortest DNA fragment obtained that included the xylanase gene was approximately 2.7–2.8 kbp in size, being carried by the pBR322 plasmid which had been ligated therewith. This new plasmid was designated pBPX1.

4. Subcloning of Chromosomal Fragment Containing Xylanase Gene

The expression vector containing the *B. pumilus* PRL B12 xylanase gene is pUB-BPX12 (FIG. 4). The expression vector was obtained by subcloning of the chromosomal fragment from pBPX1 that contained the xylanase gene.

The shuttle vector (*E. coli-B. subtilis*) pUB131 (obtained as described in European Patent Application No. 90116322.0) was digested at the BamHI site and dephosphorylated.

The recombinant pBPX1 plasmid (obtained as described above) was then subjected to a partial digestion with Sau3AI. The fragments obtained from this digestion were then ligated with the linearized and dephosphorylated pUB131 shuttle plasmid. The obtained ligation was then transformed into *E. coli* MC1061 cells by electroporation.

The transformants were then selected on L-B plates supplemented with 100 µg/ml of ampicillin, 25 µg/ml of kanamycine and 0.8 g/l of AZCL-xylan. After growth for 24 hours at 37° C., the colonies showing zoning were transferred and reisolated. Plasmid pUBC-BPX12, present in these transformants was then isolated by the alkaline lysis technique. Restriction analysis showed that this isolated plasmid (pUBC-BPX12) includes the xylanase gene on an approximately 1.0 kbp Sau3AI fragment (the expression cassette) of *B. pumilus* PRL B12 chromosomal DNA.

When the plasmid pUBC-BPX12 is reintroduced into the strain *E. coli* MC1061, all the resulting transformants show large zoning on AZCL-xylan medium, thus demonstrating the good expression of the xylanase gene in *E. coli*.

pUBC-BPX12 was then used to transform cells of *E. coli* JM109 using the CaCl$_2$ technique and transformants were selected. One transformant containing plasmid pUBC-BPX12 was isolated and a large scale preparation was carried out in order to determine the nucleotide sequence of the inserted fragment containing the xylanase gene.

The sequencing strategy utilized was a direct strategy using progressive oligonucleotides as described by (3) at page 13.15 and 13.17 (FIG. 13.3B), using the double-stranded pUBC-BPX12 plasmid as a template.

For initiating the sequence determination, the oligonucleotides were designed to hybridize with the vector pUBC131, in order to determine the nucleotide sequence in both extremities of the approximately 1.0 kbp xylanase fragment. The sequence of these synthetic oligonucleotides is given hereafter

SEQ ID NO:3 5'-GTAGAGGATCATCATGT-3'

SEQ ID NO:4 5'-TACCTTGTCTACAAACCCC-3'

SEQ ID NO:5 5'-TGAGTTGCTAGTAACATCT-CACCGA-3'

The rest of the sequence was determined by using oligonucleotides synthetized according the newly determined sequence.

The results of this sequenced determination revealed that the xylanase gene had been obtained as a 1022 bp Sau3AI fragment which can be seen by reference to FIGS. 1a and 1b (SEQ ID NO:1).

The xylanase gene was then obtained on a 1061 bp SalI-EcoRV DNA fragment containing the xylanase gene by double digestion of pUBC-BPX12 with SalI and EcoRV, followed by purification by electrophoresis in agarose gel.

The vector pUB131 was then digested with restriction enzyme at the EcoRV and SalI sites and the 1061 bp SalI-EcoRV fragment was ligated therewith.

The resulting ligation was then introduced, following the competent cell technique, into *B. subtilis* SE3 host cells. Transformants were selected on L-B plates supplemented with 25 µg/ml of Kanamycin and analysed by restriction as described above. The resulting plasmid was pUB-BPX12 (FIG. 4).

EXAMPLE 18

Preparation of Pullulanase Expression Vector pUBDEBRA1

Figure 5:
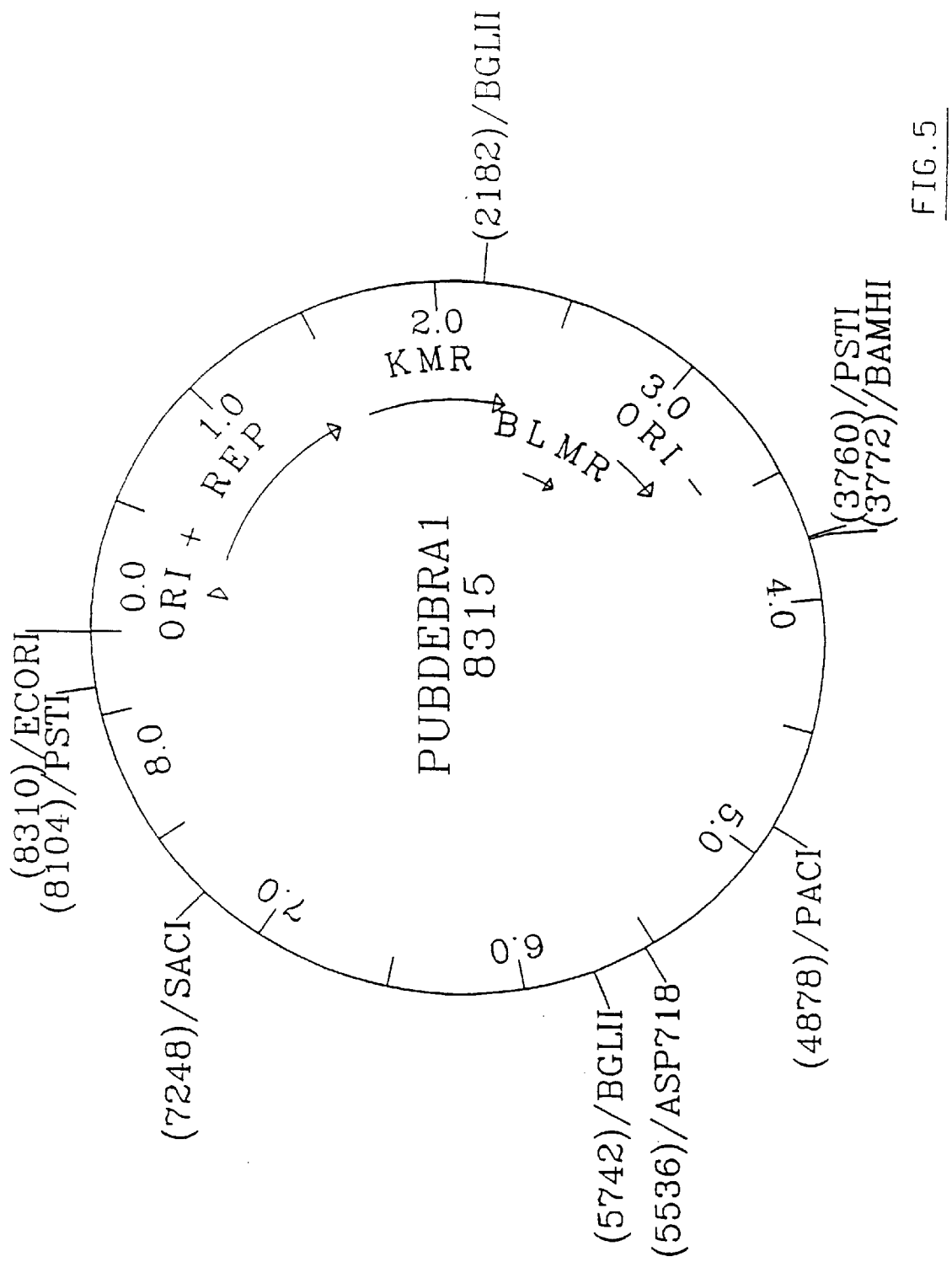
FIG. 5 is a restriction map of plasmid pUBDEBRA1.

Expression vector pUBDEBRA1 (FIG. 5) is a plasmid which contains the gene coding for pullulanase of *B. deramificans* T 89.117D under the control of its own pullulanase transcription promoter, cloned in the vector pUB131. This plasmid (pUBDEBRA1) is obtained, as described below.

*Bacillus deramificans* T 89.117D was cultivated in 200 ml of MYE medium composed of K$_2$HPO$_4$ 33 mM, KH$_2$PO$_4$*3H$_2$O 6 mM, (NH$_4$)$_2$SO$_4$ 45 mM, MgCl$_2$*6H$_2$O 1 mM, CaCl$_2$*2H$_2$O 1 mM, yeast extract 0.5% (w/v), glucose 0.5% (w/v), pH adjusted to 4.5 with H$_3$PO$_4$. The chromosomal DNA was extracted from this culture and purified as described above in the section headed "Methods and Techniques". A *B. deramificans* gene library was constructed by cloning partial Sau3AI fragments in pBR322, as described in example 17 (part 2), except that the size of the partial Sau3AI DNA fragments was 5–10 kbp, instead of 2–7 kbp, and the transformed E. coli MC1061 cells constituting the library were plated on a different medium L-B supplemented with 100 μg/ml ampicillin.

The colonies were grown for 18 hours at 37° C., and transferred to a second plate containing an identical medium. One of the plates was covered with a 1% agar overlay containing 100 mM sodium acetate (pH 4.5) and 0.1% AZCL-pullulan. After an incubation at 60° C. for 18 hours, a colony showing a zoning was identified and isolated from the corresponding replicated plate. A plasmid, designated pBRDEBRA3 was isolated from this colony by the small-scale alcaline lysis method described above, and a restriction analysis thereof showed that the plasmid contained an inserted fragment from B. deramificans T 89.117D of 9 kbp.

A 4.5 kbp EcoRI-BamHI fragment of pBRDEBRA3 was obtained by double digestion of pBRDEBRA3 with EcoRI and BamHI and subsequent purification by electrophoresis in a 0.8% agarose gel. This fragment was then ligated with vector pUB131, which had previously been subjected to a double digestion with BamHI and EcoRI, at the BamHI and EcoRI sites thereof, using B. subtilis PSL1 as a cloning host.

The resulting plasmid pUBDEBRA1 was isolated and purified from the transformed pSL1 cells by the large scale alcaline lysis method. The plasmid preparation was tested for the functionality of the cloned pullulanase gene by transformation in B. subtilis PSL1. All transformants obtained were able to express and secrete the pullulanase gene, since zoning was observed when the colonies were overlayed with AZCL-pullulan.

The transformed B. subtilis PSL1 colonies containing pUBDEBRA1 were transferred to a second L-B plate supplemented with 25 μg/ml of Kanamycin. One of the plates was covered with a 1% agar overlay containing 100 mM sodium acetate (pH 4.5) and 0.1% AZCL-pullulan. After an incubation at 60° C. for 18 hours, all the transformant colonies showed an AZCL degradation halo.

EXAMPLE 19

Preparation of Alkaline Protease Expression Vector pKAC1

Expression vector pKAC1 (FIG. 6) is a plasmid which contains the gene coding for the alkaline protease of B. subtilis 168, under the control of its own promoter, cloned in the vector pUB110. This plasmid (pKAC1) is obtained as described below.

Plasmid pSBT2 was isolated from the chromosomal DNA of B. subtilis 168 as follows:

First, the chromosomal DNA was extracted and purified as described in the section entitled "Methods and Techniques". Then, the extracted and purified DNA was then submitted to a restriction digestion with ClaI. The resulting DNA fragments were then separated according to size on an agarose gel (0.8% w/v) and fragments of 3–5 kbp in size were extracted and purified by the Gene Clean method.

The resulting preparation was then treated with the Klenow fragment of DNA polymerase to fill the 5' protruding ClaI cohesive termini. The resulting DNA preparation was then ligated with vector pMK4, which had been previously digested with SmaI and dephosphorylated. The ligation was transformed into E. coli MC1061 by the CaCl₂ technique, and around 1,000 transformant colonies were selected on L-B plates containing 100 μg/ml ampicillin.

The transformant colonies obtained were then pooled by resuspension in 50 ml liquid L-B medium and their plasmid content was extracted using the large scale plasmid preparation method.

This plasmid preparation was then transformed into B. subtilis 512 PN⁻ and the transformants plated on protease detection plates. B. subtilis 512 PN⁻ is a mutant of B. subtilis 168 which produces a small zoning halo on protease detection plates (Millet et al., (1976) Biochimie, 58:109–117). The transformant colonies were then visually inspected for the presence of a halo of a larger size. A colony presenting such a halo was isolated and its plasmid was extracted using the small scale plasmid preparation method described above.

The resulting plasmid, designated pSBT2, was then transformed into E. coli JM109 and a large scale plasmid preparation of pSBT2 was made from an E. coli transformant. This plasmid preparation of pSBT2 was transformed again into B. subtilis 512 PN⁻. All the transformants obtained exhibited a larger halo on protease detection plates than the control strain (B. subtilis512PN⁻ containing vector pMK4), thus showing that the alcaline protease gene was expressed in B. subtilis from plasmid pSBT2.

Figure 6:
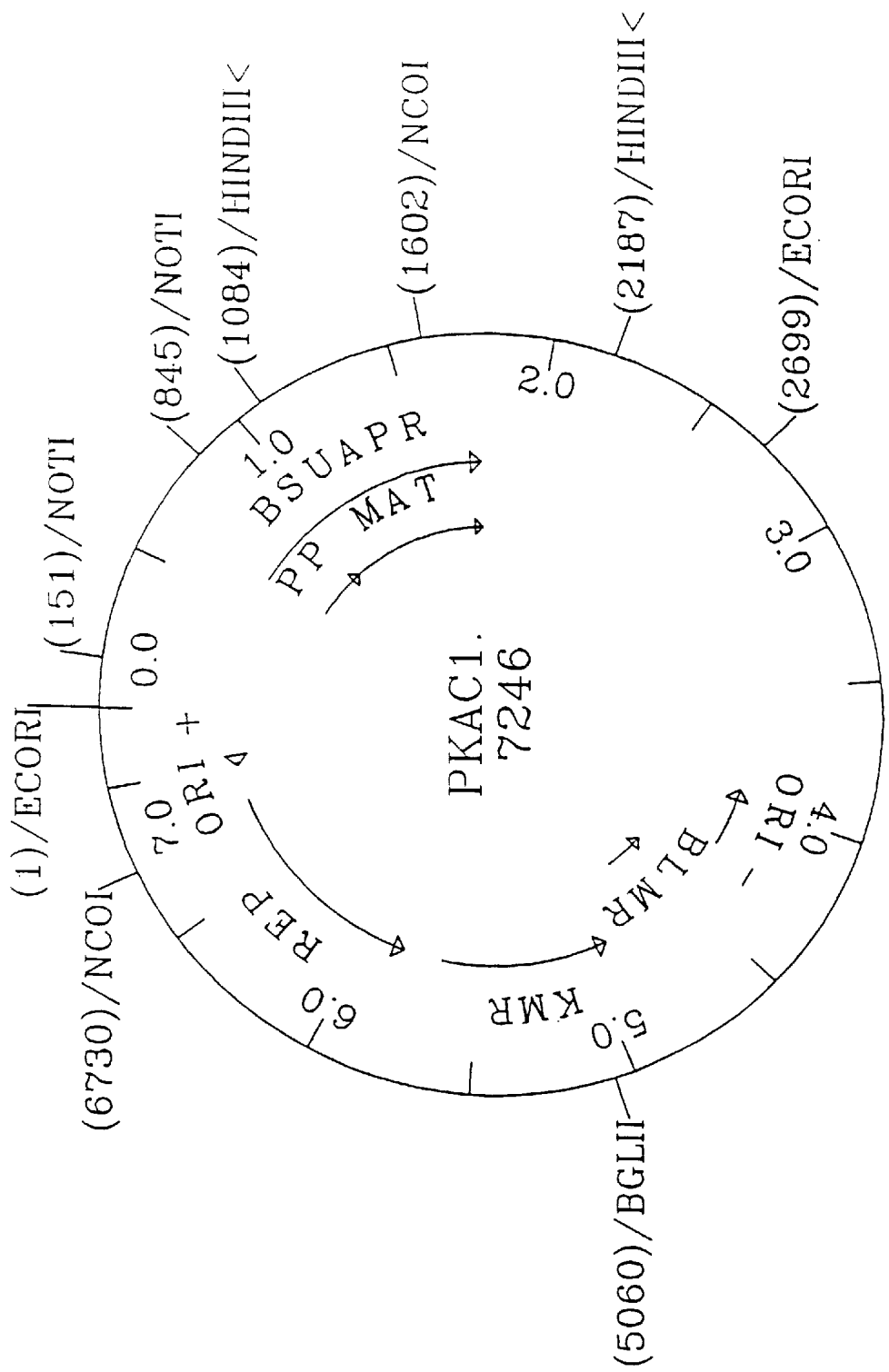
FIG. 6 is a restriction map of plasmid pKAC1.

The plasmid pSBT2 was then digested with EcoRI and a 2.7 kbp EcoRI-EcoRI fragment of plasmid pSBT2 was then subcloned into the EcoRI site of the pUB110 plasmid, using B. subtilis SE3 as a cloning host. The resulting plasmid is pKAC1 (FIG. 6).

EXAMPLE 20

Preparation of Alkaline Protease Expression Vector pLI1

Expression vector pLI1 (FIG. 7) is a plasmid which contains the entire gene coding for the alkaline protease of B. licheniformis SE2 under the control of its own transcription promoter cloned in the vector pUB131. This plasmid (pLI1) is obtained as described below.

The 800 bp DraI-PstI fragment of pKP1, the construction of which is described below in example 23 part 3, was subcloned into the PstI-HincII sites of phagemid pBS-, to create the plasmid pKN8. Plasmid pKN8 was then subjected to a site-directed mutagenesis in order to remove the StyI site using the following synthetic oligonucleotide, which had been previously been extemporaneously prepared:

SEQ ID NO:6 5'-AAGCTTGTATGCCTGCAG-3'

The plasmid created was pKN9.

The vector pUBC134 was then constructed. First, the PstI site of pUBC132 was deleted by removing the 3' protruding terminus by treatment thereof with T4 DNA polymerase as described in (3) at pages F.4–F.5. The resulting plasmid was pUBC133.

The following synthetic double-stranded DNA was constructed and cloned into the SacI-BamBI sites of pUBC133:

SEQ ID NO:7 5'-GATCCCCCTTGGCTGCAGGAGCT-3'

SEQ ID NO:8 3'-GGGAACCGACGTCC-5'

This insertion created the plasmid pUBC134.

The plasmid pUBC134C was then constructed by cloning of the 548 bp PstI-SacI fragment of pKC1 (constructed as described below in Example 23, part 2) into the SacI-PstI sites of pUBC134 after double digestion of both pUBC134 and pKC1 with PstI and SacI. The 812 bp BamRI-PstI fragment of pKN9 was obtained by a double digestion of pKN9 with BamHI and PstI. This 812 bp fragment was then cloned into the PstI-BamHI sites of vector pUBC134C. The 2. Preparation of pBS7MASE The vector pBS5 was created by cloning the following double-stranded synthetic DNA:

A 5'-GATCC CC GGGACCT T AGGCCT TTAATTAA CCTTGG CGGCCG CTCGAG GAGCT-3'
B 3'-         G GG CCCTGGA A TCCGGA AATTAATT GGAACC GCCGGC GAGCTC C    -5'
      BamHI    SmaI    PpuMI    StuI    PacI    StyI    NotI    XhoI    SacI
A = SEQ ID NO:9
B = SEQ ID NO:10 plasmid generated thereby was the plasmid pLINC, which contains the complete *B. licheniformis* SE2 alkaline protease gene.

The 1001 bp StyI-SacI fragment of pLINC was obtained by a double digestion with StyI and SacI and isolated. This 1001 bp DNA fragment was then subcloned into the SacI-StyI sites of pKPN14, the construction of which is described below in example 25, thereby generating plasmid pKPN15. The pKPN15 transformants were selected using tetracycline selection.

A derivative of plasmid pKPN15 that is able to replicate in *B. subtilis* and *B. licheniformis* strains was then constructed by replacing the replication functions for *E. coli* carried by the 3635 bp SacI-BglII fragment of plasmid pKPN15 with the 2199 bp BglII-SacI fragment that carries the replication functions for Bacillus and which was isolated from plasmid pUB131.

Figure 7:
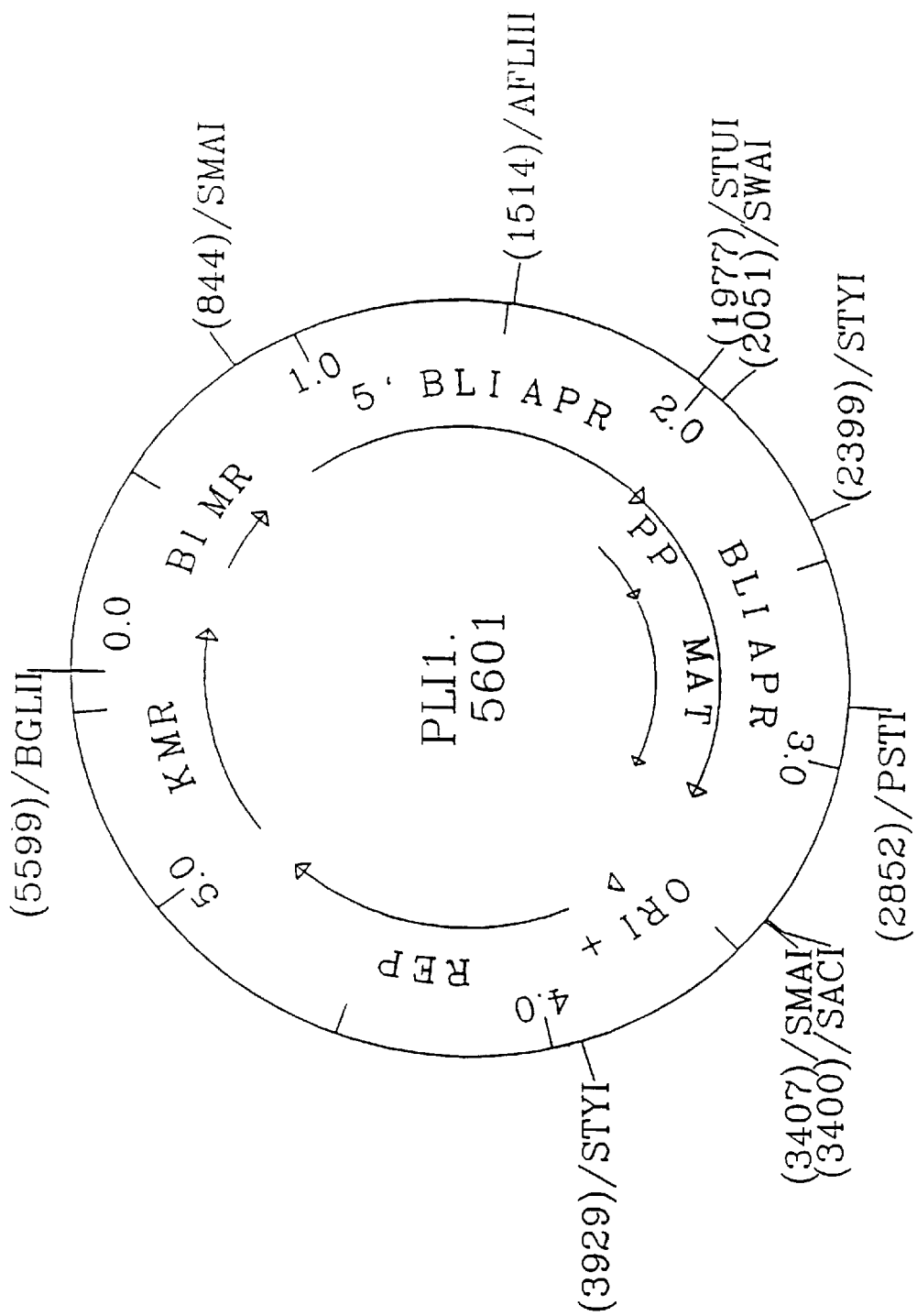
FIG. 7 is a restriction map of plasmid pLI1.

The derivative of plasmid pKPN15, referred to above, was constructed by cloning in *B. subtilis* SE3, the 3402 bp BglII-SacI fragment from pKPN15 into the 2198 bp BglII-SacI vector fragment from pUB131. The resulting plasmid was designated plasmid pLI1 (FIG. 7).

EXAMPLE 21

Preparation of Alkaline Protease Expression Vector pL7SBT

Expression vector pL7SBT (FIG. 8) was constructed, which contains the sequence coding for the alkaline protease of *B. subtilis* 168 under control of the transcription promoter of the alkaline protease of *B. licheniformis* (subtilisin Carlsberg). This plasmid (pL7SBT) is obtained as described below.

1. Preparation of pLI2NC

The 1001 bp StyI-SacI fragment of pLINC (constructed as described above in Example 20).was subcloned into the SacI-StyI site of pLID1 (constructed as described below in Example 25), creating the plasmid pLI2NC.

into the BamHI-SacI sites of pBS-, forming pBS5. The 422 bp StuI-StyI fragment from the plasmid pKPN15 (constructed as described above in Example 20), was cloned into the StuI-StyI sites of pBS5, creating the plasmid pBS5MASE. pBS5MASE was then mutagenisized to introduce therein a PacI site between the transcription promoter and the translation initiation site, with the following synthetic oligonucleotide which was constructed extemporaneously:

SEQ ID NO:11
5'-ATTATATTATCCTTCTAT<u>TTAATTAA</u>TCTGAATAAAGAGGAG-3'
                        PacI

This mutagenesis generated plasmid pBS7MASE, which contained a supplementary PacI site in comparison with pBS5MASE.

3: Preparation of pLI7NC

The plasmid pLI7NC was thereafter constructed by replacing the 422 bp StuI-StyI fragment of the plasmid pLI2NC, as was described above, with the 421 bp StyI-StuI fragment of pBS7MASE, described above.

4. Preparation of pL7SBT

Two synthetic oligonucleotides were constructed having the following sequences:

SEQ ID NO:12
5'-CGC<u>TTAATTAA</u>AAATGAGGAGGGAACCGAGTGAGAAGCAAAAAATTGTGGATCAGCTT-3'
         PacI
SEQ ID NO:13
                        5'-GATCATGGAA<u>CGAGCTC</u>AACATGCGGAGAAAGAAGAG-3'
                                    SacI

These oligonucleotides were then utilized for effectuating an amplification by PCR starting from the plasmid pSBT2 (obtained as described above in Example 19).

pSBT2 contains the complete gene that codes for the alkaline protease (subtilisin) of *B. subtilis* 168. The fragment amplified by PCR contained the ribosome binding site, the alkaline protease coding sequence, as well as the transcription terminator of the gene, flanked (between) by two restriction sites: PacI and SacI. The PCR was performed according to the procedure described above.

43

The amplified fragment was purified on agarose gel (1% w/v), digested by PacI and SacI and cloned into the SacI-PacI sites of the pLI7NC vector, generating the plasmid pLI7SBT.

A derivative of plasmid pLI7SBT able to replicate in *B. subtilis* and *B. licheniformis* was then constructed by replacing the replication functions for *E. coli*, carried by the 4.8 kbp SacI-BglII fragment of the plasmid pLI7SBT with the 2199 bp BglII-SacI fragment isolated from plasmid pUB131 which includes the fragment carrying the replication functions for Bacillus.

Figure 8:
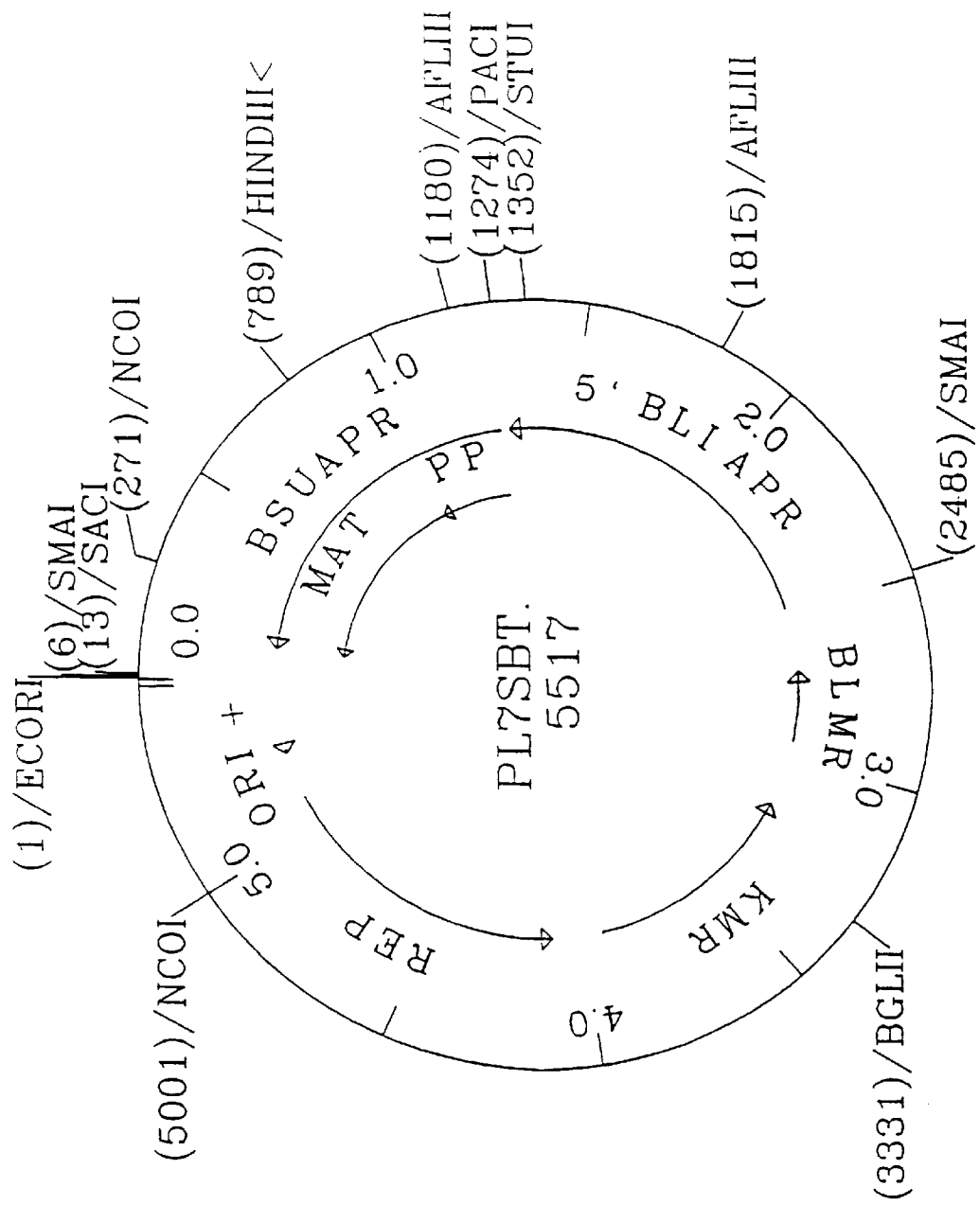
FIG. 8 is a restriction map of plasmid pL7SBT.

Replacement of the replication functions was done by subcloning, in *B. subtilis* SE3, the 3318 bp BglII-SacI fragment from plasmid pLI7SBT into the 2199 bp BglII-SacI fragment isolated from plasmid pUB131. The resulting plasmid is the plasmid pL7SBT (FIG. 8).

EXAMPLE 22

Preparation of Alpha-Amylase Expression Vector pL7TAKA

Expression vector pL7TAKA (FIG. 9) contains the sequence coding for the α-amylase of *B. licheniformis* ATCC 9789 under control of the transcription promoter of the alkaline protease of *B. licheniformis* SE2. This plasmid (pL7TAKA) was obtained as described below.

First, plasmid pS, which contains the complete α-amylase gene of *B. licheniformis* ATCC 9789 cloned on a 3.5 kbp EcoRI fragment in the EcoRI site of pUB110, was isolated. The isolation was carried out as follows:

The chromosomal DNA from *B. licheniformis* ATCC 9789, was extracted and purified from a 200 ml L-B culture. The chtomosomal DNA preparation was then partially digested with EcoRI. The DNA fragments obtained were then ligated to the vector pUB110, which had previously been linearized by EcoR1. The resulting ligation mixture was tranformed into *B. subtilis* BR151, using the protoplast method. The regenerated transformants were then transferred to L-B medium supplemented with 25 µg/ml kanamycin and 1% (w/v) starch.

After 18 hours of growth at 37° C., the transformant colonies were covered with a 0.0025% iodine solution. A colony was then identified which showed a larger starch hydrolysis halo than the control strain (*B. subtilis* BR151) carrying the plasmid pUB110. The plasmid pS was extracted from this transformant, isolated, and analysed by retriction mapping. Plasmid pS contained an approximately 3.5 kbp inserted DNA fragment from *B. licheniformis* ATCC 9789. The sequences of the inserted fragment was determined using the same approach as for the xylanase gene described above in Example 17.

Two synthetic oligonucleotides were constructed having the following sequences:

---
SEQ ID NO:14
    5'-CTTGTTAAAAATTCGGAATAT<u>TTAATTAA</u>ATCATATGTTTCA-3'
                                PacI
SEQ ID NO:15
            5'-GCTGCAAAGCATAATGATGACGGTCC-3'

---

These two synthetic oligonucleotides were then utilized for effectuating an amplification by PCR starting from plasmid pS.

44

The fragment amplified by PCR contains the ribosome binding site and the sequence coding for the α-amylase of *B. licheniformis* ATCC 9789, as well as the transcription terminator of the gene, flanked (between) two restriction sites PacI and SacI.

Plasmid pLI7NC was then prepared as described above in Example 21.

The amplified fragment was purified on agarose gel (1%), digested by PacI and SacI and then cloned into the SacI-PacI sites of the vector pLI7NC, generating the plasmid pLI7TAKA.

A derivative of plasmid pLI7TAKA that was able to replicate in *B. subtilis* and *B. licheniformis* was then constructed by replacing the replication functions for *E. coli* carried by the 3623 bp BglII-BglII fragment of the plasmid pLI7TAKA with the 2238 bp BglII-BamHI fragment isolated from plasmid pUB131, which includes the fragment carrying the replication functions for Bacillus.

Figure 9:
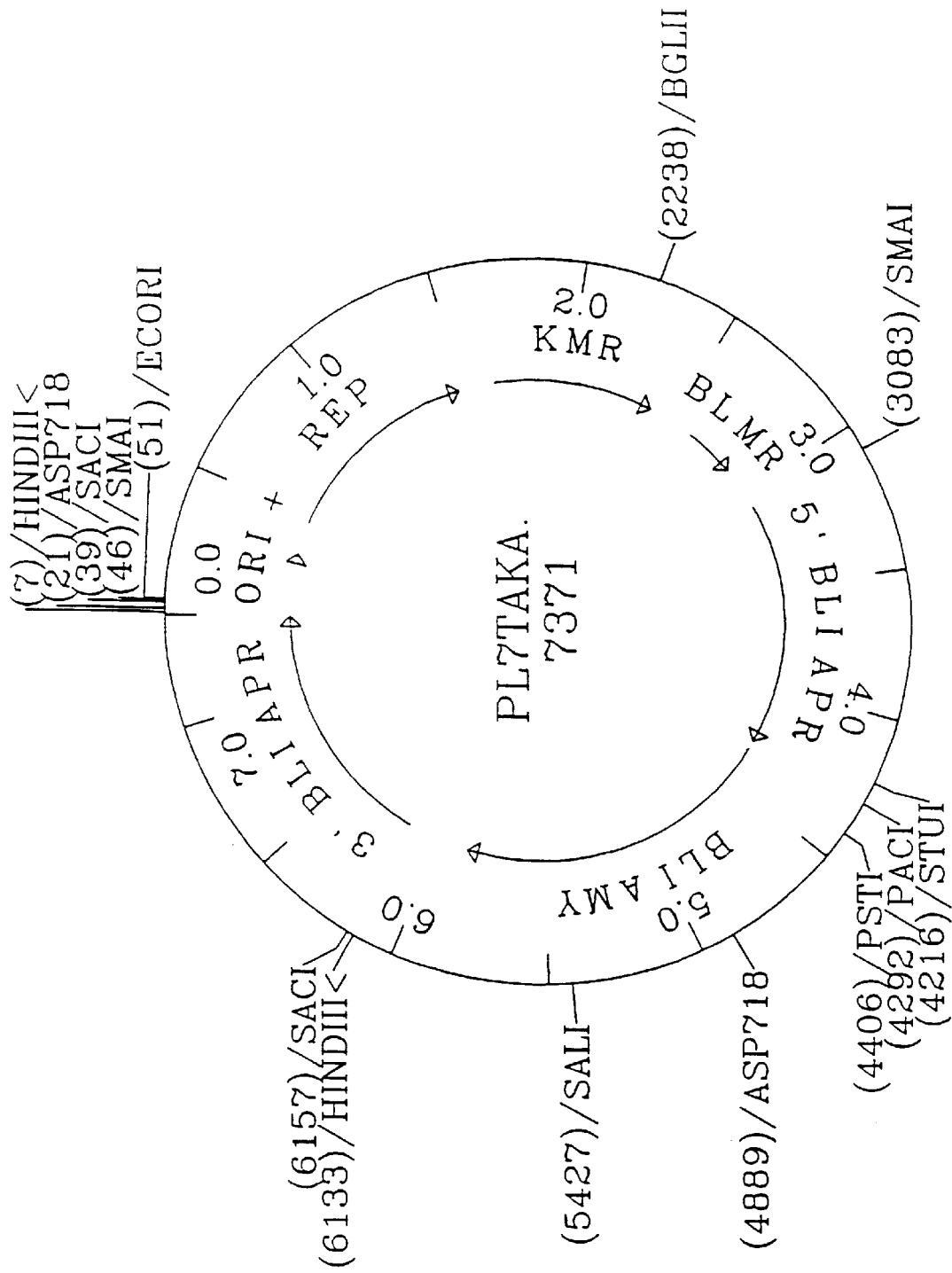
FIG. 9 is a restriction map of plasmid pL7TAKA.

Replacement of replication functions was carried out by cloning, in *B. subtilis* SE3, the 5.1 kbp BglII-BglII fragment of plasmid pLI7TAKA into the 2238 bp BglII-BamHI fragment isolated from plasmid pUB131. The resulting plasmid is pL7TAKA (FIG. 9).

EXAMPLE 23

Cloning of The Terminal Portions of the Alkaline Protease Gene of the *Bacillus licheniformis* Host Strain In order to isolate the alkaline protease gene from the chromosomal DNA of *B. licheniformis* SE2, the strategy used was to, first, extract the chromosomal DNA. Then, the terminal portions of this gene were cloned by hybridization with oligonucleotide probes.

1. Extraction Of Chromosomal DNA from *B. licheniformis* SE2

The chromosomal DNA from *Bacillus licheniformis* SE2 was extracted and purified as described above in the section headed "Methods and Techniques".

2. Cloning of the C-Terminal Portion of the Alkaline Protease Gene

The preparation of extracted chromosomal DNA was then submitted to a restriction analysis. The DNA fragments resulting from these digestions were then separated according to size on a 0.8% (w/v) agarose gel.

The agarose gel was then submitted to an analysis by the Southern Blot Technique, so as to identify the restriction fragments which contain the nucleotide sequences of the C-terminal part of the alkaline protease gene.

The probe constructed and used for the hybridizations was a synthetic oligonucleotide corresponding to the C-terminal part of the alkaline protease gene. The synthetic oligonucleotide sequence that was constructed for this purpose was:

SEQ ID NO:16 5'-GGCGGAGCAAGCTTTGTGG-3' for the C-Terminal

The results showed that the C-terminal portion of the alkaline protease gene was localized on a PstI fragment of about 2.7 kbp.

The preparation of extracted chromosomal DNA from *B. licheniformis* SE2 was then digested with PstI and separated according to size by agarose gel electrophoresis (0.8%). The resulting obtained fragments of about 2.7 kbp were then extracted from the gels and purified following the Gene Clean procedure. The 2.7 kbp PstI fragments were then ligated with the plasmid pUC18, which had been previously digested at the PstI site and dephosphorylated. The ligation thus obtained was then transformed into cells of *Escherchia coli* MC1061 by the CaCl$_2$ technique. The transformants were selected on a L-B plate medium supplemented with 100 μg/ml ampicillin. The transformants obtained in the *E. coli* MC1061 were then screened by hybridization with the radiolabeled synthetic oligonucleotide used as the C-terminal probe in the Southern study and the plasmid pKC1 isolated thereby.

3. Cloning of the N-Terminal Portion of the Alkaline-Protease Gene

The preparation of extracted chromosomal DNA was then submitted to a restriction analysis. The DNA fragments resulting from these digestions were then separated according to size on a 0.8% agarose gel.

The agarose gel was then submitted to an analysis by the Southern Blot Technique, so as to identify the restriction fragments which contain the nucleotide sequences of the N-terminal part of the alkaline protease gene.

The probe constructed and used for the hybridizations was a synthetic oligonucleotide corresponding to the N-terminal part of the alkaline protease gene. The synthetic oligonucleotide sequence that was constructed for this purpose was SEQ ID NO:17 5'-ATGGCTCCTGGCGCAGGC -3' for the N-Terminal The results show that the N-terminal portion of the alkaline protease gene was localized on a PstI fragment of about 5.5 kbp, and equally on a smaller BclI-PstI fragment of about 2 kbp. This fragment did not contain restriction sites for XbaI, ClaI, HpaI and SphI.

The preparation of extracted chromosomal DNA from *B. licheniformis* SE2 was then digested with PstI and then separated according to size by agarose gel electrophoresis (0.8%). The resulting obtained fragments of about 5.5 kbp were then extracted from the gels and purified following the Gene Clean procedure. The resulting 5.5 kbp PstI fragments were then submitted to a series of digestions with BclI, XbaI, ClaI, HpaI and SphI. The DNA fragments thus generated were ligated with plasmid pMK4 (as described in Sullivan, et al., (1984), Gene 29:21–26). which had been previously linearized by BamHI and PstI.

The ligations thereby obtained were then transformed into cells of *E. coli* MC1061 by the CaCl$_2$ technique.

The transformants were selected on a L-B plate medium supplemented with 100 μg/ml ampicillin. The transformants obtained in the *E. coli* MC1061 were then screened by hybridization with the radiolabeled synthetic oligonucleotide used as the N-terminal probe in the Southern study and the plasmid pKP1 isolated thereby.

EXAMPLE 24

Sequencing of the Alkaline Protease Gene

The fragments inserted in the plasmids pKP1 and pKC1 were sequenced from the PstI to the SacI sites thereof by the procedure described above in "Methods and Techniques", using the strategy of progressive oligonucleotides.

EXAMPLE 25

Construction of pLD1 Deletion Plasmid of Mature Alkaline Protease

Following sequencing of the alkaline protease gene described above in Example 24, a deletion plasmid, pLD1 (FIG. 11) was constructed for the purpose of preparing *B. licheniformis* SE2 delap1. This plasmid, pLD1, was obtained as described below.

The pKP1 plasmid proved to be extremely unstable in *E. coli* MC1061. For this reason, the chromosomal DNA fragment containing the N-terminal part of the *B. licheniformis* SE2 alkaline protease gene was subcloned into the vector pACYC184. This subcloning was performed by introducing the 1849 bp EcoRI-EcoRI fragment from pKP1 into the EcoRI site of pACYC184 and the ligation was used to transform cells of *E. coli* MC1061. The resulting plasmid was pKPN11.

Transformants were then selected on a L-B agar medium supplemented with 12.5 μg/ml of tetracycline. The orientation of the 1849 bp EcoRI-EcoRI fragment in the pKPN11 plasmid was then determined by restriction analysis.

The plasmid pKPN12 was obtained by deletion of the 1671 bp StyI-StyI fragment of pKPN11 by digestion with StyI, followed by replacement of that fragment with the following synthetic double-strand of DNA, which had been extemporaneously produced:

| SEQ ID NO:18 | 5' - CTTG GAGCTC GTTAAC AGATCT     -3' |
|---|---|
| SEQ ID NO:19 | 3' -     CTCGAG CAATTG TCTAGA GTTC -5' |
|  | (StyI)  SacI  HpaI  BglII  (StyI) |

The DNA fragment from pUB131 which codes for resistance to Kanamycine and either bleomycine or phleomycine was then obtained as follows First, a 2666 bp PstI-TaqI fragment (having the genes coding for resistance to kanamycine and either bleomycine or phleomycine) was obtained by double PstI-TaqI digestion of plasmid pUB131. This fragment was then introduced into the PstI-AccI sites of the phagemid pBS-. The resulting combination created the plasmid pBSKMPM.

During the cloning of pBSKMPM, described above, a small deletion in the region of. the linker of pBS- appeared, which provoked the loss of the SphI and PstI sites in the plasmid pBSKMPM. Thus, the plasmid pBSKMPM was used to produce a single-strand DNA which was then used to effectuate a site-directed mutagenesis, in order to introduce the two synthetic oligonucleotides having the respective SmaI sites as noted below, so that there were then two SmaI sites, one upstream and one downstream from the kanmycine and phleomycine resistance genes.

The sequences of the synthetic oligonucleotides used for mutagenesis are given as follows:

SEQ ID NO:20
5' - CATCTAATCTTCAACA<u>CCCGGGC</u>CCGTTTGTTGAAC - 3'
                    SmaI
SEQ ID NO:21
5' - CAAAATAAAAAAGATACAA<u>CCCGGG</u>TCTCTCGTATCTTTTAT - 3'
                       SmaI

The plasmid resulting from this mutagenesis in the presence of the two oligonucleotides is pBSKMPM1. This plasmid contains two SmaI restriction sites which permit the isolation of the DNA fragment containing the genes coding for resistance to kanamycine and phleomycine.

The 1597 bp SmaI-SmaI fragment of pBSKMPM1 was thereafter introduced into the SmaI site of pKPN12, thereby creating plasmid pKPN14.

The good orientation of the cloned fragment in the plasmid pKPN14 was then identified by conducting a screening on the small-scale plasmid DNA preparations by restriction analysis, as was described above under the section headed "Methods and Techniques".

The DNA fragment present on pKC1 and located downstream from the N-terminal of the alkaline protease sequence was thereafter isolated on a 1.2 kbp SacI-HindIII fragment of pKP1 (constructed as described above in Example 23, part 2). This isolation was carried out by, first, digestion of pKP1 with HindIII. The HindIII 5' protruding end was then made blunt by treatment with Klenow fragment of DNA polymerase. A SacI restriction was then performed, so as to generate the desired SacI-HindIII (blunt) fragment. This fragment was then cloned into the SacI and HpaI sites of pKPN14, thereby generating the plasmid pLID1.

All of the above constructions were effectuated by transformation of the strain E. coli MC1061 and in the presence of tetracycline (12 μg/ml) for the selection of transformants.

A derivative of the plasmid pLID1 that was able to replicate in strains of B. subtilis and B. licheniformis was thereafter constructed by replacing the functions of replication for E. coli, carried by the 3623 bp BglII-BglII fragment of the pLID1 plasmid with the fragment carrying the replication functions for Bacillus: a 2238 bp BglII-BamHI fragment isolated from plasmid pUB131.

Figure 11:
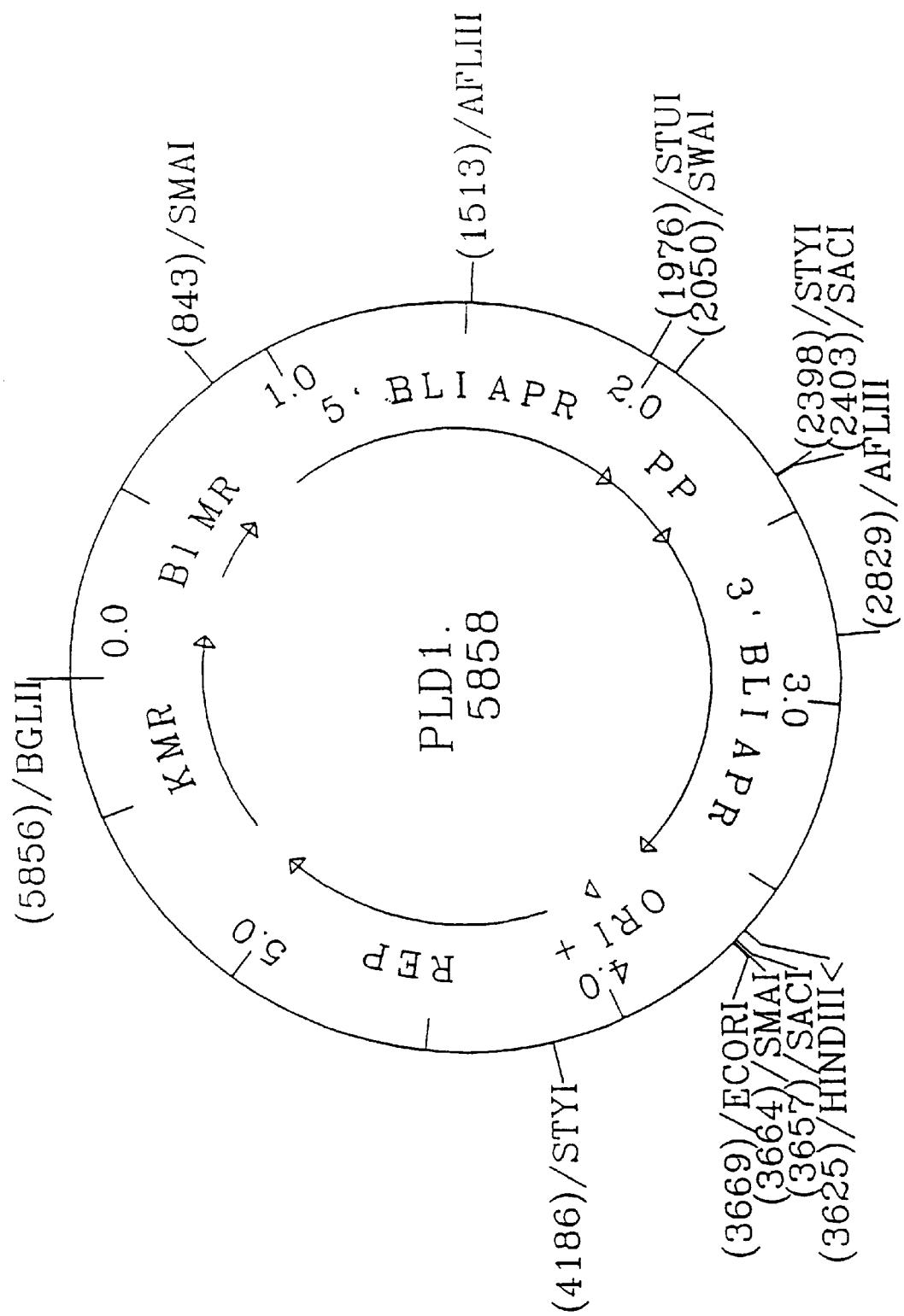
FIG. 11 is a restriction map of plasmid pLD1.

Replacement of the functions of replication for E. coli with those for Bacillus was done by first isolating the 3.6 kbp BglII-BglII fragment from the pLID1 plasmid (the fragment carrying the 5' upstream sequence and the 3'downstream sequence of the alkaline protease gene of B. licheniformis SE2) by digesting pLID1 with BglII and BamHI. The additional BamHI digestion was necessary, since a BglII digestion alone would have resulted in fragments with identical sizes which would not have been able to be separated as desired by agarose gel electrophoresis. The 3.6 kbp BglII-BglII fragment was then cloned in B. subtilis SE3, into the 2238 bp BglII-BamHI fragment which was isolated from plasmid pUB131, generating plasmid pLD1 (FIG. 11).

EXAMPLE 26

Construction of pLD3 Deletion Plasmid of the Sequence Coding for the Entire Alkaline Protease A further deletion plasmid, pLD3 (FIG. 12), was constructed for the purpose of preparing B. licheniformis SE2 delap3. This plasmid pLD3 was obtained as described below.

A double-stranded synthetic oligonucleotide having the sequence:

SEQ ID NO:22    5'-CCT TTAATTAA CCTTGG CGGCCG CTCGAG GAGCT-3'
SEQ ID NO:23    3'-GGA AATTAATT GGAACC GCCGGC GAGCTC C    -5'
                    (StuI)  PacI  StyI  NotI  XhoI  (SacI)

was constructed. This synthetic oligonucleotide was then cloned into the SacI and StuI sites of the plasmid pLID1 (constructed as described above in Example 25) generating the plasmid pLID3.

A derivative of plasmid pLID3 that was able to replicate in strains of Bacillus was thereafter constructed by replacing the replication functions for E. coli, carried by the 3623 bp BglII-BglII fragment of the plasmid pLID3 with the 2238 bp BglII-BamHI fragment (the fragment carrying the replication functions for Bacillus) isolated from plasmid pUB131.

Figure 12:
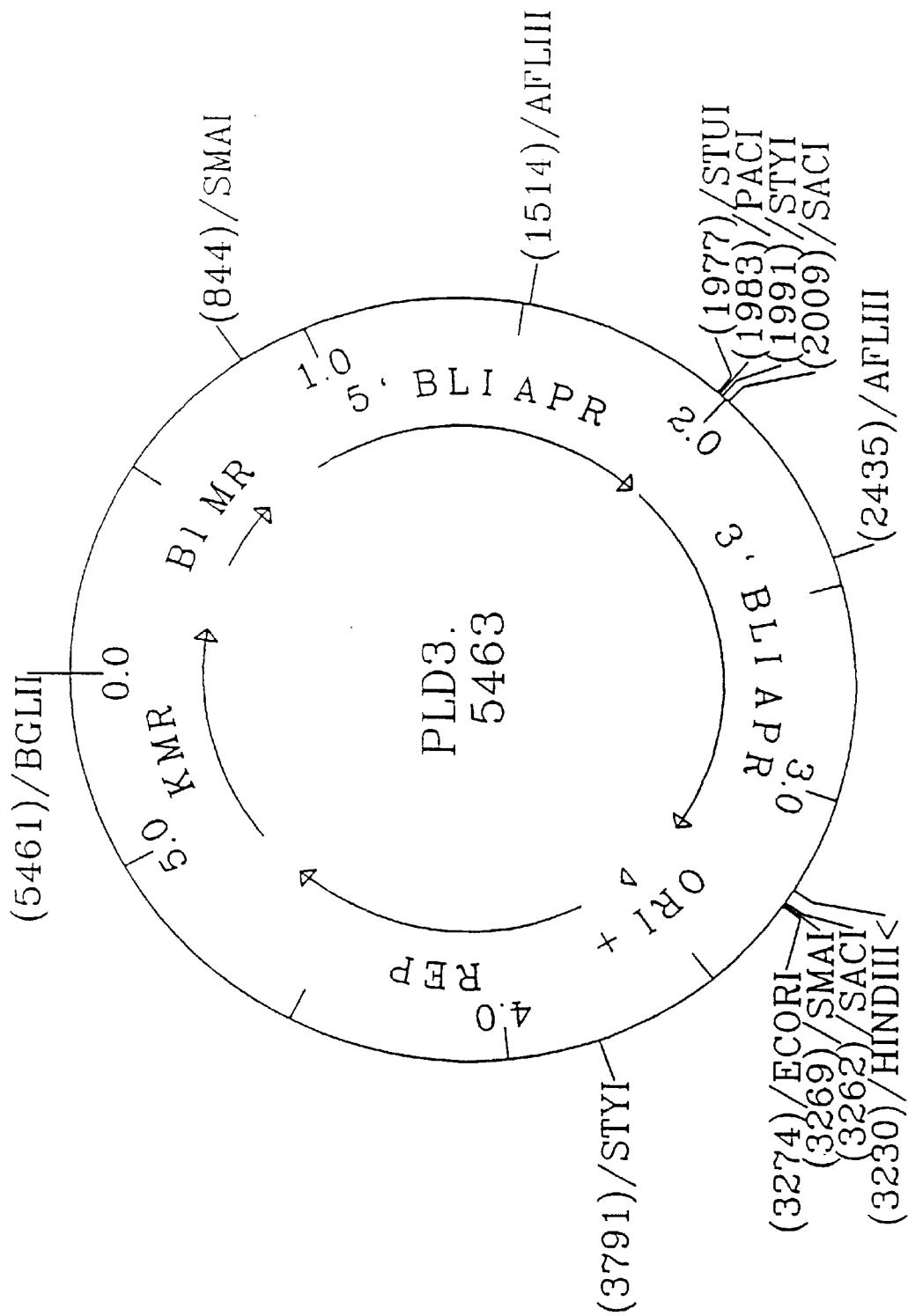
FIG. 12 is a restriction map of plasmid pLD3.

Replacement of the functions of replication for E. coli with those for Bacillus was done by cloning the 3.2 kbp BglII-BglII fragment of the plasmid pLID3 into the 2238 bp BglII-BamHI fragment isolated from pUB131. The resulting plasmid is the plasmid pLD3 (FIG. 12).

EXAMPLE 27

Construction of pLD6 Deletion Plasmid of the Sequence Coding for the Entire Alkaline Protease Gene, Including the Transcription Promoter.

A still further deletion plasmid, pLD6 (FIG. 13), was constructed for the purpose of preparing B. licheniformis SE2 delap6. This deletion plasmid, pLD6, was obtained as described below.

The plasmid pLID6 was constructed by deleting the 0.9 kbp AflIII-AflIII fragment of the plasmid pLID3 (constructed as described above in Example 26). A derivative of this plasmid that was able to replicate in strains of Bacillus was then constructed by replacing the replication functions of E. coli that are carried by the 3623 bp BglII-BglII fragment of the plasmid pLID6 with the 2238 bp BglII-BamHI fragment (the fragment carrying the replication functions for Bacillus) isolated from pUB131.

Replacement of the functions of replication for E. coli with those for Bacillus was done by cloning the 2.3 kbp BglII-BglII fragment from plasmid pLID6 (the fragment carrying the 5' upstream sequence and the 3'downstream sequence of the alkaline protease gene of *B. licheniformis* SE2) into the 2238 bp BglII-BamHI fragment isolated from plasmid pUB131. The result is plasmid pLD6 (FIG. 13).

EXAMPLE 28

Creation, in vivo, of Deleted *B. licheniformis* strains

Figure 10:
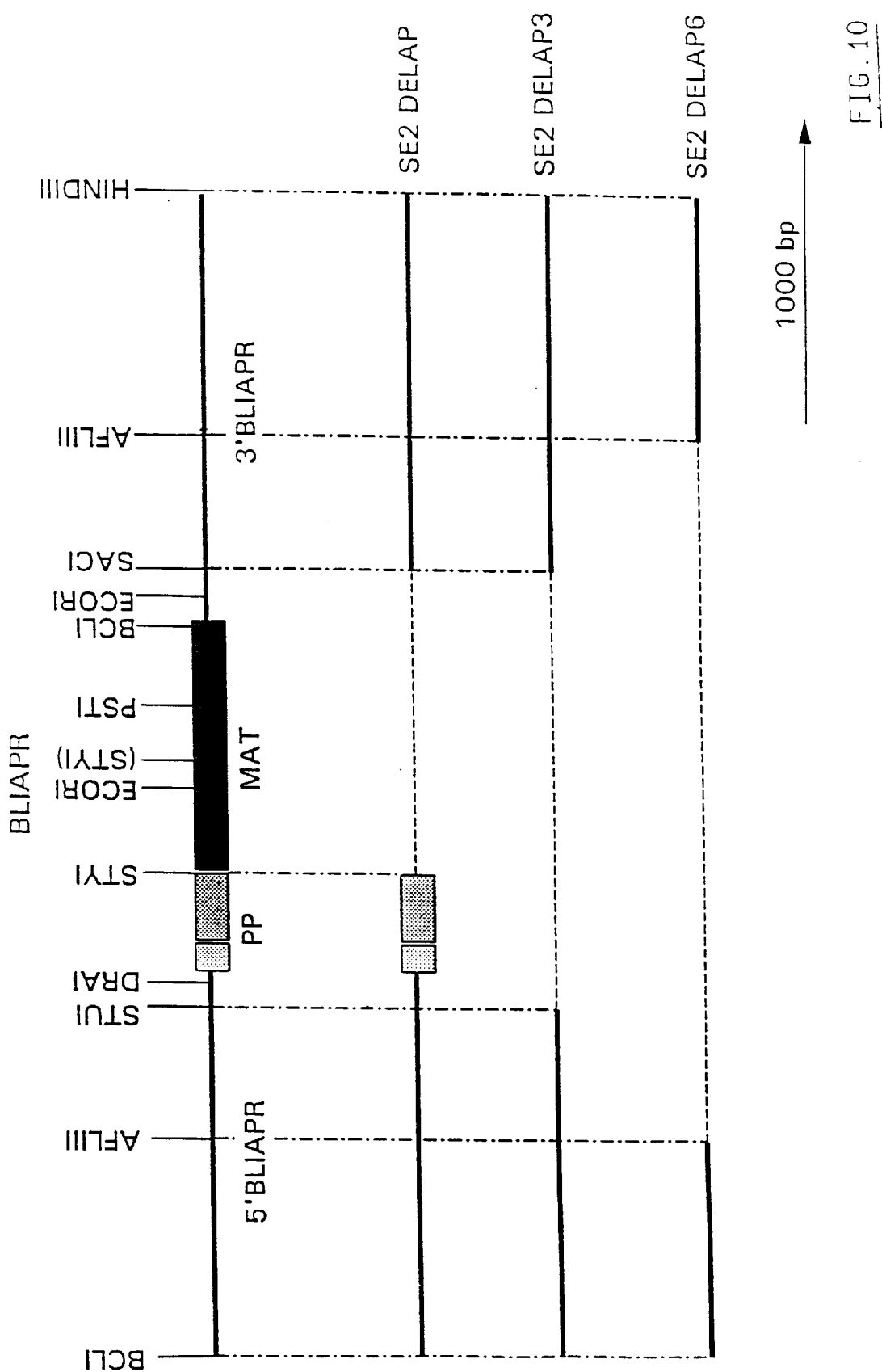
FIG. 10 illustrate the in vivo chromosomal deletions made in *Bacillus licheniformis* SE2 by the deletion plasmids pLD1, pLD3 and pLD6.

The desired deletions in the chromosomal DNA of Bacillus licheniformis SE2 were performed using techniques that are based on homologous recombination, as shall be discussed at length below. The results of the chromosomal deletions obtained, respectively, by the plasmids pLD1, pLD3 and pLD6 are represented in FIG. 10. The deletions were effectuated, as described below, to produce *B. licheniformis* strains SE2 delap1, SE2 delap3 and SE2 delap6.

Each of the deletion plasmids (pLD1, pLD3 or pLD6) were transformed into the respective *Bacillus licheniformis* SE2 delap cultures by the protoplast technique.

Respective transformants were isolated from each of the transformations and the restriction maps of the deletion plasmid introduced therein were verified.

The transformants were thereafter placed in respective cultures of 50 ml of L-B medium supplemented by 2 g/l of glucose and 25 µg/ml of kanamycin, for 18 hours at 37° C.

A volume of 0.1 ml of each of the respective resulting cultures were inoculated into respective flasks containing 50 ml of the same medium, and the cultures were carried out for 18 hours at 37° C. A sample of each of the resulting cultures was withdrawn, and appropriate dilutions were plated on respective protease detection plates supplemented with 25 µg/ml of kanamycin.

The respective plates were visually screened for the presence of colonies showing the absence of zoning, indicating the unability of these colonies to produce alcaline protease. The culturing and screening operations were repeated until respective deleted candidates, which were both unable to produce alcaline protease (apr⁻) and which were resistant to kanamycin (Km$^r$) due to the presence of the respective deletion plasmids, were isolated (apr⁻, Km$^r$).

The plasmids having served for the deletions were thereafter eliminated from the deleted candidate *B. licheniformis* strain (strain SE2 delap1, SE2 delap3, or SE2 delap6) which they had transformed by simple growth on culture media at 37° C. in the absence of an antibiotic.

The deleted candidates were thereafter placed in respective cultures of 50 ml of L-B medium supplemented by 2 g/l of glucose for 18 hours at 37° C. Volumes of 0.1 ml of the resulting cultures were inoculated into respective second flasks, each containing 50 ml of the same medium, and the respective cultures were carried out for 18 hours at 37° C. A sample of the resulting cultures were withdrawn, and appropriate dilutions were plated on L-B plates. The isolated colonies were then replicated on respective second L-B plates supplemented with 25 µg/ml kanamycin, and visually inspected to identify kanamycin sensitive (Km$^s$) colonies.

The culturing and screening operations were repeated for each colony until Km$^s$ candidates were isolated. These candidate strains were then isolated and their phenotypes (apr⁻, Km$^s$) were confirmed.

The chromosomal DNA was thereafter isolated and purified, and the structure of the chromosomal deletion was verified by the Southern blotting technique. The deletions were found to be well-positioned, having taken place by means of the double homologous recombination into the sequences situated upstream (5') and downstream (3'), as is seen in FIG. 10. In FIG. 10, the dotted lines indicate the absence of the deleted sequence(s) in the *B. licheniformis* SE2 chromosomal DNA.

The resulting strain(s) were designated, respectively, *B. licheniformis* SE2 delap1, SE2 delap3 and SE2 delap6, respectively. None of these strains produced alkaline protease.

EXAMPLE 29

Transformation of Deleted *B. licheniformis* SE2 Strains With pUB-BPX12 pUB-BPX12 (FIG. 4) was extracted from *E. coli* MC1061 obtained in Example 17 and isolated and purified. Each of the deleted *B. licheniformis* SE2 strains (delap1, delap3 and delap6), obtained as described above in Example 28, was then transformed by respective pUB-BPX12 plasmids, following the protoplast technique and respective transformants were selected, isolated and purified.

The resulting transformed strains were *B. licheniformis* SE2 delap1 (pUB-BPX12); delap3 (pUB-BPX12); and delap6 (pUB-BPX12). The transformants were then placed in respective cultures, as will be described below in Example 33, to produce the xylanase of the present invention. The presence of this plasmid confers to the resulting recombinant deleted *B. licheniformis* SE2 strains the following properties:

1. Extracellular production of xylanase; and
2. Kanamycin or phleomycin resistance.

EXAMPLE 30

Transformation of Deleted *B. licheniformis* SE2 Strains With Other Expression Vectors pUBDEBRA1 (FIG. 5) obtained as was described above in Example 18, pKAC1 (FIG. 6) obtained as was described above in Example 19, pLI1 (FIG. 7) obtained as was described above in Example 20, pL7SBT (FIG. 8) obtained as was described above in Example 21, and pL7TAKA (FIG. 9) obtained as was described above in Example 22 were all extracted from their respective hosts and isolated and purified. Five cultures of each of the deleted *B. licheniformis* SE2 strains (delap1, delap3 and delap6) were obtained, as described above in Examples 28. A respective culture of each of these deleted strains was then transformed by one of the respective plasmids. Transformations were performed using the protoplast technique.

Transformants in each of these five respective cultures were then selected, isolated and purified.

The transformants were then placed in further respective cultures as will be described below in Example 34 to produce the respective enzyme that is coded for thereby.

EXAMPLE 31

Transformation of *B. subtilis* SE3 With Expression Vectors pUB-BPX12 (FIG. 4) obtained as was described above in Example 17, pUBDEBRA1 (FIG. 5) obtained as was described above in Example 18, pKAC1 (FIG. 6) obtained as was described above in Example 19, pLI1 (FIG. 7) obtained as was described above in Example 20, pL7SBT (FIG. 8) obtained as was described above in Example 21, and pL7TAKA (FIG. 9) obtained as was described above in Example 22 were all extracted from their respective hosts and isolated and purified. Six (6) cultures of *Bacillus subtilis* SE3 were prepared. Each of the cultures was then transformed by one of the respective plasmids. Transformations were performed using the protoplast technique.

Transformants in each of these five respective cultures were then selected, isolated and, purified.

The transformants were then placed in further respective cultures as will be described below in Example 35 to produce the respective enzyme that is coded for thereby.

EXAMPLE 32

Transformation of *B. pumilus* PRL B12 With pUB-BPX12 pUB-BPX12 (FIG. 4) was extracted from the *E. coli* MC1061 obtained in Example 17 and isolated and purified. pUB-BPX12 was then introduced by transformation in the strain *B. pumilus* PRL B12 by the protoplast method. The transformants were directly selected on DM3 media in the presence of phleomycine at 20 μg/ml.

Transformants in each of these five respective cultures were then selected, isolated and purified.

The transformants were then placed in further respective cultures as will be described below in Example 36 to produce the xylanase of the present invention.

EXAMPLE 33

Expression of pUB-BPX12 in Deleted *B. licheniformis* SE2 Strains

Respective cultures of the deleted *B. licheniformis* SE2 strains (delap1, delap3 and delap6), that were transformed with the expression vector pUB-BPX12 as described above in Example 29, were obtained.

The transformants were cultivated for 17 hours at 37° C. in a preculture of L-B medium supplemented with 0.5% glucose (w/v), and 20 μg/ml (w/v) kanamycine. This preculture was inoculated (5% v/v) into 50 ml of M2 medium (described in example 1), supplemented with 20 μg/ml kanamycin, in baffled erlenmeyer flasks. The cultures were carried out under agitation during 80 hours at 37° C. After 80 hours of culture in the conditions described, the cellular biomass was eliminated by centrifugation at 5000 RPM for 10 minutes.

The enzymatic activity of the xylanase in the culture broths was then determined and the quantity of protein (μ grams) was then calculated in function of specific activity of the enzyme. These results were then compared to the enzymatic activity of the host strain *B. licheniformis* SE2 delap1, transformed by the pUB131 control plasmid (see Table 10 below).

The results obtained are presented below in Table 10 and are given in percentages by comparison to the quantity of alkaline protease produced by the deleted *B. licheniformis* SE2 strain containing the plasmid pLI1 (FIG. 7), which contains an alkaline protease Carlsberg gene.

EXAMPLE 34

Expression by Expression Vectors in Deleted *B. licheniformis* SE2 Strains

Respective cultures of the deleted *B. licheniformis* SE2 strains (delap1, delap3 and delap6), that were transformed with the expression vectors pUBDEBRA1, pKAC1, pLI1, pL7SBT and pL7TAKA, as described above in Example 30, were obtained.

The transformants were cultivated for 17 hours at 37° C. in a preculture of L-B medium supplemented with 0.5% glucose (w/v), and 20 μg/ml (w/v) kanamycine. This preculture was inoculated (5% v/v) into 50 ml of M2 medium (described in example 1), supplemented with 20 pg/ml kanamycin, in baffled erlenmeyer flasks. The cultures were carried out under agitation during 80 hours at 37° C. After 80 hours of culture in the conditions described, the cellular biomass was eliminated by centrifugation at 5000 RPM for 10 minutes.

The enzymatic activity of the pullulanase, α-amylase and alkaline proteases in the culture broths were then determined and the quantity of protein (μ grams) was then calculated in function of specific activity of the enzyme. These results were then compared to the enzymatic activity of the host strain *B. licheniformis* SE2 delap1, transformed by the pUB131 control plasmid (see Table 10 below).

The results obtained are presented below in Table 10 and are given in percentages by comparison to the quantity of alkaline protease produced by the deleted *B. licheniformis* SE2 strain containing the plasmid pLI1 (FIG. 7), which contains an alkaline protease Carlsberg gene.

EXAMPLE 35

Expression by Expression Vectors in *B. subtilis* SE3

Respective cultures of *B. subtilis* SE3 that were transformed with the expression vectors pUB-BPX12, pUBDEBRA1, pKAC1, pLI1, pL7SBT, and pL7TAKA, as described above in Example 31, were obtained.

The transformants were cultivated for 17 hours at 37° C. in a preculture of L-B medium supplemented with 0.5% glucose (w/v), and 20 μg/ml (w/v) kanamycine. This preculture was inoculated (5% v/v) into 50 ml of M3 medium (described in example 1), supplemented with 20 μg/ml kanamycin, in baffled erlenmeyer flasks. The cultures were carried out under agitation during 80 hours at 37° C. After 80 hours of culture in the conditions described, the cellular biomass was eliminated by centrifugation at 5000 RPM for 10 minutes.

The enzymatic activity of the xylanase, pullulanase, amylase and alkaline proteases in the culture broths were then determined and the quantity of protein (μ grams) was then calculated in function of specific activity of the enzyme. These results were then compared to the enzymatic activity of the host strain *B. licheniformis* SE2 delap1, transformed by the pUB131 control plasmid (see Table 10 below).

The results obtained are presented below in Table 10 and are given in percentages by comparison to the quantity of alkaline protease produced by the deleted *B. licheniformis* SE2 delap1 strain containing the plasmid pLI1 (FIG. 7), which contains an alkaline protease Carlsberg gene.

EXAMPLE 36

Expression by Expression Vector pUB-BPX12 In *B. pumilus* PRL B12

A culture of the *B. pumilus* PRL B12 strain, that was transformed with the expression vector pUB-BPX12, as described above in Example 32, was obtained.

The transformants were directly selected on DM3 media in the presence of phleomycine at 20 μg/ml.

A transformant colony was then cultivated for 24 hours at 37° C. in the preculture medium described above in example 1, supplemented with 25 μg/ml (w/v) kanamycine. This preculture was inoculated (5% v/v) into 50 ml of M1 medium (described in example 1), supplemented with 20 μg/ml kanamycin, in a baffled erlenmeyer flask, conforming to the protocol described above in Example 1. The culture was carried out under agitation during 40 hours at 30° C.

After 40 hours of culturing, the extracellular mixture of the culture broth containing the xylanase of *B. pumilus* PRL B12 was separated from the cellular biomass by centrifugation at 5000 rpm for 10 minutes.

The enzymatic activity of the xylanase in the culture broth was then determined and the quantity of protein (μ grams) was then calculated in function of specific activity of the enzyme.

These results were then compared to the enzymatic activity of the host strain *B. licheniformis* SE2 delap1, transformed by the pUB131 control plasmid (see Table 10 below).

The results obtained are presented below in Table 10 and are given in percentages by comparison to the quantity of alkaline protease produced by the deleted *B. licheniformis* SE2 delap1 strain containing the plasmid pLI1 (FIG. 7), which contains an alkaline protease Carlsberg gene.

EXAMPLE 37

Yields of the Various Enzymes Produced From Various Hosts

The various supernatants described above in Examples 33, 34, 35 and 36, were analyzed for the protein content of the respective enzymes secreted from the three Bacillus hosts tested. Results are presented below in table 10.

In Table 10:
(1) stands for *B. licheniformis* SE2 delap1;
(2) stands for *B. licheniformis* SE2 delap3;
(3) stands for *B. licheniformis* SE2 delap6;
(4) stands for *B. subtilis* SE3; and
(5) stands for *B. pumilus* PRL B12.

In table 10, the numbers indicated in the table correspond to the quantity of the respective enzymes (mg protein/ml) secreted by the relevant host strains (mg of enzyme/ml of culture supernatant), expressed as percentages of the quantity of homologous alcaline protease Carlsberg secreted by *B. licheniformis* SE2 delap1, from plasmid pLI1.

The amount of protein corresponding to each enzyme is measured as described in the experimental part under the heading "Methods and Techniques".

"NS" indicates that the plasmids were highly unstable in the corresponding host strains, and productivity data are therefore not available.

TABLE 10

Productivity (%) of Expression Vectors in *B. licheniformis* SE2 delap strains

| Plasmid | Expressed gene | Host Strain Relative Yield | | | | |
| --- | --- | --- | --- | --- | --- | --- |
| | | (1) | (2) | (3) | (4) | (5) |
| pLI1 | (subtilisin Carlsberg) | 100 | — | — | NS | — |
| pUB-PBX12 | (xylanase) | 215 | — | 220 | 9 | 47 |
| pUBDEBRA1 | (pullulanase) | 95 | — | — | NS | — |
| pKAC1 | (subtilisin 168) | 35 | — | 101 | <5 | — |

TABLE 10-continued

Productivity (%) of Expression Vectors in *B. licheniformis* SE2 delap strains

| Plasmid | Expressed gene | Host Strain Relative Yield | | | | |
| --- | --- | --- | --- | --- | --- | --- |
| | | (1) | (2) | (3) | (4) | (5) |
| pL7SBT | (subtilisin 168) | 50 | — | 133 | NS | — |
| pL7TAKA | (α-amylase) | 10 | — | 32 | NS | — |

The results show that the deleted *B. licheniformis* strains are a much more advantageous host than *B. subtilis*, in that secretion of heterologous proteins is much more efficient. For example, *B. licheniformis* SE2 delap6 (pUB-BPX12) is able to produce 24 times more xylanase than *B. subtilis* SE3 (pUB-BPX12), under the same conditions, and using the same expression vector (pUB-BPX12). The yields obtained with expression vector pUB-BPX12 in this *B. licheniformis* SE2 delap6 host are even 4.8-fold higher than the yields obtained with the same expression vector in the strictly homologous expression host *B. pumilus* PRL B12.

Moreover, several expression vectors were found to be totally unstable in *B. subtilis* SE3: pLI1 (Carlsberg protease), pL7TAKA (α-amylase), pL7SBT (subtilisin 168), and pUBDEBRA1 (pullulanase). In all these cases, transformants could hardly been obtained, since deletions in the expression vectors occurred at a high frequency. On the other hand, in the *B. licheniformis* SE2 delap1 and delap6 strains, the same expression vectors were found to be very stable, and good yields were obtained.

Some heterologous enzymes, for example xylanase (220%), and to a lesser extent, subtilisin 168 (133%) were produced in even larger quantities than the homologous Carlsberg protease used as a reference in this experiment.

Some enzymes are produced at a similar yield to the homologous protease Carlsberg used as reference in this experiment (for example, pullulanase (105%)).

Table 10 also demonstrates the better efficiency of the homologous transcription promoter from *B. licheniformis*, to drive the synthesis of subtilisin 168. Comparing the results for the expression of the pL7SBT to those seen for the pKAC1 plasmid, it can be seen that the productivity is indeed 31%. higher using the homologous alkaline protease transcription promoter than the heterologous *B. subtilis* promoter.

Thus, the results of Table 10 clearly show that the deleted *B. licheniformis* SE2 strains, as described herein, are excellent hosts for the heterologous expression of proteins.

Obviously many modifications may be made without departing from the basic spirit of the invention. Accordingly, it will be appreciated by those skilled in the art that within the scope of the appended claims, the invention may be practiced other than has been specifically described herein.

BIBLIOGRAPHY (1) Simpson, F., Microbial Pentosanases II. Some Factors Affecting the Production of Pentosanases by *Bacillus pumilus* and *Bacillus subtilis*, Can. J. Microbiol., 2:28–38 (1956).
(2) German Patent Application, Serial Number DE 4023458.
(3) Molecular Cloning—Laboratory Manual, (Sambrook, Fritsch, Maniatis) 2nd edition (1989).
(4) Molecular Biological Methods for Bacillus (Harwood, C. R., and Cutting, S. M., eds) John Wiley and Sons (1990).

(5) DNA Cloning, Volume II, Editor: Glover, D. M., IRL press, Oxford, (1985)
(6) Molecular Cloning, A Laboratory Manual. (Maniatis, T., Fritsch, E. F., and Samrook, J) Cold Spring Harbor Laboratory (1982).

LIST OF ABBREVIATIONS USED IN DRAWINGS

The following is a list of the abbreviations which have been utilized (throughout the application) in the drawings
REP Replication Initiation Protein
ORI+Origin qf Plus Strand Synthesis
ORI−Minus Origin of Replication
KMR Gene Conferring Resistance to Kanamycin
BLMR Gene Conferring Resistance to Bleomycin
MAT Mature Protein
PRE Pre-Sequence
PP Pre-Pro Sequence
BPUXYL Sequence Coding for B. pumilus PRL B12 xylanase
BSUAPR Sequence Coding for B. subtilis subtilisin
BLIAMY Sequence Coding for B. licheniformis alpha-amylase
BLIAPR Sequence Coding for B. licheniformis alkaline protease
5'BLIAPR 5' Upstream Sequence of BLIAPR
3'BLIAPR 3' Downstream Sequence of BLIAPR

```
                         SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
        (A) LENGTH: 1022 base pairs
        (B) TYPE: nucleic acid
        (C) STRANDEDNESS: single
        (D) TOPOLOGY: linear (ii) MOLECULE TYPE: genomic DNA (vi) ORIGINAL SOURCE:
        (A) ORGANISM: Bacillus pumilus
        (B) STRAIN: PRL B12

(xi) SEQUENCE DESCRIPTION: SEQ ID NO: 1:

TCATGTAACT CGCCTTGATC TATTTCATTT GTATCAAAGG ATTTATACAC AAACAAGAGA        60

CATCCATGCC GGGTTAAAGC AGTATCGTTC CATCTAACAG AGAAGGNCTG CATGAAAGGA       120

GGTGATGGGT TTTTCATCTT AGGGATGACA GAACAATACG GATGAAAAAA GGAGAGGGAT      180

GGAAA ATG AAT TTG AAA AGA TTG AGG CTG TTG TTT GTG ATG TGT ATT GGA       230
      Met Asn Leu Lys Arg Leu Arg Leu Leu Phe Val Met Cys Ile Gly
          -25                 -20                 -15

TTT GTG CTG ACA CTG ACG GCT GTG CCG GCT CAT GCG GAA ACG ATT TAT        278
Phe Val Leu Thr Leu Thr Ala Val Pro Ala His Ala Glu Thr Ile Tyr
        -10                  -5                   1

GAT AAT AGG ATA GGG ACA CAC AGC GGA TAC GAT TTT GAA TTA TGG AAG        326
Asp Asn Arg Ile Gly Thr His Ser Gly Tyr Asp Phe Glu Leu Trp Lys
 5                  10                  15                  20

GAT TAC GGA AAT ACC TCG ATG ACA CTC AAT AAC GGC GGG GCA TTT AGT        374
Asp Tyr Gly Asn Thr Ser Met Thr Leu Asn Asn Gly Gly Ala Phe Ser
                25                  30                  35

GCA AGC TGG AAC AAT ATT GGA AAT GCC TTA TTT CGA AAA GGA AAG AAG        422
Ala Ser Trp Asn Asn Ile Gly Asn Ala Leu Phe Arg Lys Gly Lys Lys
                40                  45                  50

TTT GAT TCC ACT AAA ACT CAT CAT CAA CTT GGC AAC ATC TCC ATC AAC        470
Phe Asp Ser Thr Lys Thr His His Gln Leu Gly Asn Ile Ser Ile Asn
                55                  60                  65

TAC AAC GCA GCC TTT AAC CCG GGC GGG AAT TCC TAT TTA TGT GTC TAT        518
Tyr Asn Ala Ala Phe Asn Pro Gly Gly Asn Ser Tyr Leu Cys Val Tyr
 70                  75                  80
```

```
GGC TGG ACA CAA TCT CCA TTA GCT GAA TAC TAC ATT GTT GAG TCA TGG      566
Gly Trp Thr Gln Ser Pro Leu Ala Glu Tyr Tyr Ile Val Glu Ser Trp
 85                  90                  95                 100

GGC ACA TAT CGT CCA ACA GGA ACG TAT AAA GGA TCA TTT TAT GCC GAT      614
Gly Thr Tyr Arg Pro Thr Gly Thr Tyr Lys Gly Ser Phe Tyr Ala Asp
                105                 110                 115

GGA GGC ACA TAT GAC ATA TAT GAA ACG CTC CGT GTC AAT CAG CCT TCT      662
Gly Gly Thr Tyr Asp Ile Tyr Glu Thr Leu Arg Val Asn Gln Pro Ser
            120                 125                 130

ATC ATT GGA GAC GCT ACC TTC AAA CAA TAT TGG AGT GTA CGT CAA ACA      710
Ile Ile Gly Asp Ala Thr Phe Lys Gln Tyr Trp Ser Val Arg Gln Thr
        135                 140                 145

AAA CGC ACA AGC GGA ACG GTC TCC GTC AGT GAG CAT TTT AAA AAA TGG      758
Lys Arg Thr Ser Gly Thr Val Ser Val Ser Glu His Phe Lys Lys Trp
150                 155                 160

GAA AGC TTA GGC ATG CCA ATG GGA AAA ATG TAT GAA ACA GCA TTA ACT      806
Glu Ser Leu Gly Met Pro Met Gly Lys Met Tyr Glu Thr Ala Leu Thr
165                 170                 175                 180

GTA GAA GGC TAC CGA AGC AAC GGA AGT GCG AAT GTC ATG ACG AAT CAG      854
Val Glu Gly Tyr Arg Ser Asn Gly Ser Ala Asn Val Met Thr Asn Gln
                185                 190                 195

CTG ATG ATT CGA TAAAAGCATA TGAAAAAAGC CAGCAAAAAA TGGCTGGCTT          906
Leu Met Ile Arg
            200

TTTTCTATGA TAATTTTTCA ACTTCCACTC TGCCAGAAAA GAACGTCGCG CCGCCTCCCA    966

TATCTGCCAA TCGATCAGGT GTTAACCCAT TCACTAAATG CTTTTTGCCT TTTTGA        1022

(2) INFORMATION FOR SEQ ID NO: 2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: Peptide (v) FRAGMENT TYPE: N-terminal (vi) ORIGINAL SOURCE:
        (A) ORGANISM: Bacillus pumilus
        (B) STRAIN: PRL B12

(xi) SEQUENCE DESCRIPTION: SEQ ID NO: 2:

Glu Thr Ile Tyr Asp Asn Arg Ile Gly Thr His Ser Gly Tyr Asp
 1               5                  10                  15

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 3:

GTAGAGGATC ATCATGT                                                     17

(2) INFORMATION FOR SEQ ID NO: 4:

(i) SEQUENCE CHARACTERISTICS:
        (A) LENGTH: 19 base pairs
        (B) TYPE: nucleic acid
```

(C) STRANDEDNESS: single
(D) TOPOLOGY: linear (ii) MOLECULE TYPE: nucleic acid (synthetic oligonucleotide)

(xi) SEQUENCE DESCRIPTION: SEQ ID NO: 4:

TACCTTGTCT ACAAACCCC                                         19

(2) INFORMATION FOR SEQ ID NO: 5:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: nucleic acid (synthetic oligonucleotide)

(xi) SEQUENCE DESCRIPTION: SEQ ID NO: 5:

TGAGTTGCTA GTAACATCTC ACCGA                                  25

(2) INFORMATION FOR SEQ ID NO: 6:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: nucleic acid (synthetic oligonucleotide)

(xi) SEQUENCE DESCRIPTION: SEQ ID NO: 6:

AAGCTTGTAT GCCTGCAG                                          18

(2) INFORMATION FOR SEQ ID NO: 7:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: nucleic acid (synthetic oligonucleotide)

(xi) SEQUENCE DESCRIPTION: SEQ ID NO: 7:

GATCCCCTTG GCTGCAGGAG CT                                     22

(2) INFORMATION FOR SEQ ID NO: 8:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: nucleic acid (synthetic oligonucleotide)

(xi) SEQUENCE DESCRIPTION: SEQ ID NO: 8:

CCTGCAGCCA AGGG                                              14

(2) INFORMATION FOR SEQ ID NO: 9:

(i) SEQUENCE CHARACTERISTICS:
    (A) LENGTH: 52 base pairs
    (B) TYPE: nucleic acid
    (C) STRANDEDNESS: single
    (D) TOPOLOGY: linear (ii) MOLECULE TYPE: nucleic acid (synthetic oligonucleotide)

(xi) SEQUENCE DESCRIPTION: SEQ ID NO: 9:

GATCCCCGGG ACCTTAGGCC TTTAATTAAC CTTGGCGGCC GCTCGAGGAG CT            52

(2) INFORMATION FOR SEQ ID NO: 10:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 10:

CCTCGAGCGG CCGCCAAGGT TAATTAAAGG CCTAAGGTCC CGGG                     44

(2) INFORMATION FOR SEQ ID NO: 11:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 11:

ATTATATTAT CCTTCTATTT AATTAATCTG AATAAAGAGG AG                       42

(2) INFORMATION FOR SEQ ID NO: 12:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 12:

CGCTTAATTA AAAATGAGGA GGGAACCGAG TGAGAAGCAA AAAATTGTGG ATCAGCTT      58

(2) INFORMATION FOR SEQ ID NO: 13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 13:

GATCATGGAA CGAGCTCAAC ATGCGGAGAA AGAAGAG                             37

(2) INFORMATION FOR SEQ ID NO: 14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 14:

CTTGTTAAAA ATTCGGAATA TTTAATTAAA TCATATGTTT CA                       42

(2) INFORMATION FOR SEQ ID NO: 15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 15:

```
GCTGCAAAGC ATAATGATGA CGGTCC                                    26
```

(2) INFORMATION FOR SEQ ID NO: 16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 16:

```
GGCGGAGCAA GCTTTGTGG                                            19
```

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 17:

```
ATGGCTCCTG GCGCAGGC                                             18
```

(2) INFORMATION FOR SEQ ID NO: 18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 18:

```
CTTGGAGCTC GTTAACAGAT CT                                        22
```

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 19:

```
CTTGAGATCT GTTAACGAGC TC                                        22
```

(2) INFORMATION FOR SEQ ID NO: 20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 20:

```
CATCTAATCT TCAACACCCG GGCCCGTTTG TTGAAC                              36
```

(2) INFORMATION FOR SEQ ID NO: 21:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 21:

```
CAAAATAAAA AAGATACAAC CCGGGTCTCT CGTATCTTTT AT                       42
```

(2) INFORMATION FOR SEQ ID NO: 22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 22:

```
CCTTTAATTA ACCTTGGCGG CCGCTCGAGG AGCT                                34
```

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: nucleic acid (synthetic oligonucleotide)

(xi) SEQUENCE DESCRIPTION: SEQ ID NO: 23:

```
CCTCGAGCGG CCGCCAAGGT TAATTAAAGG                                     30
```

(2) INFORMATION FOR SEQ ID NO: 24:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: protein (v) FRAGMENT TYPE: internal fragment (vi) ORIGINAL SOURCE:
        (A) ORGANISM: Bacillus pumilus
        (B) STRAIN: PRL B12

(xi) SEQUENCE DESCRIPTION: SEQ ID NO: 24:

Glu Thr Ile Tyr Asp Asn Arg Ile Gly Thr His Ser Gly Tyr Asp Phe
1               5                   10                  15

Glu Leu Trp Lys Asp Tyr Gly Asn Thr Ser Met Thr Leu Asn Asn Gly
            20                  25                  30

Gly Ala Phe Ser Ala Ser Trp Asn Asn Ile Gly Asn Ala Leu Phe Arg
            35                  40                  45

Lys Gly Lys Lys Phe Asp Ser Thr Lys Thr His His Gln Leu Gly Asn
        50                  55                  60

Ile Ser Ile Asn Tyr Asn Ala Ala Phe Asn Pro Gly Gly Asn Ser Tyr
65                  70                  75                  80

Leu Cys Val Tyr Gly Trp Thr Gln Ser Pro Leu Ala Glu Tyr Tyr Ile
                85                  90                  95

Val Glu Ser Trp Gly Thr Tyr Arg Pro Thr Gly Thr Tyr Lys Gly Ser
                100                 105                 110

Phe Tyr Ala Asp Gly Gly Thr Tyr Asp Ile Tyr Glu Thr Leu Arg Val
            115                 120                 125

Asn Gln Pro Ser Ile Ile Gly Asp Ala Thr Phe Lys Gln Tyr Trp Ser
130                 135                 140

Val Arg Gln Thr Lys Arg Thr Ser Gly Thr Val Ser Val Ser Glu His
145                 150                 155                 160

Phe Lys Lys Trp Glu Ser Leu Gly Met Pro Met Gly Lys Met Tyr Glu
                165                 170                 175

Thr Ala Leu Thr Val Glu Gly Tyr Arg Ser Asn Gly Ser Ala Asn Val
            180                 185                 190

Met Thr Asn Gln Leu Met Ile Arg
            195                 200

(2) INFORMATION FOR SEQ ID NO: 25:

(i) SEQUENCE CHARACTERISTICS:
       (A) LENGTH: 27 amino acids
       (B) TYPE: amino acid
       (C) STRANDEDNESS: single
       (D) TOPOLOGY: linear (ii) MOLECULE TYPE: peptide (v) FRAGMENT TYPE: internal fragment (vi) ORIGINAL SOURCE:
       (A) ORGANISM: Bacillus pumilus
       (B) STRAIN: PRL B12

(xi) SEQUENCE DESCRIPTION: SEQ ID NO: 25:

Met Asn Leu Lys Arg Leu Arg Leu Leu Phe Val Met Cys Ile Gly Phe
        -25                 -20                 -15

Val Leu Thr Leu Thr Ala Val Pro Ala His Ala
        -10                 -5

(2) INFORMATION FOR SEQ ID NO: 26:

(i) SEQUENCE CHARACTERISTICS:
       (A) LENGTH: 600 base pairs
       (B) TYPE: nucleic acid
       (C) STRANDEDNESS: single
       (D) TOPOLOGY: linear (ii) MOLECULE TYPE: genomic DNA (xi) SEQUENCE DESCRIPTION: SEQ ID NO: 26:

```
GAAACGATTT ATGATAATAG GATAGGGACA CACAGCGGAT ACGATTTTGA ATTATGGAAG      60
GATTACGGAA ATACCTCGAT GACACTCAAT AACGGCGGGG CATTTAGTGC AAGCTGGAAC     120
AATATTGGAA ATGCCTTATT TCGAAAAGGA AAGAAGTTTG ATTCCACTAA AACTCATCAT     180
CAACTTGGCA ACATCTCCAT CAACTACAAC GCAGCCTTTA ACCCGGGCGG GAATTCCTAT     240
TTATGTGTCT ATGGCTGGAC ACAATCTCCA TTAGCTGAAT ACTACATTGT TGAGTCATGG     300
GGCACATATC GTCCAACAGG AACGTATAAA GGATCATTTT ATGCCGATGG AGGCACATAT     360
GACATATATG AAACGCTCCG TGTCAATCAG CCTTCTATCA TTGGAGACGC TACCTTCAAA     420
CAATATTGGA GTGTACGTCA AACAAAACGC ACAAGCGGAA CGGTCTCCGT CAGTGAGCAT     480
TTTAAAAAAT GGGAAAGCTT AGGCATGCCA ATGGGAAAAA TGTATGAAAC AGCATTAACT     540
GTAGAAGGCT ACCGAAGCAA CGGAAGTGCG AATGTCATGA CGAATCAGCT GATGATTCGA     600
```

(2) INFORMATION FOR SEQ ID NO: 27:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 27:

```
ATGAATTTGA AAAGATTGAG GCTGTTGTTT GTGATGTGTA TTGGATTTGT GCTGACACTG      60
ACGGCTGTGC CGGCTCATGC G                                                81
```

(2) INFORMATION FOR SEQ ID NO: 28:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 28:

```
TCATGTAACT CGCCTTGATC TATTTCATTT GTATCAAAGG ATTTATACAC AAACAAGAGA      60
CATCCATGCC GGGTTAAAGC AGTATCGTTC CATCTAACAG AGAAGGNCTG CATGAAAGGA     120
GGTGATGGGT TTTTCATCTT AGGGATGACA GAACAATACG GATGAAAAAA GGAGAGGGAT     180
GGAAA                                                                185
```

(2) INFORMATION FOR SEQ ID NO: 29:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 29:

```
TAAAAGCATA TGAAAAAAGC CAGCAAAAAA TGGCTGGCTT TTTTCTATGA TAATTTTTCA      60
ACTTCCACTC TGCCAGAAAA GAACGTCGCG CCGCCTCCCA TATCTGCCAA TCGATCAGGT     120
GTTAACCCAT TCACTAAATG CTTTTTGCCT TTTTGA                               156
```

(2) INFORMATION FOR SEQ ID NO: 30:

(i) SEQUENCE CHARACTERISTICS:
        (A) LENGTH: 681 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 30:

```
ATGAATTTGA AAAGATTGAG GCTGTTGTTT GTGATGTGTA TTGGATTTGT GCTGACACTG      60

ACGGCTGTGC CGGCTCATGC GGAAACGATT TATGATAATA GGATAGGGAC ACACAGCGGA     120

TACGATTTTG AATTATGGAA GGATTACGGA AATACCTCGA TGACACTCAA TAACGGCGGG     180

GCATTTAGTG CAAGCTGGAA CAATATTGGA AATGCCTTAT TTCGAAAAGG AAAGAAGTTT     240

GATTCCACTA AAACTCATCA TCAACTTGGC AACATCTCCA TCAACTACAA CGCAGCCTTT     300

AACCCGGGCG GGAATTCCTA TTTATGTGTC TATGGCTGGA CACAATCTCC ATTAGCTGAA     360

TACTACATTG TTGAGTCATG GGGCACATAT CGTCCAACAG GAACGTATAA AGGATCATTT     420

TATGCCGATG GAGGCACATA TGACATATAT GAAACGCTCC GTGTCAATCA GCCTTCTATC     480

ATTGGAGACG CTACCTTCAA ACAATATTGG AGTGTACGTC AAACAAAACG CACAAGCGGA     540

ACGGTCTCCG TCAGTGAGCA TTTTAAAAAA TGGGAAAGCT TAGGCATGCC AATGGGAAAA     600

ATGTATGAAA CAGCATTAAC TGTAGAAGGC TACCGAAGCA ACGGAAGTGC GAATGTCATG     660

ACGAATCAGC TGATGATTCG A                                              681
```

(2) INFORMATION FOR SEQ ID NO: 31:

(i) SEQUENCE CHARACTERISTICS:
        (A) LENGTH: 227 amino acids
        (B) TYPE: amino acid
        (C) STRANDEDNESS: single
        (D) TOPOLOGY: linear (ii) MOLECULE TYPE: protein (v) FRAGMENT TYPE: internal fragment (vi) ORIGINAL SOURCE:
        (A) ORGANISM: Bacillus pumilus
        (B) STRAIN: PRL B12

(xi) SEQUENCE DESCRIPTION: SEQ ID NO: 31:

```
Met Asn Leu Lys Arg Leu Arg Leu Leu Phe Val Met Cys Ile Gly Phe
        -25                 -20                 -15

Val Leu Thr Leu Thr Ala Val Pro Ala His Ala Glu Thr Ile Tyr Asp
    -10                  -5                   1                5

Asn Arg Ile Gly Thr His Ser Gly Tyr Asp Phe Glu Leu Trp Lys Asp
                 10                  15                  20

Tyr Gly Asn Thr Ser Met Thr Leu Asn Asn Gly Ala Phe Ser Ala
                 25                  30                  35

Ser Trp Asn Asn Ile Gly Asn Ala Leu Phe Arg Lys Gly Lys Phe
             40                  45                  50

Asp Ser Thr Lys Thr His His Gln Leu Gly Asn Ile Ser Ile Asn Tyr
         55                  60                  65

Asn Ala Ala Phe Asn Pro Gly Gly Asn Ser Tyr Leu Cys Val Tyr Gly
 70                  75                  80                  85

Trp Thr Gln Ser Pro Leu Ala Glu Tyr Tyr Ile Val Glu Ser Trp Gly
                 90                  95                 100
```

```
Thr Tyr Arg Pro Thr Gly Thr Tyr Lys Gly Ser Phe Tyr Ala Asp Gly
            105                 110                 115

Gly Thr Tyr Asp Ile Tyr Glu Thr Leu Arg Val Asn Gln Pro Ser Ile
        120                 125                 130

Ile Gly Asp Ala Thr Phe Lys Gln Tyr Trp Ser Val Arg Gln Thr Lys
    135                 140                 145

Arg Thr Ser Gly Thr Val Ser Val Ser Glu His Phe Lys Lys Trp Glu
150                 155                 160                 165

Ser Leu Gly Met Pro Met Gly Lys Met Tyr Glu Thr Ala Leu Thr Val
                170                 175                 180

Glu Gly Tyr Arg Ser Asn Gly Ser Ala Asn Val Met Thr Asn Gln Leu
            185                 190                 195

Met Ile Arg
        200

(2) INFORMATION FOR SEQ ID NO: 32:

(i) SEQUENCE CHARACTERISTICS:
        (A) LENGTH: 681 base pairs
        (B) TYPE: nucleic acid
        (C) STRANDEDNESS: single
        (D) TOPOLOGY: linear (ii) MOLECULE TYPE: genomic DNA (vi) ORIGINAL SOURCE:
        (A) ORGANISM: Bacillus pumilus
        (B) STRAIN: PRL B12

(xi) SEQUENCE DESCRIPTION: SEQ ID NO: 32:

ATG AAT TTG AAA AGA TTG AGG CTG TTG TTT GTG ATG TGT ATT GGA TTT      48
Met Asn Leu Lys Arg Leu Arg Leu Leu Phe Val Met Cys Ile Gly Phe
        -25                 -20                 -15

GTG CTG ACA CTG ACG GCT GTG CCG GCT CAT GCG GAA ACG ATT TAT GAT      96
Val Leu Thr Leu Thr Ala Val Pro Ala His Ala Glu Thr Ile Tyr Asp
    -10                 -5                   1                 5

AAT AGG ATA GGG ACA CAC AGC GGA TAC GAT TTT GAA TTA TGG AAG GAT     144
Asn Arg Ile Gly Thr His Ser Gly Tyr Asp Phe Glu Leu Trp Lys Asp
            10                  15                  20

TAC GGA AAT ACC TCG ATG ACA CTC AAT AAC GGC GGG GCA TTT AGT GCA     192
Tyr Gly Asn Thr Ser Met Thr Leu Asn Asn Gly Gly Ala Phe Ser Ala
        25                  30                  35

AGC TGG AAC AAT ATT GGA AAT GCC TTA TTT CGA AAA GGA AAG AAG TTT     240
Ser Trp Asn Asn Ile Gly Asn Ala Leu Phe Arg Lys Gly Lys Lys Phe
    40                  45                  50

GAT TCC ACT AAA ACT CAT CAT CAA CTT GGC AAC ATC TCC ATC AAC TAC     288
Asp Ser Thr Lys Thr His His Gln Leu Gly Asn Ile Ser Ile Asn Tyr
55                  60                  65

AAC GCA GCC TTT AAC CCG GGC GGG AAT TCC TAT TTA TGT GTC TAT GGC     336
Asn Ala Ala Phe Asn Pro Gly Gly Asn Ser Tyr Leu Cys Val Tyr Gly
70                  75                  80                  85

TGG ACA CAA TCT CCA TTA GCT GAA TAC TAC ATT GTT GAG TCA TGG GGC     384
Trp Thr Gln Ser Pro Leu Ala Glu Tyr Tyr Ile Val Glu Ser Trp Gly
                90                  95                 100

ACA TAT CGT CCA ACA GGA ACG TAT AAA GGA TCA TTT TAT GCC GAT GGA     432
Thr Tyr Arg Pro Thr Gly Thr Tyr Lys Gly Ser Phe Tyr Ala Asp Gly
            105                 110                 115

GGC ACA TAT GAC ATA TAT GAA ACG CTC CGT GTC AAT CAG CCT TCT ATC     480
Gly Thr Tyr Asp Ile Tyr Glu Thr Leu Arg Val Asn Gln Pro Ser Ile
        120                 125                 130
```

```
ATT GGA GAC GCT ACC TTC AAA CAA TAT TGG AGT GTA CGT CAA ACA AAA        528
Ile Gly Asp Ala Thr Phe Lys Gln Tyr Trp Ser Val Arg Gln Thr Lys
        135                 140                 145

CGC ACA AGC GGA ACG GTC TCC GTC AGT GAG CAT TTT AAA AAA TGG GAA        576
Arg Thr Ser Gly Thr Val Ser Val Ser Glu His Phe Lys Lys Trp Glu
150                 155                 160                 165

AGC TTA GGC ATG CCA ATG GGA AAA ATG TAT GAA ACA GCA TTA ACT GTA        624
Ser Leu Gly Met Pro Met Gly Lys Met Tyr Glu Thr Ala Leu Thr Val
                170                 175                 180

GAA GGC TAC CGA AGC AAC GGA AGT GCG AAT GTC ATG ACG AAT CAG CTG        672
Glu Gly Tyr Arg Ser Asn Gly Ser Ala Asn Val Met Thr Asn Gln Leu
            185                 190                 195

ATG ATT CGA                                                            681
Met Ile Arg
        200

(2) INFORMATION FOR SEQ ID NO: 33:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: genomic DNA (vi) ORIGINAL SOURCE:
        (A) ORGANISM: Bacillus pumilus
        (B) STRAIN: PRL B12

(xi) SEQUENCE DESCRIPTION: SEQ ID NO: 33:

ATG AAT TTG AAA AGA TTG AGG CTG TTG TTT GTG ATG TGT ATT GGA TTT         48
Met Asn Leu Lys Arg Leu Arg Leu Leu Phe Val Met Cys Ile Gly Phe
        -25                 -20                 -15

GTG CTG ACA CTG ACG GCT GTG CCG GCT CAT GCG                             81
Val Leu Thr Leu Thr Ala Val Pro Ala His Ala
    -10                  -5

(2) INFORMATION FOR SEQ ID NO: 34:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: genomic DNA (vi) ORIGINAL SOURCE:
        (A) ORGANISM: Bacillus pumilus
        (B) STRAIN: PRL B12

(xi) SEQUENCE DESCRIPTION: SEQ ID NO: 34:

GAA ACG ATT TAT GAT AAT AGG ATA GGG ACA CAC AGC GGA TAC GAT TTT         48
Glu Thr Ile Tyr Asp Asn Arg Ile Gly Thr His Ser Gly Tyr Asp Phe
1                   5                   10                  15

GAA TTA TGG AAG GAT TAC GGA AAT ACC TCG ATG ACA CTC AAT AAC GGC         96
Glu Leu Trp Lys Asp Tyr Gly Asn Thr Ser Met Thr Leu Asn Asn Gly
            20                  25                  30

GGG GCA TTT AGT GCA AGC TGG AAC AAT ATT GGA AAT GCC TTA TTT CGA        144
Gly Ala Phe Ser Ala Ser Trp Asn Asn Ile Gly Asn Ala Leu Phe Arg
        35                  40                  45

AAA GGA AAG AAG TTT GAT TCC ACT AAA ACT CAT CAT CAA CTT GGC AAC        192
Lys Gly Lys Lys Phe Asp Ser Thr Lys Thr His His Gln Leu Gly Asn
50                  55                  60
```

```
ATC TCC ATC AAC TAC AAC GCA GCC TTT AAC CCG GGC GGG AAT TCC TAT      240
Ile Ser Ile Asn Tyr Asn Ala Ala Phe Asn Pro Gly Gly Asn Ser Tyr
 65                  70                  75                  80

TTA TGT GTC TAT GGC TGG ACA CAA TCT CCA TTA GCT GAA TAC TAC ATT      288
Leu Cys Val Tyr Gly Trp Thr Gln Ser Pro Leu Ala Glu Tyr Tyr Ile
                 85                  90                  95

GTT GAG TCA TGG GGC ACA TAT CGT CCA ACA GGA ACG TAT AAA GGA TCA      336
Val Glu Ser Trp Gly Thr Tyr Arg Pro Thr Gly Thr Tyr Lys Gly Ser
            100                 105                 110

TTT TAT GCC GAT GGA GGC ACA TAT GAC ATA TAT GAA ACG CTC CGT GTC      384
Phe Tyr Ala Asp Gly Gly Thr Tyr Asp Ile Tyr Glu Thr Leu Arg Val
            115                 120                 125

AAT CAG CCT TCT ATC ATT GGA GAC GCT ACC TTC AAA CAA TAT TGG AGT      432
Asn Gln Pro Ser Ile Ile Gly Asp Ala Thr Phe Lys Gln Tyr Trp Ser
130                 135                 140

GTA CGT CAA ACA AAA CGC ACA AGC GGA ACG GTC TCC GTC AGT GAG CAT      480
Val Arg Gln Thr Lys Arg Thr Ser Gly Thr Val Ser Val Ser Glu His
145                 150                 155                 160

TTT AAA AAA TGG GAA AGC TTA GGC ATG CCA ATG GGA AAA ATG TAT GAA      528
Phe Lys Lys Trp Glu Ser Leu Gly Met Pro Met Gly Lys Met Tyr Glu
                165                 170                 175

ACA GCA TTA ACT GTA GAA GGC TAC CGA AGC AAC GGA AGT GCG AAT GTC      576
Thr Ala Leu Thr Val Glu Gly Tyr Arg Ser Asn Gly Ser Ala Asn Val
            180                 185                 190

ATG ACG AAT CAG CTG ATG ATT CGA                                      600
Met Thr Asn Gln Leu Met Ile Arg
            195                 200

(2) INFORMATION FOR SEQ ID NO: 35:

(i) SEQUENCE CHARACTERISTICS:
        (A) LENGTH: 1022 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 35:

TCATGTAACT CGCCTTGATC TATTTCATTT GTATCAAAGG ATTTATACAC AAACAAGAGA      60

CATCCATGCC GGGTTAAAGC AGTATCGTTC CATCTAACAG AGAAGGNCTG CATGAAAGGA     120

GGTGATGGGT TTTTCATCTT AGGGATGACA GAACAATACG GATGAAAAAA GGAGAGGGAT     180

GGAAAATGAA TTTGAAAAGA TTGAGGCTGT TGTTTGTGAT GTGTATTGGA TTTGTGCTGA     240

CACTGACGGC TGTGCCGGCT CATGCGGAAA CGATTTATGA TAATAGGATA GGGACACACA     300

GCGGATACGA TTTTGAATTA TGGAAGGATT ACGGAAATAC CTCGATGACA CTCAATAACG     360

GCGGGGCATT TAGTGCAAGC TGGAACAATA TTGGAAATGC CTTATTTCGA AAAGGAAAGA     420

AGTTTGATTC CACTAAAACT CATCATCAAC TTGGCAACAT CTCCATCAAC TACAACGCAG     480

CCTTTAACCC GGGCGGGAAT TCCTATTTAT GTGTCTATGG CTGGACACAA TCTCCATTAG     540

CTGAATACTA CATTGTTGAG TCATGGGGCA CATATCGTCC AACAGGAACG TATAAAGGAT     600

CATTTTATGC CGATGGAGGC ACATATGACA TATATGAAAC GCTCCGTGTC AATCAGCCTT     660

CTATCATTGG AGACGCTACC TTCAAACAAT ATTGGAGTGT ACGTCAAACA AAACGCACAA     720

GCGGAACGGT CTCCGTCAGT GAGCATTTTA AAAATGGGA AAGCTTAGGC ATGCCAATGG      780

GAAAAATGTA TGAAACAGCA TTAACTGTAG AAGGCTACCG AAGCAACGGA AGTGCGAATG     840

TCATGACGAA TCAGCTGATG ATTCGATAAA AGCATATGAA AAAAGCCAGC AAAAAATGGC     900
```

-continued

| | | | | |
|---|---|---|---|---|
| TGGCTTTTTT | CTATGATAAT | TTTTCAACTT | CCACTCTGCC | AGAAAAGAAC GTCGCGCCGC | 960 |
| CTCCCATATC | TGCCAATCGA | TCAGGTGTTA | ACCCATTCAC | TAAATGCTTT TTGCCTTTTT | 1020 |
| GA | | | | | 1022 |

What is claimed is:

1. A method for the treatment of lignocellulosic pulp, said method comprising: pretreating the lignocellulosic pulp with a xylanase derived from *Bacillus pumilus* PRL B12 in a bleaching sequence before a chemical treatment step of a delignification stage of the bleaching sequence, wherein said xylanase is effective for facilitating the delignification of said lignocellulosic pulp over the entire alkaline pH range of 7.0 to 9.5.

2. The method of claim 1, wherein said lignocellulosic pulp comprises kraft pulp.

3. The method of claim 1, wherein said bleaching sequences employs a reactive oxidant to facilitate delignification of said lignocellulosic pulp.

4. The method of claim 3, wherein said reactive oxidant is selected from the group consisting of elemental chlorine, chlorine dioxide, peroxides, and ozone.

5. The method of claim 3, wherein said bleaching sequence is a classical bleaching sequence.

6. The method of claim 3, wherein said bleaching sequence is an elemental chlorine free bleaching sequence.

7. The method of claim 1, wherein said bleaching sequence is a totally chlorine free bleaching sequence.

8. The method of claim 2, wherein said kraft pulp is selected from the group consisting of softwood kraft pulp and hardwood kraft pulp.

9. A method for the treatment of lignocellulosic pulp, said method comprising: treating lignocellulosic pulp with a xylanase comprising the amino acid sequence depicted in SEQ ID NO: 24.

10. The method of claim 9, wherein said xylanase is recombinantly produced in a microbial host cell transformed with a DNA molecule comprising a nucleotide sequence encoding said xylanase.

11. The method of claim 10, wherein said microbial host cell is Bacillus.

12. The method of claim 11, wherein said Bacillus is *Bacillus licheniformis*.

13. The method of claim 12, wherein said *Bacillus licheniformis* is devoid of an alkaline protease gene.

14. The method of claim 10, wherein said DNA molecule is an expression vector.

15. The method of claim 10, wherein said DNA molecule comprises a nucleotide sequence depicted in SEQ ID NO:26.

16. The method according to claim 1, wherein said xylanase comprises the amino acid sequence depicted in SEQ ID NO:24.

\* \* \* \* \*